(12) United States Patent
Blum et al.

(10) Patent No.: US 10,795,411 B2
(45) Date of Patent: Oct. 6, 2020

(54) EYEWEAR INCLUDING A REMOTE CONTROL CAMERA AND A DOCKING STATION

(71) Applicant: e-Vision Smart Optics, Inc., Sarasota, FL (US)

(72) Inventors: Ronald Blum, Roanoke, VA (US); William Kokonaski, Gig Harbor, WA (US); Dwight Duston, Laguna Niguel, CA (US)

(73) Assignee: e-Vision Smart Optics, Inc., Sarasota, FL (US)

( * ) Notice: Subject to any disclaimer, the term of this patent is extended or adjusted under 35 U.S.C. 154(b) by 0 days.

(21) Appl. No.: 16/454,823

(22) Filed: Jun. 27, 2019

(65) Prior Publication Data

US 2019/0317551 A1   Oct. 17, 2019

Related U.S. Application Data

(63) Continuation of application No. 15/920,634, filed on Mar. 14, 2018, now Pat. No. 10,353,429, which is a
(Continued)

(51) Int. Cl.
*G06F 1/16* (2006.01)
*G02C 7/16* (2006.01)
(Continued)

(52) U.S. Cl.
CPC ............ *G06F 1/163* (2013.01); *A61F 2/1613* (2013.01); *A61F 2/1627* (2013.01); *A61F 9/061* (2013.01);
(Continued)

(58) Field of Classification Search
CPC ............... G02B 27/01; G02B 27/0101; G02B 27/0149; G02B 27/017; G02B 27/0172;
(Continued)

(56) References Cited

U.S. PATENT DOCUMENTS

| 2,170,287 A | 8/1939 | Kinnebrew |
| 2,437,642 A | 3/1948 | Henroteau |

(Continued)

FOREIGN PATENT DOCUMENTS

| CN | 89113088 A | 10/2001 |
| CN | 19891013088 | 10/2001 |

(Continued)

OTHER PUBLICATIONS

Anderson, M. "Adaptive Optics: Liquid Crystals Lower the Cost of Adaptive Optics" Laser Focus World (Dec. 1999).
(Continued)

*Primary Examiner* — Robert E. Tallman
(74) *Attorney, Agent, or Firm* — Smith Baluch LLP

(57) ABSTRACT

Eyewear is provided including a frame, and a camera connected with the frame, in which the camera is configured to be controlled by a remote controller. The camera may be configured to capture video and/or a photo. The eyewear may include data storage, and the camera may be connected to the data storage. A wrist watch may be configured to act both as a time piece and a controller of the camera. The eyewear may also include a heads up display and/or a video file player. The eyewear may also include an electro-active lens.

24 Claims, 51 Drawing Sheets

Related U.S. Application Data continuation of application No. 15/613,733, filed on Jun. 5, 2017, now Pat. No. 10,159,563, which is a continuation of application No. 14/816,249, filed on Aug. 3, 2015, now Pat. No. 10,172,704, which is a continuation of application No. 13/779,320, filed on Feb. 27, 2013, now Pat. No. 9,124,796, which is a continuation of application No. 11/261,035, filed on Oct. 28, 2005, now Pat. No. 8,778,022.

(60) Provisional application No. 60/692,270, filed on Jun. 21, 2005, provisional application No. 60/687,341, filed on Jun. 6, 2005, provisional application No. 60/687,342, filed on Jun. 6, 2005, provisional application No. 60/685,407, filed on May 31, 2005, provisional application No. 60/679,241, filed on May 10, 2005, provisional application No. 60/674,702, filed on Apr. 26, 2005, provisional application No. 60/673,758, filed on Apr. 22, 2005, provisional application No. 60/669,403, filed on Apr. 8, 2005, provisional application No. 60/667,094, filed on Apr. 1, 2005, provisional application No. 60/666,167, filed on Mar. 30, 2005, provisional application No. 60/661,925, filed on Mar. 16, 2005, provisional application No. 60/659,431, filed on Mar. 9, 2005, provisional application No. 60/636,490, filed on Dec. 17, 2004, provisional application No. 60/623,947, filed on Nov. 2, 2004, provisional application No. 60/623,946, filed on Nov. 2, 2004.

(51) Int. Cl.
*G02C 11/00* (2006.01)
*G02C 7/08* (2006.01)
*A61F 2/16* (2006.01)
*G02C 7/06* (2006.01)
*A61F 9/06* (2006.01)
*H04N 5/232* (2006.01)
*H02J 50/10* (2016.01)
*G02C 7/10* (2006.01)
*H04N 5/225* (2006.01)

(52) U.S. Cl.
CPC ............ *G02C 7/06* (2013.01); *G02C 7/083* (2013.01); *G02C 7/101* (2013.01); *G02C 7/16* (2013.01); *G02C 11/10* (2013.01); *H02J 50/10* (2016.02); *H04N 5/2253* (2013.01); *H04N 5/23203* (2013.01); *H04N 5/23293* (2013.01)

(58) Field of Classification Search
CPC ............ G02B 27/0176; G02B 27/0179; G02C 5/001; G02C 9/00; G02C 9/02; G02C 9/04; G02C 11/00; G02C 11/10; G02C 11/12
USPC ....... 351/41, 51–52, 57–59; 359/13–14, 618, 359/629–633
See application file for complete search history.

(56) References Cited

U.S. PATENT DOCUMENTS

| | | |
|---|---|---|
| 2,576,581 A | 11/1951 | Edwards |
| 3,161,718 A | 12/1964 | De Luca |
| 3,183,523 A | 5/1965 | Harrison |
| 3,245,315 A | 4/1966 | Marks et al. |
| 3,248,460 A | 4/1966 | Naujokas |
| 3,309,162 A | 3/1967 | Kosanke et al. |
| 3,614,215 A | 10/1971 | Leo |
| 3,738,734 A | 6/1973 | Tait et al. |
| 3,791,719 A | 2/1974 | Kratzer et al. |
| 4,050,814 A | 9/1977 | Mcfadden |
| 4,062,629 A | 12/1977 | Winthrop |
| 4,174,156 A | 11/1979 | Glorieux |
| 4,181,408 A | 1/1980 | Senders |
| 4,190,330 A | 2/1980 | Berreman |
| 4,190,621 A | 2/1980 | Greshes |
| 4,257,691 A | 3/1981 | Brooks |
| 4,264,154 A | 4/1981 | Petersen |
| 4,279,474 A | 7/1981 | Belgorod |
| 4,300,818 A | 11/1981 | Schachar |
| 4,320,939 A | 3/1982 | Mueller |
| 4,373,218 A | 2/1983 | Schachar |
| 4,395,736 A | 7/1983 | Fraleux |
| 4,418,990 A | 12/1983 | Gerber |
| 4,423,929 A | 1/1984 | Gomi |
| 4,457,585 A | 7/1984 | Ducorday |
| 4,461,550 A | 7/1984 | Legendre |
| 4,466,703 A | 8/1984 | Nishimoto |
| 4,466,706 A | 8/1984 | Lamothe, II |
| 4,529,268 A | 7/1985 | Brown |
| 4,564,267 A | 1/1986 | Nishimoto |
| 4,572,616 A | 2/1986 | Kowel et al. |
| 4,577,928 A | 3/1986 | Brown |
| 4,601,545 A | 7/1986 | Kern |
| 4,609,824 A | 9/1986 | Munier et al. |
| 4,712,870 A | 12/1987 | Robinson et al. |
| 4,753,514 A | 6/1988 | Kubik |
| 4,756,605 A | 7/1988 | Okada et al. |
| 4,772,094 A | 9/1988 | Sheiman |
| D298,250 S | 10/1988 | Kildall |
| 4,781,440 A | 11/1988 | Toda |
| 4,787,733 A | 11/1988 | Silva |
| 4,787,903 A | 11/1988 | Grendahl |
| 4,795,248 A | 1/1989 | Okada et al. |
| 4,807,630 A | 2/1989 | Malinouskas |
| 4,813,777 A | 3/1989 | Rainville et al. |
| 4,816,031 A | 3/1989 | Pfoff |
| 4,818,095 A | 4/1989 | Takeuchi |
| 4,836,652 A | 6/1989 | Oishi et al. |
| 4,842,400 A | 6/1989 | Klein |
| 4,869,588 A | 9/1989 | Frieder et al. |
| 4,873,029 A | 10/1989 | Blum |
| 4,880,300 A | 11/1989 | Payner et al. |
| 4,890,903 A | 1/1990 | Treisman et al. |
| 4,904,063 A | 2/1990 | Okada et al. |
| 4,907,860 A | 3/1990 | Noble |
| 4,909,626 A | 3/1990 | Purvis et al. |
| 4,919,520 A | 4/1990 | Okada et al. |
| 4,921,728 A | 5/1990 | Takiguchi et al. |
| 4,927,241 A | 5/1990 | Kuijk |
| 4,929,865 A | 5/1990 | Blum |
| 4,930,884 A | 6/1990 | Tichenor et al. |
| 4,944,584 A | 7/1990 | Maeda et al. |
| 4,945,242 A | 7/1990 | Berger et al. |
| 4,952,048 A | 8/1990 | Frieder et al. |
| 4,952,788 A | 8/1990 | Berger et al. |
| 4,955,712 A | 9/1990 | Barth et al. |
| 4,958,907 A | 9/1990 | Davis |
| 4,961,639 A | 10/1990 | Lazarus |
| 4,968,127 A | 11/1990 | Russell et al. |
| 4,981,342 A | 1/1991 | Fiala |
| 4,991,951 A | 2/1991 | Mizuno et al. |
| 5,015,086 A | 5/1991 | Okaue et al. |
| 5,030,882 A | 7/1991 | Solero |
| 5,050,981 A | 9/1991 | Roffman |
| 5,066,301 A | 11/1991 | Wiley |
| 5,067,795 A | 11/1991 | Senatore |
| 5,073,021 A | 12/1991 | Marron |
| 5,076,665 A | 12/1991 | Petersen |
| 5,089,023 A | 2/1992 | Swanson |
| 5,091,801 A | 2/1992 | Ebstein |
| 5,108,169 A | 4/1992 | Mandell |
| 5,114,628 A | 5/1992 | Hoefer et al. |
| 5,122,974 A | 6/1992 | Chance |
| 5,130,856 A | 7/1992 | Tichenor et al. |
| 5,142,411 A | 8/1992 | Fiala |
| 5,147,585 A | 9/1992 | Blum |
| 5,150,234 A | 9/1992 | Takahashi et al. |
| 5,171,266 A | 12/1992 | Wiley et al. |

(56) References Cited

U.S. PATENT DOCUMENTS

| | | |
|---|---|---|
| 5,173,723 A | 12/1992 | Volk |
| 5,178,800 A | 1/1993 | Blum |
| 5,182,585 A | 1/1993 | Stoner |
| 5,184,156 A | 2/1993 | Black et al. |
| 5,200,859 A | 4/1993 | Payner et al. |
| 5,208,688 A | 5/1993 | Fergason et al. |
| 5,219,497 A | 6/1993 | Blum |
| 5,229,797 A | 7/1993 | Futhey et al. |
| 5,229,885 A | 7/1993 | Quaglia |
| 5,231,430 A | 7/1993 | Kohayakawa |
| 5,239,412 A | 8/1993 | Naka et al. |
| D342,063 S | 12/1993 | Howitt et al. |
| 5,299,053 A | 3/1994 | Kleinburg et al. |
| 5,305,028 A | 4/1994 | Okano |
| 5,306,926 A | 4/1994 | Yonemoto |
| 5,324,930 A | 6/1994 | Jech |
| D350,342 S | 9/1994 | Sack |
| 5,352,886 A | 10/1994 | Kane |
| 5,359,444 A | 10/1994 | Piosenka et al. |
| 5,375,006 A | 12/1994 | Haas |
| 5,382,986 A | 1/1995 | Black et al. |
| 5,386,308 A | 1/1995 | Michel et al. |
| 5,401,175 A | 3/1995 | Guimond et al. |
| 5,411,537 A | 5/1995 | Munshi et al. |
| 5,424,927 A | 6/1995 | Schaller et al. |
| 5,440,357 A | 8/1995 | Quaglia |
| 5,443,506 A | 8/1995 | Garabet |
| 5,451,766 A | 9/1995 | Van |
| 5,455,638 A | 10/1995 | Kallman et al. |
| 5,488,439 A | 1/1996 | Weltmann |
| 5,512,371 A | 4/1996 | Gupta et al. |
| 5,522,323 A | 6/1996 | Richard |
| 5,552,841 A | 9/1996 | Gallorini et al. |
| 5,585,871 A | 12/1996 | Linden |
| 5,606,743 A | 2/1997 | Vogt et al. |
| 5,608,567 A * | 3/1997 | Grupp ............... A61F 9/067 349/104 |
| 5,608,808 A | 3/1997 | Da |
| 5,615,588 A | 4/1997 | Gottschald |
| 5,653,751 A | 8/1997 | Samiy et al. |
| 5,654,786 A | 8/1997 | Gerald |
| 5,668,620 A | 9/1997 | Kurtin et al. |
| 5,682,223 A | 10/1997 | Menezes et al. |
| 5,683,457 A | 11/1997 | Gupta et al. |
| RE35,691 E | 12/1997 | Theirl et al. |
| 5,702,819 A | 12/1997 | Gupta et al. |
| 5,712,721 A | 1/1998 | Large |
| 5,715,337 A | 2/1998 | Spitzer et al. |
| 5,728,155 A | 3/1998 | Anello et al. |
| 5,739,959 A | 4/1998 | Quaglia |
| 5,757,458 A | 5/1998 | Miller et al. |
| 5,777,719 A | 7/1998 | Williams et al. |
| 5,815,233 A | 9/1998 | Morokawa et al. |
| 5,815,239 A | 9/1998 | Chapman et al. |
| 5,859,685 A | 1/1999 | Gupta et al. |
| 5,861,934 A | 1/1999 | Blum et al. |
| 5,861,936 A | 1/1999 | Sorensen |
| 5,877,876 A | 3/1999 | Birdwell |
| 5,886,822 A | 3/1999 | Spitzer |
| 5,900,720 A | 5/1999 | Kallman et al. |
| 5,903,395 A * | 5/1999 | Rallison ............ G02B 27/0172 345/8 |
| 5,905,561 A | 5/1999 | Lee et al. |
| 5,949,521 A | 9/1999 | Williams et al. |
| 5,953,098 A | 9/1999 | Lieberman et al. |
| 5,956,183 A | 9/1999 | Epstein et al. |
| 5,963,300 A | 10/1999 | Horwitz |
| 5,971,540 A | 10/1999 | Ofner |
| 5,980,037 A | 11/1999 | Conway |
| 5,988,816 A | 11/1999 | Quadri |
| 5,999,328 A | 12/1999 | Kurtin et al. |
| 6,007,363 A | 12/1999 | Renk |
| 6,023,372 A | 2/2000 | Spitzer et al. |
| 6,034,653 A | 3/2000 | Robertson et al. |
| 6,040,947 A | 3/2000 | Kurtin et al. |
| 6,050,687 A | 4/2000 | Bille et al. |
| 6,050,717 A | 4/2000 | Kosugi et al. |
| 6,069,742 A | 5/2000 | Silver |
| 6,086,203 A | 7/2000 | Blum et al. |
| 6,086,204 A | 7/2000 | Magnante |
| 6,091,546 A | 7/2000 | Spitzer |
| 6,091,832 A | 7/2000 | Shurman et al. |
| 6,095,651 A | 8/2000 | Williams et al. |
| 6,099,117 A | 8/2000 | Gregory |
| 6,115,177 A | 9/2000 | Vossler |
| 6,139,148 A | 10/2000 | Menezes |
| 6,145,987 A | 11/2000 | Baude et al. |
| 6,157,291 A | 12/2000 | Kuenster et al. |
| 6,165,123 A | 12/2000 | Thompson |
| 6,188,525 B1 | 2/2001 | Silver |
| 6,191,881 B1 | 2/2001 | Tajima |
| 6,199,984 B1 | 3/2001 | Menezes |
| 6,199,986 B1 | 3/2001 | Williams et al. |
| 6,204,974 B1 | 3/2001 | Spitzer |
| 6,213,602 B1 | 4/2001 | Smarto |
| 6,270,220 B1 | 8/2001 | Keren |
| 6,271,915 B1 | 8/2001 | Frey et al. |
| 6,282,449 B1 | 8/2001 | Kamerling et al. |
| 6,299,311 B1 | 10/2001 | Williams et al. |
| 6,305,802 B1 | 10/2001 | Roffman et al. |
| 6,324,053 B1 | 11/2001 | Kamijo |
| 6,325,508 B1 | 12/2001 | Decreton et al. |
| 6,338,559 B1 | 1/2002 | Williams et al. |
| 6,350,031 B1 | 2/2002 | Lashkari et al. |
| 6,390,623 B1 | 5/2002 | Kokonaski et al. |
| 6,396,622 B1 | 5/2002 | Alden |
| 6,437,762 B1 | 8/2002 | Birdwell |
| 6,437,925 B1 | 8/2002 | Nishioka |
| 6,464,363 B1 | 10/2002 | Nishioka et al. |
| 6,491,391 B1 | 12/2002 | Blum et al. |
| 6,491,394 B1 | 12/2002 | Blum et al. |
| 6,501,443 B1 | 12/2002 | Mcmahon |
| 6,517,203 B1 | 2/2003 | Blum et al. |
| 6,542,081 B2 | 4/2003 | Torch |
| 6,554,425 B1 | 4/2003 | Roffman et al. |
| 6,569,199 B1 | 5/2003 | Dotan et al. |
| 6,609,794 B2 | 8/2003 | Levine |
| 6,614,408 B1 | 9/2003 | Mann |
| 6,616,275 B1 | 9/2003 | Dick et al. |
| 6,616,279 B1 | 9/2003 | Davis et al. |
| 6,618,208 B1 | 9/2003 | Silver |
| 6,619,799 B1 | 9/2003 | Blum et al. |
| 6,626,532 B1 | 9/2003 | Nishioka et al. |
| 6,631,001 B2 | 10/2003 | Kuiseko |
| 6,638,304 B2 | 10/2003 | Azar |
| 6,643,552 B2 | 11/2003 | Edell et al. |
| 6,652,096 B1 | 11/2003 | Morris et al. |
| 6,667,471 B2 | 12/2003 | Bos et al. |
| 6,682,195 B2 | 1/2004 | Dreher |
| 6,705,729 B2 | 3/2004 | Piers et al. |
| 6,709,105 B2 | 3/2004 | Menezes |
| 6,709,107 B2 | 3/2004 | Jiang et al. |
| 6,709,108 B2 | 3/2004 | Levine et al. |
| 6,714,133 B2 | 3/2004 | Hum et al. |
| 6,733,130 B2 | 5/2004 | Blum et al. |
| 6,738,199 B2 | 5/2004 | Nishioka |
| 6,768,536 B2 | 7/2004 | Okuwaki et al. |
| 6,769,767 B2 | 8/2004 | Swab et al. |
| 6,774,871 B2 | 8/2004 | Birdwell |
| 6,778,246 B2 | 8/2004 | Sun et al. |
| 6,793,340 B1 | 9/2004 | Morris et al. |
| 6,830,193 B2 | 12/2004 | Tanaka |
| 6,833,938 B2 | 12/2004 | Nishioka |
| 6,840,619 B2 | 1/2005 | Dreher |
| 6,851,805 B2 | 2/2005 | Blum et al. |
| 6,857,741 B2 | 2/2005 | Blum et al. |
| 6,859,333 B1 | 2/2005 | Ren et al. |
| 6,871,951 B2 | 3/2005 | Blum et al. |
| 6,883,916 B2 | 4/2005 | Menezes |
| 6,886,938 B1 | 5/2005 | Menezes |
| 6,893,124 B1 | 5/2005 | Kurtin |
| 6,894,751 B2 | 5/2005 | Payne et al. |
| 6,902,271 B2 | 6/2005 | Perrott et al. |
| 6,918,570 B2 | 7/2005 | Ahn |

(56) References Cited

U.S. PATENT DOCUMENTS

| | | |
|---|---|---|
| 6,918,670 B2 | 7/2005 | Blum et al. |
| 6,948,818 B2 | 9/2005 | Williams et al. |
| 6,951,391 B2 | 10/2005 | Michael et al. |
| 6,955,433 B1 | 10/2005 | Benjamin et al. |
| 6,956,682 B2 | 10/2005 | Benjamin |
| 6,976,982 B2 | 12/2005 | Santini et al. |
| 6,986,579 B2 | 1/2006 | Blum et al. |
| 7,008,054 B1 | 3/2006 | Kurtin et al. |
| 7,009,757 B2 | 3/2006 | Nishioka et al. |
| 7,018,040 B2 | 3/2006 | Blum et al. |
| 7,019,890 B2 | 3/2006 | Meredith et al. |
| 7,023,594 B2 | 4/2006 | Blum et al. |
| 7,034,619 B2 | 4/2006 | Lynch |
| 7,041,133 B1 | 5/2006 | Azar |
| 7,077,519 B2 | 7/2006 | Blum et al. |
| 7,085,065 B2 | 8/2006 | Silver |
| 7,130,664 B1 | 10/2006 | Williams |
| 7,133,172 B2 | 11/2006 | Nishioka |
| 7,137,702 B2 | 11/2006 | Piers et al. |
| 7,137,952 B2 | 11/2006 | Leonardi et al. |
| 7,159,981 B2 | 1/2007 | Kato |
| 7,159,983 B2 | 1/2007 | Menezes et al. |
| 7,188,948 B2 | 3/2007 | Blum et al. |
| 7,192,136 B2 | 3/2007 | Howell et al. |
| 7,195,353 B2 | 3/2007 | Blum et al. |
| 7,209,097 B2 | 4/2007 | Suyama et al. |
| 7,229,173 B2 | 6/2007 | Menezes |
| 7,255,437 B2 | 8/2007 | Howell et al. |
| 7,290,876 B2 | 11/2007 | Duston et al. |
| 7,380,936 B2 | 6/2008 | Howell et al. |
| 7,396,126 B2 | 7/2008 | Blum et al. |
| 7,401,918 B2 | 7/2008 | Howell et al. |
| 7,404,636 B2 | 7/2008 | Blum et al. |
| 7,438,410 B1 | 10/2008 | Howell et al. |
| 7,461,936 B2 | 12/2008 | Jannard |
| 7,475,984 B2 | 1/2009 | Blum et al. |
| 7,481,531 B2 | 1/2009 | Howell et al. |
| 7,500,746 B1 | 3/2009 | Howell et al. |
| 7,500,747 B2 | 3/2009 | Howell et al. |
| 7,543,934 B2 | 6/2009 | Howell et al. |
| 7,581,833 B2 | 9/2009 | Howell et al. |
| 7,607,775 B2 | 10/2009 | Hermanson et al. |
| 7,621,634 B2 | 11/2009 | Howell et al. |
| 7,677,723 B2 | 3/2010 | Howell et al. |
| 7,760,898 B2 | 7/2010 | Howell et al. |
| 7,771,046 B2 | 8/2010 | Howell et al. |
| 7,792,552 B2 | 9/2010 | D et al. |
| 7,806,525 B2 | 10/2010 | Howell et al. |
| 7,831,055 B2 | 11/2010 | Frerking et al. |
| 7,922,321 B2 | 4/2011 | Howell et al. |
| 7,988,283 B2 | 8/2011 | Jannard |
| 8,025,396 B1 | 9/2011 | Power |
| 8,089,511 B2 | 1/2012 | Yamamoto |
| 8,109,629 B2 | 2/2012 | Howell et al. |
| 8,174,569 B2 | 5/2012 | Tanijiri et al. |
| 8,337,013 B2 | 12/2012 | Howell et al. |
| 8,337,014 B2 | 12/2012 | Kokonaski et al. |
| 8,430,507 B2 | 4/2013 | Howell et al. |
| 8,434,863 B2 | 5/2013 | Howell et al. |
| 8,465,151 B2 | 6/2013 | Howell et al. |
| 8,500,271 B2 | 8/2013 | Howell et al. |
| 8,708,483 B2 | 4/2014 | Kokonaski et al. |
| 8,770,742 B2 | 7/2014 | Howell et al. |
| 8,905,541 B2 | 12/2014 | Blum et al. |
| 8,915,588 B2 | 12/2014 | Blum et al. |
| 8,931,896 B2 | 1/2015 | Blum et al. |
| 9,122,083 B2 | 9/2015 | Blum et al. |
| 9,124,796 B2 | 9/2015 | Blum et al. |
| 10,092,395 B2 | 10/2018 | Blum et al. |
| 10,114,235 B2 | 10/2018 | Blum et al. |
| 10,159,563 B2 | 12/2018 | Blum et al. |
| 10,379,575 B2 | 8/2019 | Blum et al. |
| 2001/0005230 A1 | 6/2001 | Ishikawa |
| 2001/0055094 A1 | 12/2001 | Zhang |
| 2002/0049374 A1 | 4/2002 | Abreu |
| 2002/0060525 A1 | 5/2002 | Sagano et al. |
| 2002/0101568 A1* | 8/2002 | Eberl .................. G02B 27/017 351/211 |
| 2002/0140899 A1 | 10/2002 | Blum et al. |
| 2002/0149739 A1 | 10/2002 | Perrott et al. |
| 2002/0186346 A1 | 12/2002 | Stantz et al. |
| 2003/0004546 A1 | 1/2003 | Casey |
| 2003/0018383 A1 | 1/2003 | Azar |
| 2003/0067585 A1 | 4/2003 | Miller et al. |
| 2003/0086052 A1* | 5/2003 | Zelman .................. G02C 1/04 351/47 |
| 2003/0103413 A1 | 6/2003 | Jacobi et al. |
| 2003/0112523 A1 | 6/2003 | Daniell |
| 2003/0151721 A1 | 8/2003 | Lai et al. |
| 2003/0199978 A1 | 10/2003 | Lindsey et al. |
| 2003/0208265 A1 | 11/2003 | Ho et al. |
| 2003/0210377 A1 | 11/2003 | Blum et al. |
| 2004/0000733 A1 | 1/2004 | Swab et al. |
| 2004/0008157 A1 | 1/2004 | Brubaker et al. |
| 2004/0008319 A1 | 1/2004 | Lai et al. |
| 2004/0010310 A1 | 1/2004 | Peyman |
| 2004/0108971 A1 | 6/2004 | Waldern et al. |
| 2004/0117011 A1 | 6/2004 | Aharoni et al. |
| 2004/0130677 A1 | 7/2004 | Liang et al. |
| 2004/0160573 A1 | 8/2004 | Jannard et al. |
| 2004/0179280 A1 | 9/2004 | Nishioka |
| 2004/0186533 A1 | 9/2004 | Greenberg et al. |
| 2004/0196435 A1 | 10/2004 | Dick et al. |
| 2004/0239874 A1 | 12/2004 | Swab et al. |
| 2004/0246440 A1 | 12/2004 | Andino et al. |
| 2005/0049578 A1 | 3/2005 | Tu et al. |
| 2005/0073739 A1 | 4/2005 | Meredith et al. |
| 2005/0078274 A1 | 4/2005 | Howell et al. |
| 2005/0099594 A1 | 5/2005 | Blum et al. |
| 2005/0113912 A1 | 5/2005 | Feenstra et al. |
| 2005/0124983 A1 | 6/2005 | Frey et al. |
| 2005/0237485 A1 | 10/2005 | Blum et al. |
| 2005/0256571 A1 | 11/2005 | Azar |
| 2006/0044510 A1 | 3/2006 | Williams et al. |
| 2006/0066808 A1 | 3/2006 | Blum et al. |
| 2006/0095128 A1 | 5/2006 | Blum et al. |
| 2006/0113054 A1 | 6/2006 | Silvestrini |
| 2006/0122531 A1 | 6/2006 | Goodall et al. |
| 2006/0164593 A1 | 7/2006 | Peyghambarian et al. |
| 2006/0173367 A1 | 8/2006 | Stuart et al. |
| 2006/0177086 A1 | 8/2006 | Rye et al. |
| 2006/0183986 A1 | 8/2006 | Rice et al. |
| 2007/0030442 A1 | 2/2007 | Howell et al. |
| 2008/0143954 A1 | 6/2008 | Abreu et al. |
| 2008/0218684 A1 | 9/2008 | Howell et al. |
| 2009/0256977 A1 | 10/2009 | Haddock et al. |
| 2009/0296044 A1 | 12/2009 | Howell et al. |
| 2010/0103076 A1 | 4/2010 | Yamamoto |
| 2010/0177277 A1 | 7/2010 | Kokonaski et al. |
| 2010/0292599 A1 | 11/2010 | Oleson et al. |
| 2011/0071459 A1 | 3/2011 | Rickard et al. |
| 2011/0249230 A1 | 10/2011 | Blum |
| 2013/0215374 A1 | 8/2013 | Blum et al. |
| 2013/0235332 A1 | 9/2013 | Blum et al. |
| 2013/0242253 A1 | 9/2013 | Blum et al. |
| 2013/0250135 A1 | 9/2013 | Blum et al. |
| 2013/0250233 A1 | 9/2013 | Blum et al. |
| 2015/0335420 A1 | 11/2015 | Blum et al. |
| 2015/0378180 A1 | 12/2015 | Blum et al. |
| 2017/0176777 A1 | 6/2017 | Blum et al. |
| 2018/0221137 A1 | 8/2018 | Blum et al. |
| 2018/0329234 A1 | 11/2018 | Blum et al. |
| 2019/0110887 A1 | 4/2019 | Blum et al. |

FOREIGN PATENT DOCUMENTS

| | | |
|---|---|---|
| CN | 2911723 Y | 6/2007 |
| CN | 201222131 Y | 4/2009 |
| CN | 201464741 U | 5/2010 |
| DE | 4223395 A1 | 1/1994 |
| EP | 0154962 A2 | 9/1985 |
| EP | 0233104 A1 | 8/1987 |
| EP | 0237365 A1 | 9/1987 |
| EP | 0578833 A1 | 1/1994 |

(56) References Cited

FOREIGN PATENT DOCUMENTS

| | | |
|---|---|---|
| EP | 0649044 A1 | 4/1995 |
| EP | 0918248 A2 | 5/1999 |
| GB | 2169417 A | 7/1986 |
| GB | 2170613 A | 8/1986 |
| HK | 1122719 A | 5/2009 |
| JP | S5576323 A | 6/1980 |
| JP | S58113912 A | 7/1983 |
| JP | S61156227 A | 7/1986 |
| JP | S61502221 A | 10/1986 |
| JP | S6357044 A | 3/1988 |
| JP | H01237610 A | 9/1989 |
| JP | H0423579 A | 1/1992 |
| JP | H0461495 A | 2/1992 |
| JP | H05100201 A | 4/1993 |
| JP | H0728002 A | 1/1995 |
| JP | H08508826 A | 9/1996 |
| JP | H11352445 A | 12/1999 |
| JP | 2001252346 A | 9/2001 |
| JP | 2001522063 A | 11/2001 |
| JP | 2002533158 A | 10/2002 |
| JP | 2003230590 A | 8/2003 |
| JP | 2000138858 A | 9/2007 |
| JP | 2007323062 A | 12/2007 |
| JP | 2008545287 A | 12/2008 |
| JP | 2011229024 A | 11/2011 |
| WO | 8505466 A1 | 12/1985 |
| WO | 9423334 A1 | 10/1994 |
| WO | 9425510 A1 | 11/1994 |
| WO | 9923524 A1 | 5/1999 |
| WO | 0038593 A1 | 7/2000 |
| WO | 0106298 A1 | 1/2001 |
| WO | 02057836 A1 | 7/2002 |
| WO | 03007851 A1 | 1/2003 |
| WO | 03050472 A1 | 6/2003 |
| WO | 03068059 A2 | 8/2003 |
| WO | 2004008189 A1 | 1/2004 |
| WO | 2004015460 A2 | 2/2004 |
| WO | 2004015481 A1 | 2/2004 |
| WO | 2004034095 A2 | 4/2004 |
| WO | 2004072687 A2 | 8/2004 |
| WO | 2006120416 A1 | 11/2006 |
| WO | 2010080999 A1 | 7/2010 |

OTHER PUBLICATIONS

Bertsch, A. et al., "The Sensing Contact Lens", Medical Device Technology (2006); 17: 19-21.

Bradley, Arthur "Profile: Larry N. Thibos, PhD., and Donald T. Miller, PhD." Indiana Journal of Optometry; 2:I (Spring 1999).

Danfield, C., Phakic Intraocular Lens Implant, WordcatTop Quality Articles, 2 pages, Retrieved from the Internet on Nov. 20, 2008: http://www.wordcat.co.uk/articles/phakic-intraocular-lens-implant/279/.

Davis, Robert A. "Computer Vision Syndrome—The Eyestrain Epidemic" Review of Optometry (Sep. 15, 1997).

Donald T. Miller, Xin Hong, and Larry N. Thibos, "Requirements for the segmented spatial light modulators for diffraction-limited imaging through aberrated eyes," G.D. Love, ed. Proceedings of the 2nd International Workshop on Adaptive Optics for Industry and Medicine, World Scientific, Singapore, 63-68 (Jul. 1999).

Eggers, T. et al., "Wireless Intra-ocular Pressure Monitoring System Integrated in an Artificial Lens", Presented at the First Annual International IEEE-EMBS Special Topic Conference on Microtechnologies in Medicine & Biology, Lyon, France, Oct. 12-14, 2000; Paper 7: 466-469.

Eyecare Business (Oct. 1997).

International Preliminary Report on Patentabiity for Application No. PCT/US2005/039101 dated May 8, 2007.

International Preliminary Report on Patentability for PCT/US2009/044168 dated Nov. 17, 2010.

International Search Report corresponding to the PCT/US09/037544 application dated May 20, 2009.

International Search Report for Application No. PCT/US 08/54721 dated Aug. 20, 2008.

International Search Report for Application No. PCT/US2005/039101 dated Jul. 7, 2006.

International Search Report for application PCT/US 08/54721 dated Aug. 20, 2008.

International Search Report for PCT/US2009/044168 dated Oct. 7, 2009.

International Search Report of Application No. PCT/US08/51649 dated Jul. 7, 2008.

Kowel, Stephen T., et al "Focusing by electrical modulation of refraction in a liquid crystal cell" Applied Optics23:2 (Jan. 15, 1984).

Lazarus, Stuart M. "The Use of Yoked Base-Up and Base-In Prism for Reducing Eye Strain at the Computer" Journal of the American Optometric Association (Apr. 1996).

Leonardi, M. et al., "A Soft Contact Lens with a MEMS Strain Gage Embedded for Intraocular Pressure Monitoring", Transducers '03; The 12th International Conference on Solid Slate Sensors, Actuators and Microsyslems, Boston, Jun. 8-12, 2003; 362.5: 1043-1046.

Leonardi, M. et al., "First Steps toward Noninvasive IOP— Monitoring with a Sensing Contact Lens", Investigative Ophthalmology & Visual Science (2004); 45(9): 3113-3117.

Machine English Translation of JP2000-138858 (May 16, 2000).

Miller, Donald T. et al. "Requirements for the segmented spatial light modulators for diffraction-limited imaging through aberrated eyes," G.D. Love, ed. Proceedings of the 2nd International Workshop on Adaptive Optics for Industry and Medicine, World Scientific, Singapore, 63-68 (Jul. 1999).

Naumov, A.F. "Control Optimization of Spherical Modal Liquid Crystal Lenses", Optics Express 4:9; Optical Society of America (Apr. 26, 1999).

Naumov, A.F. "Liquid Crystal Adaptive Lenses with Modal Control" Optics Letters, 23:13 Optical Society of America (Jul. 1, 1998).

Optics, Org, Dec. 19, 2006 "Liquid Lenses Eye Commercial Breakthrough" Opto & Laser Europe (Nov. 2003).

Pitchon, E.M. et al., "First In-Vivo Human Monitoring of Intraocular Pressure Fluctuation and Ocular Pulsation by a Wireless Soft Contact Lens Sensor." Congress of the European Glaucoma Society, Berlin, Jun. 2008; Congres annuel de la Societe francaise d'ophtalmologie, Paris, May 2008; ARVO Meeting (The Association for Research in Vision and Ophthalmology), Apr. 27-May 1, 2008, Fort Lauderdale American Glaucoma Society, 18th Annual Meeting, Mar. 2008, Washington, 1 page.

Supplementary European Search Report of Application No. EP 05824718 dated Nov. 19, 2007.

Tarascon et al., "Issues and challenges facing rechargeable lithium batteries" Nature 2001, 414:359-367 (Nov. 15, 2001).

Thibos, Larry N., et al. "Vision through a liquid-crystal spatial light modulator" Adaptive Optics Conference; Durham, UK (1999).

Thibos, Larry N., et. al. "Use of Liquid-Crystal Adaptive-Optics to Alter the Refractive State of the Eye; Optometry and Vision Science" 74:7; American Academy of Optometry (Jul. 1997).

Thibos, Larry, N., et al. "Electronic Spectacles for the 21 Century" Indian Journal of Optometry, 2:1 (Spring 1999).

Walter, P. et al., "Development of a completely encapsulated intraocular pressure sensor", Ophthalmic Research (2000); 32: 278-284.

* cited by examiner

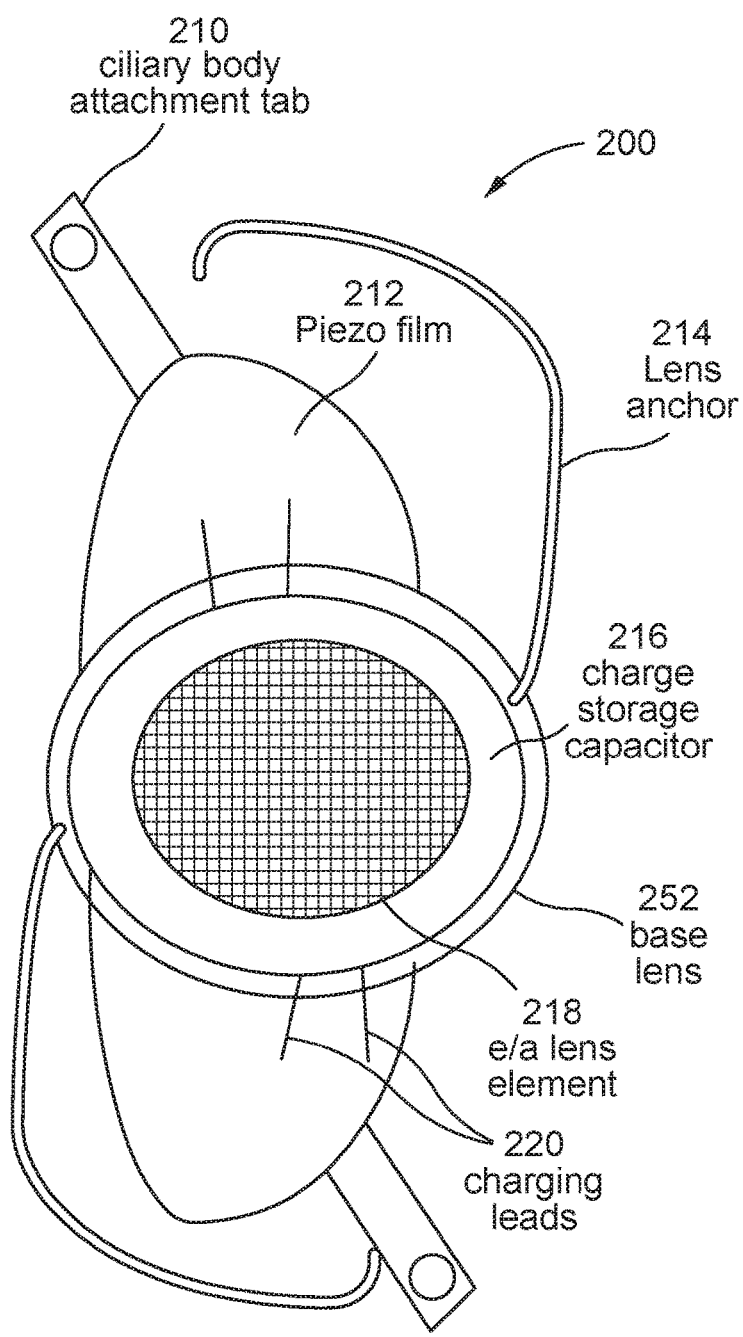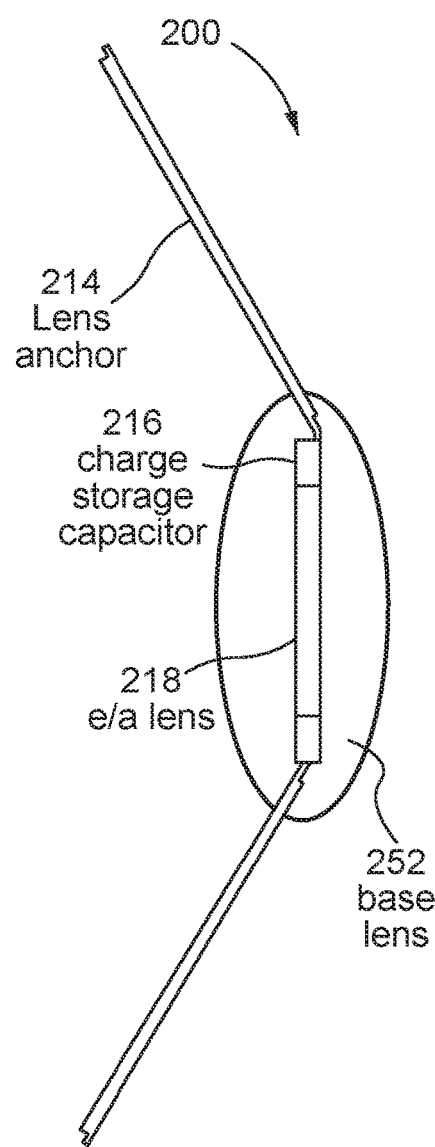
Figure 2A
Figure 2B

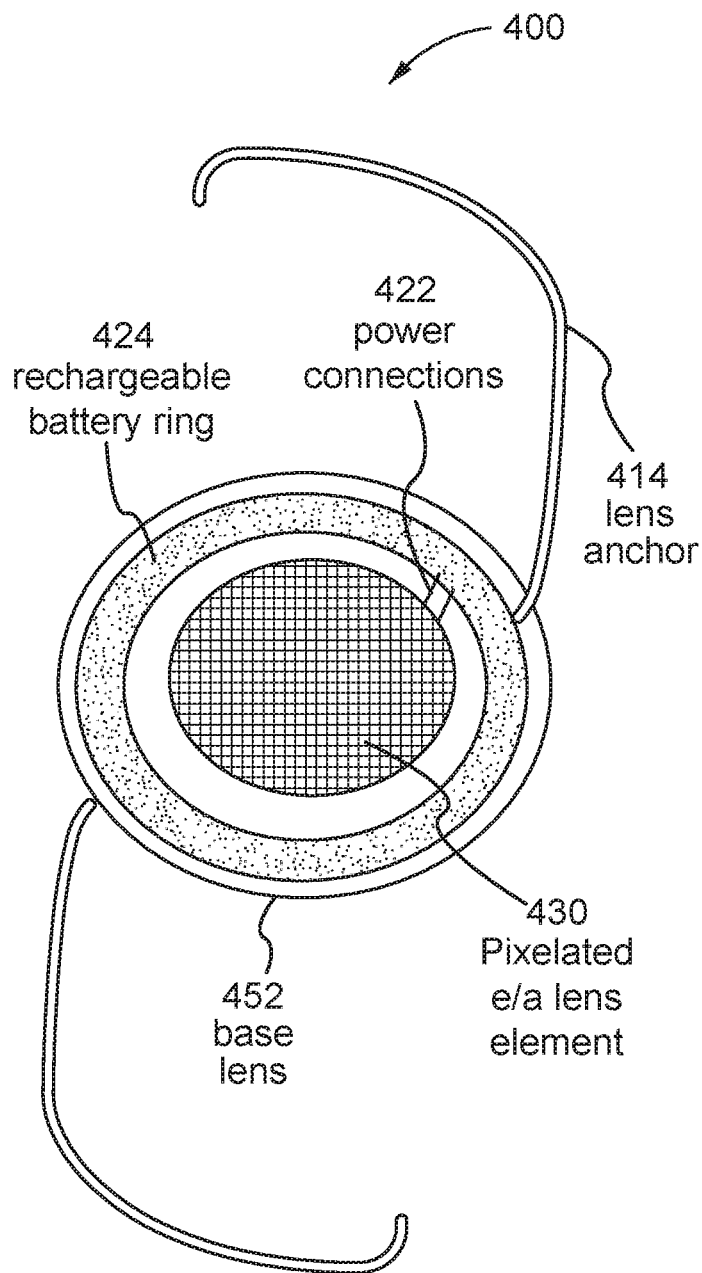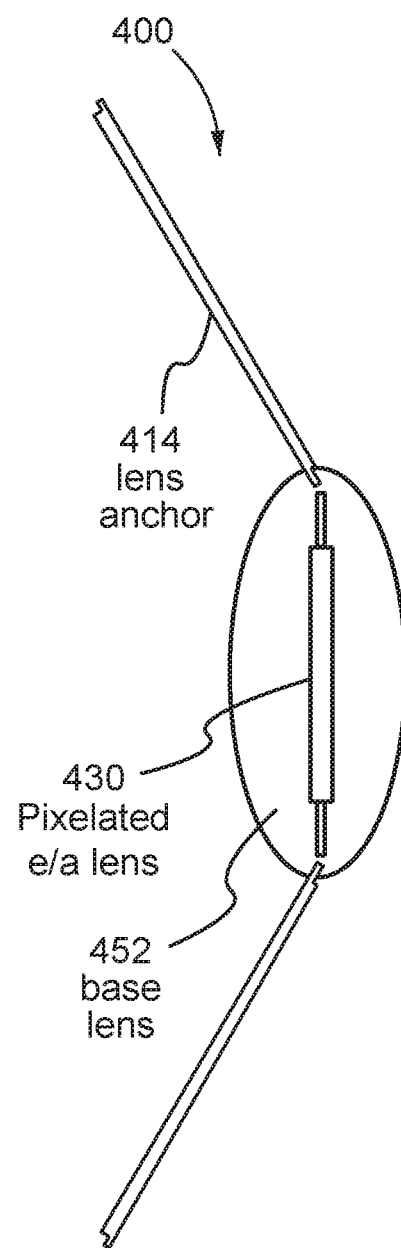
Figure 4A
Figure 4B

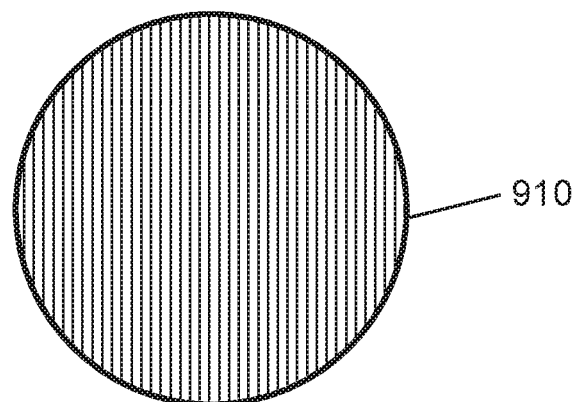
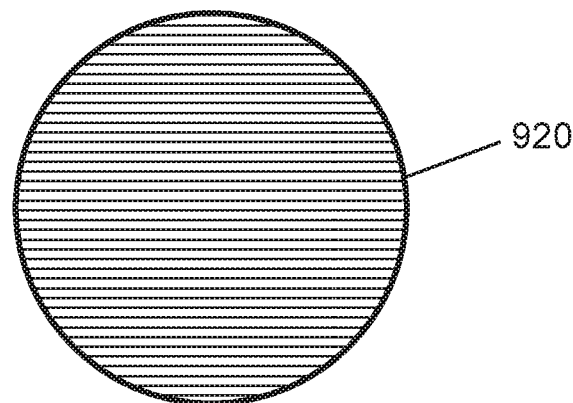
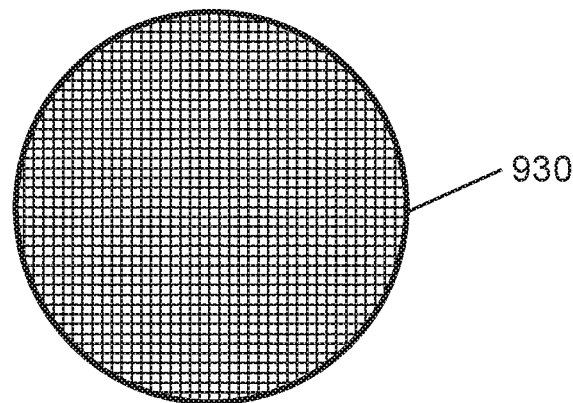
Figure 9

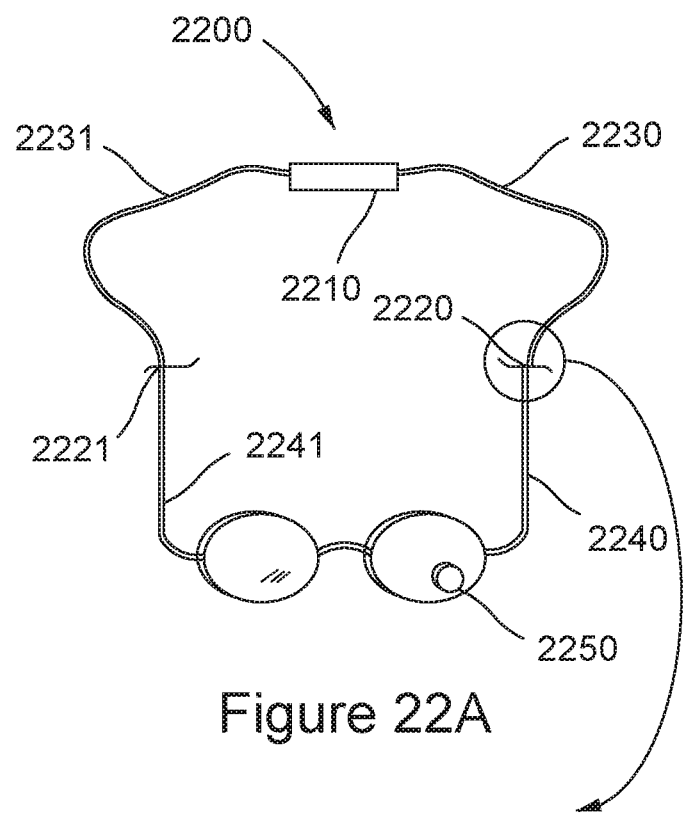
Figure 22A
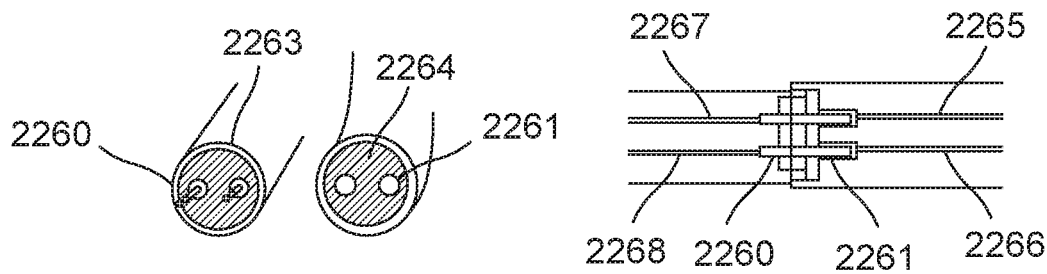
Figure 22B
Figure 22C
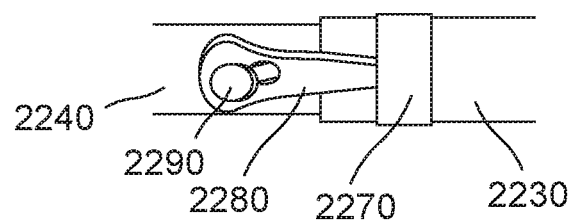
Figure 22D

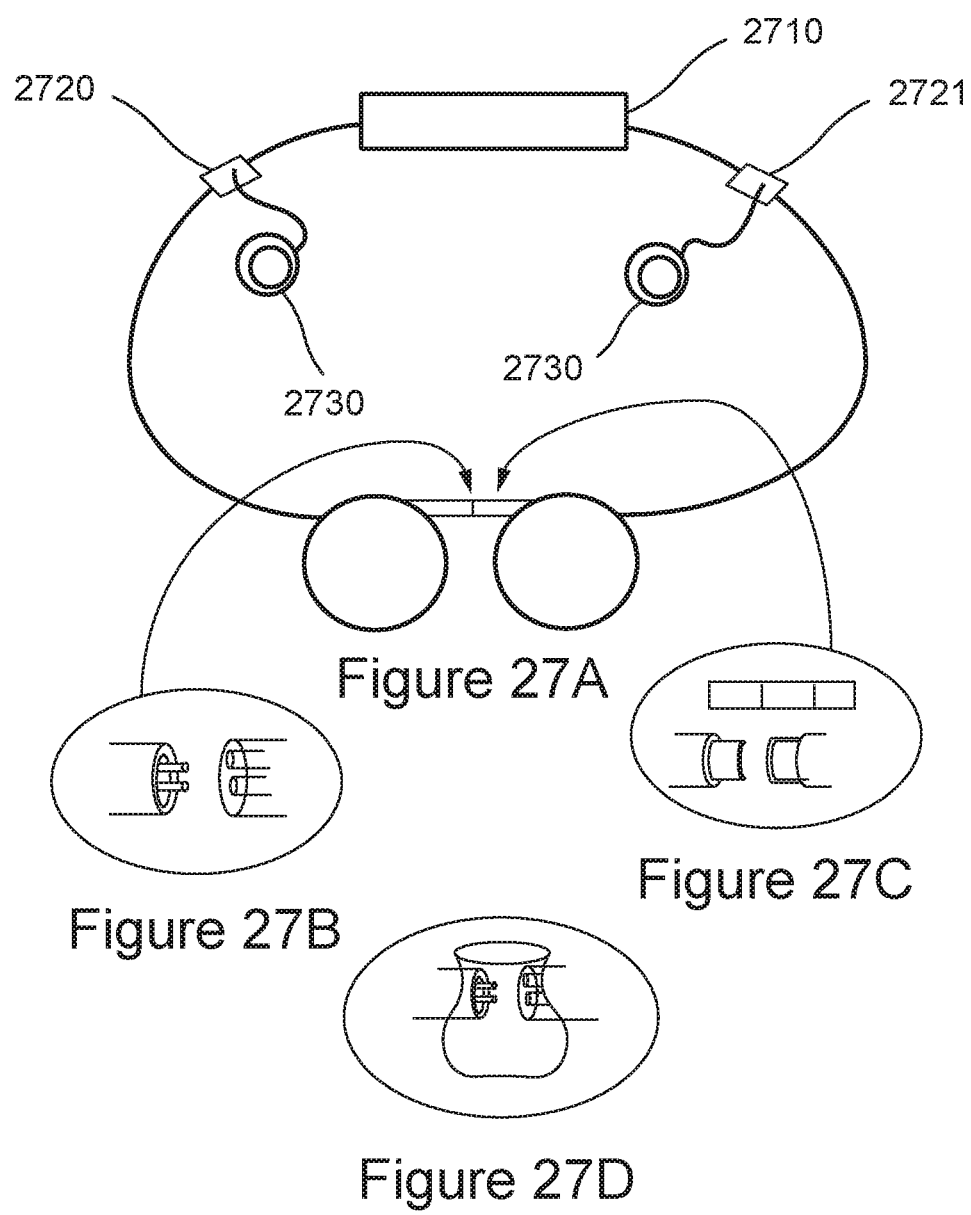

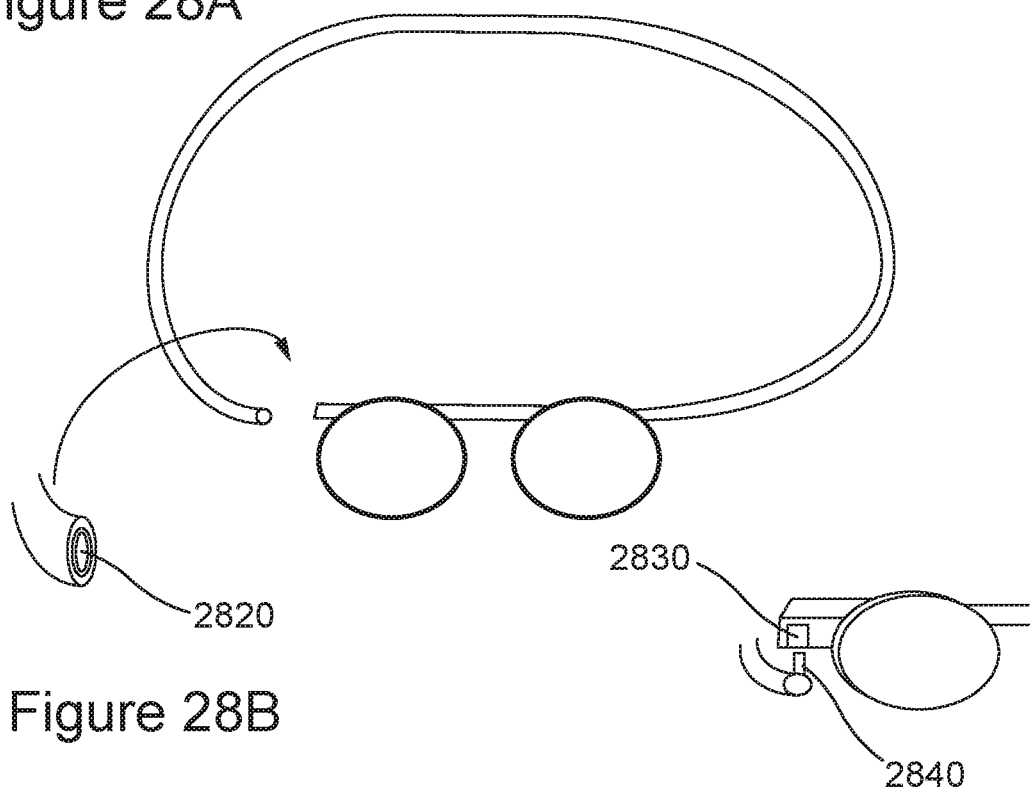

EYEWEAR INCLUDING A REMOTE CONTROL CAMERA AND A DOCKING STATION

RELATED PATENTS AND APPLICATIONS

This application is a continuation of U.S. application Ser. No. 15/920,634, filed Mar. 14, 2019, which is a continuation of U.S. application Ser. No. 15/613,733, filed May 6, 2017, now U.S. Pat. No. 10,159,563, which is a continuation of Ser. No. 14/816,249, filed Aug. 3, 2015, now U.S. Pat. No. 10,172,704, which is a is continuation of U.S. application Ser. No. 13/779,320, filed on Feb. 27, 2013, now U.S. Pat. No. 9,124,796, which is a continuation of U.S. application Ser. No. 11/261,035, filed Oct. 28, 2005, now U.S. Pat. No. 8,778,022, which claims the benefit of the following provisional applications: U.S. Provisional Application No. 60/692,270 filed Jun. 21, 2005; U.S. Provisional Application No. 60/687,341 filed Jun. 6, 2005; U.S. Provisional Application No. 60/687,342 filed Jun. 6, 2005; U.S. Provisional Application No. 60/685,407 filed May 31, 2005; U.S. Provisional Application No. 60/679,241 filed May 10, 2005; U.S. Provisional Application No. 60/674,702 filed Apr. 26, 2005; U.S. Provisional Application No. 60/673,758 filed Apr. 22, 2005; U.S. Provisional Application No. 60/669,403 filed Apr. 8, 2005; U.S. Provisional Application No. 60/667,094 filed Apr. 1, 2005; U.S. Provisional Application No. 60/666,167 filed Mar. 30, 2005; U.S. Provisional Application No. 60/661,925 filed Mar. 16, 2005; U.S. Provisional Application No. 60/659,431 filed Mar. 9, 2005; U.S. Provisional Application No. 60/623,947 filed Nov. 2, 2004; U.S. Provisional Application No. 60/623,946 filed Nov. 2, 2004; and U.S. Provisional Application No. 60/636,490 filed Dec. 17, 2004, all of which are hereby incorporated in their entireties by reference.

The following applications, provisional applications, and patents are incorporated by reference in their entirety: U.S. application Ser. No. 11/232,551 filed Sep. 22, 2005; U.S. Pat. No. 6,918,670 issued Jul. 19, 2005; U.S. application Ser. No. 11/183,454 filed Jul. 18, 2005; U.S. Provisional Application No. 60/692,270 filed Jul. 21, 2005; U.S. Provisional Application No. 60/687,342 filed Jun. 6, 2005; U.S. Provisional Application No. 60/687,341 filed Jun. 6, 2005; U.S. Provisional Application No. 60/685,407 filed May 31, 2005; U.S. Provisional Application No. 60/679,241 filed May 10, 2005; U.S. Provisional Application No. 60/674,702 filed Apr. 26, 2005; U.S. Provisional Application No. 60/673,758 filed Apr. 22, 2005; U.S. application Ser. No. 11/109,360 filed Apr. 19, 2005; U.S. Provisional Application No. 60/669,403 filed Apr. 8, 2005; U.S. Provisional Application No. 60/667,094 filed Apr. 1, 2005; U.S. Provisional Application No. 60/666,167 filed Mar. 30, 2005; U.S. Pat. No. 6,871,951 issued Mar. 29, 2005; U.S. application Ser. No. 11/091,104 filed Mar. 28, 2005; U.S. Provisional Application No. 60/661,925 filed Mar. 16, 2005; U.S. Provisional Application No. 60/659,431 filed Mar. 9, 2005; U.S. application Ser. No. 11/063,323 filed Feb. 22, 2005; U.S. Pat. No. 6,857,741 issued Feb. 22, 2005; U.S. Pat. No. 6,851,805 issued Feb. 8, 2005; U.S. application Ser. No. 11/036,501 filed Jan. 14, 2005; U.S. application Ser. No. 11/030,690 filed Jan. 6, 2005; U.S. application Ser. No. 10/996,781 filed Nov. 24, 2004; U.S. Provisional Application No. 60/623,947 filed Nov. 2, 2004; U.S. application Ser. No. 10/924,619 filed Aug. 24, 2004; U.S. application Ser. No. 10/918,496 filed Aug. 13, 2004; U.S. application Ser. No. 10/863,949 filed Jun. 9, 2004; U.S. Pat. No. 6,733,130 issued May 11, 2004; U.S. application Ser. No. 10/772,917 filed Feb. 5, 2004; U.S. Pat. No. 6,619,799 issued Sep. 16, 2003; U.S. application Ser. No. 10/664,112 filed Aug. 20, 2003; U.S. application Ser. No. 10/627,828 filed Jul. 25, 2003; U.S. application Ser. No. 10/387,143 filed Mar. 12, 2003; U.S. Pat. No. 6,517,203 issued Feb. 11, 2003; U.S. Pat. No. 6,491,391 issue Dec. 10, 2002; U.S. Pat. No. 6,491,394 issued Dec. 10, 2002; and U.S. application Ser. No. 10/263,707 filed Oct. 4, 2002.

BACKGROUND

The present invention relates to field of Intraocular Lenses (IOLs). In particular, the present invention relates to Intraocular Lenses wherein an electro-active element provides at least a portion of the IOL's refractive power, or prismatic power, or at least a portion of the tinting.

Intraocular lenses (IOLs) are typically permanent, plastic lenses that are surgically implanted inside of the eyeball to replace or supplement the eye's natural crystalline lens. They have been used in the United States since the late 1960s to restore vision to cataract patients, and more recently are being used in several types of refractive eye surgery.

The natural crystalline lens is critical component of the complex optical system of the eye. The crystalline lens provides about 17 diopters of the total 60 diopters of the refractive power of a healthy eye. Further, a healthy crystalline lens provides adjustable focusing when deformed by the muscular ciliary body that circumferentially surrounds the crystalline lens. As the eye ages, the flexibility of the crystalline lens decreases and this adjustable focusing is diminished. Thus, this critical crystalline lens almost invariably loses flexibility with age, and often loses transparency with age due to cataracts or other diseases.

Most intraocular lenses used in cataract surgery may be folded and inserted through the same tiny opening that was used to remove the natural crystalline lens. Once in the eye, the lens may unfold to its full size. The opening in the eye is so small that it heals itself quickly without stitches. The intraocular lenses may be made of inert materials that do not trigger rejection responses by the body.

In most cases, IOLs are permanent. They rarely need replacement, except in the instances where the measurements of the eye prior to surgery have not accurately determined the required focusing power of the IOL. Also, the surgery itself may change the optical characteristics of the eye. In most cases, the intraocular lenses implanted during cataract surgery are monofocal lenses, and the optical power of the IOL is selected such that the power of the eye is set for distance vision. Therefore, in most cases the patient will still require reading glasses after surgery. Intraocular lens implants may be static multifocal lenses, which attempt to function more like the eye's natural lens by providing clear vision at a distance and reasonable focus for a range of near distances, for patients with presbyopia. Not all patients are good candidates for the multifocal lens; however, those who can use the lens are some what pleased with the results.

More recently, accommodative IOLs have been introduced. These accommodative IOLs actually change focus by movement (physically deforming and/or translating within the orbit of the eye) as the muscular ciliary body reacts to an accommodative stimulus from the brain, similar to the way the natural crystalline lens focuses. While these offer promise, accommodative IOLs still have not been perfected. In spite of these limited successes, the multi-focal IOL and present accommodative IOLs still have a substantial decrease in performance when compared to a healthy natural crystalline lens.

Another ocular lens that holds promise for correcting presbyopia is the Small Diameter Corneal Inlay (SDCI). The Small Diameter Corneal Inlay (SDCI) is a prescription lens that is inserted into the corneal tissue to create an effect similar to a bifocal contact lens. Corneal Inlays (SDCI) are early in their development and it is still too early to understand how well they will function and also how effective they will become.

While all these emerging surgical procedures have their merits, they all have a substantial decrease in performance when compared to a young healthy natural crystalline lens. The present invention addresses these shortcomings by providing an intraocular lens that behaves in a manner similar to the natural crystalline lens.

Over the past decade, the miniaturization of semiconductor chips, sophisticated earphones, non-volatile solid-state memory, and wireless communication (including blue tooth, and other short-range wireless technologies) have ushered in a revolution in personal electronic components and audio listening devices that allows wearers to listen to music in a portable, hands-free manner. In addition, recent research and development has resulted in the development of accessories and features for eyeglasses such as, by way of example only: electro-active spectacle lenses which provide the wearer with variable focus capability, electro-active spectacle lenses that allow for a varying index matrix needed to correct higher order aberrations to create a supervision effect, electronic heads up displays that are associated with eye glasses, electrochromic lenses that change color and tint by way of electrical activation, and also the addition of audio and communication systems that are associated with eyeglasses. These new electronic eyeglass applications have created a significant need for a convenient, comfortable and aesthetically pleasing way to provide power to the eyeglass frame and lenses. More and more, the eyeglass frame is becoming a platform for associating and housing various electronic accessories.

Currently, there is no known way to electrify the eyeglass frame in a manner that provides a combination of pleasing aesthetics, comfort, convenience, and also allows for the proper ergonomics. While comfort, convenience and ergonomics are important, the proper fashion look of the eyeglass frame is what takes priority when the consumer makes a purchase decision. If the eyeglass frame is thicker or more bulky looking than normal, then the purchase decision can be impacted in a negative manner. In addition, if the eyeglass frame is heavier than normal, red inflamed sore spots will occur on either side of the bridge of one's nose or the top of the ears. In the case of active work or sports, such as, by way of example only, construction work, running, biking, walking, rowing, and horseback riding, the heavier eyeglass frames are, the more prone they are to slide down ones nose, and thus the alignment of the lens optics will not be optimal.

SUMMARY

An illustrative aspect of the invention provides an intraocular lens system comprising an electro-active lens comprising multiple independently controllable zones or pixels, and a controller capable of being remotely programmed.

The present subject matter provides an inventive solution, which addresses and corrects this pressing need. The invention does this in a manner that is allows for the eyeglass frames to continue to appear like conventional fashionable eye glass frames whether they be dress glasses, sport glasses or goggles, security glasses or goggles, sunglasses or goggles. It also takes the added weight of the power source off of the eyeglass frame and places this weight were it is barely noticed if at all. Finally, it provides for doing this in a most ergonomic and convenient manner.

According to first aspects of the invention, eyewear comprising an electronic docking station may be provided, whereby the docking station provides power to a docked electrical component.

According to further aspects of the invention, eyewear comprising a camera may be provided, whereby the camera is controlled by a remote controller.

According to further aspects of the invention, eyewear comprising a heads up display may be provided, wherein the heads up display is housed in a visor affixed to the eyewear.

Other aspects of the invention will become apparent from the following descriptions taken in conjunction with the following drawings, although variations and modifications may be effected without departing from the spirit and scope of the novel concepts of the disclosure.

BRIEF DESCRIPTION

The present invention can be more fully understood by reading the following detailed description together with the accompanying drawings, in which like reference indicators are used to designate like elements.

FIG. 1 displays the major anatomical components of a human eye.

FIG. 2A displays a front view of an intraocular lens embodiment with an electro-active lens and piezoelectric material as a power supply.

FIG. 2B displays a side view of an intraocular lens embodiment with an electro-active lens and piezoelectric material as a power supply.

FIG. 3A displays a front view of an intraocular lens embodiment with a diffractive electro-active lens and a rechargeable battery ring.

FIG. 3B displays a side view of an intraocular lens embodiment with a diffractive electro-active lens and a rechargeable battery ring.

FIG. 4A displays a front view of an intraocular lens embodiment with a pixelated electro-active lens and a rechargeable battery ring.

FIG. 4B displays a side view of an intraocular lens embodiment with a pixelated electro-active lens and a rechargeable battery ring.

FIG. 5 displays an external power supply embodiment with inductive charging elements inside of a pillow.

FIG. 6 displays an intraocular lens embodiment with an electro-active lens and a control chip with an antenna for use with a wireless programming unit.

FIG. 9 illustrates the stacking of two prismatic lenses with linear electrodes to produce any combination of vertical and horizontal displacement of an image on the retina

FIGS. 22A-22D illustrate another exemplary eyewear system according to further aspects of the invention.

FIGS. 27A-27D illustrate another exemplary eyewear system, including an electrical tether containing audio signals from a music player, according to further aspects of the invention.

FIGS. 28A-28C illustrates alternative configurations for breaking connections of eyewear such as shown in FIGS. 27A-27D, according to further aspects of the invention.

DETAILED DESCRIPTION

Figure 1:
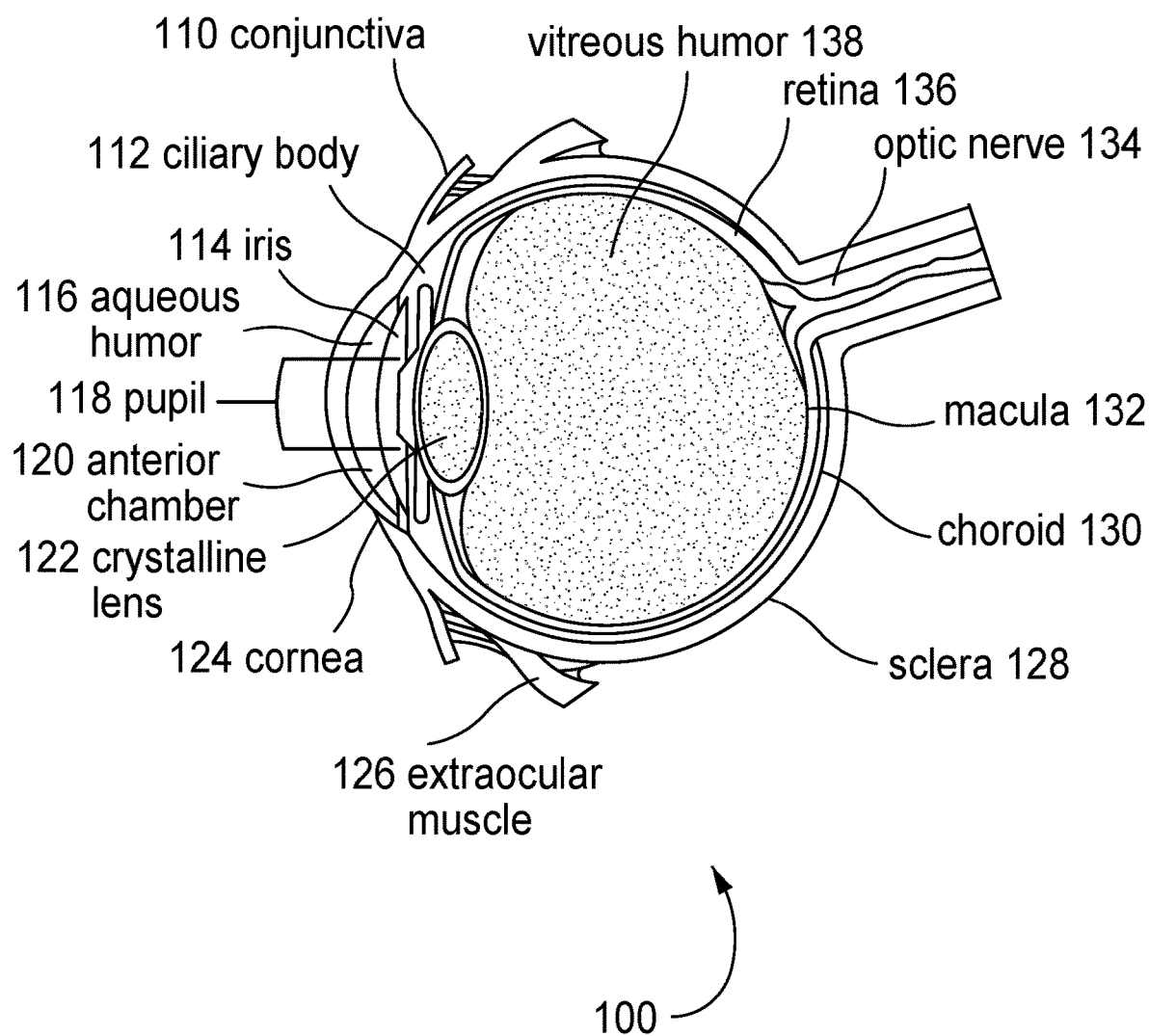

Hereinafter, various embodiments of the invention will be described. As used herein, any term in the singular may be interpreted in the plural, and alternately, any term in the plural may be interpreted to be in the singular.

Electro-active materials comprise optical properties that may be varied by electrical control. For example, transmission of light may be controlled to produce tinting or a sunglass effect. Further, the index of refraction may be electrically controlled to produce focusing and or prismatic effects. One class of electro-active material is liquid crystals. Liquid crystals comprise a state of aggregation that is intermediate between the crystalline solid and the amorphous liquid. The properties of liquid crystals may be controlled electrically, thermally, or chemically. Many liquid crystals are composed of rod-like molecules, and classified broadly as: nematic, cholesteric, and smectic.

There are several characteristics of electro-active materials which are useful in IOLs. First, the optical characteristics may be generated by thin layers (rather than by the curvature of conventional lenses which may require thick lenses). These thin layers may be placed in locations where it may be difficult to place conventional lenses, for example in the anterior chamber of the eye (between the iris and the crystalline lens). In addition, it is possible to stack (place in series optically) the electro-active layers in such a manner as to get an additive effect for the overall optical power created, including prism, conventional refractive error, or higher order aberration correction, in a thin structure that may be placed in either the anterior or the posterior chamber of the eye.

Second, the optical characteristics may be actively controlled. For example, an electro-active lens may designed to become darker (more tinted, and transmit less light) under bright light conditions. This tinting may be generated automatically by measuring the brightness using, for example, a photodiode or solar cell. Alternately, the tinting may be controlled by the decisions of the user by way of a remote control.

Similarly, the focus of an electro-active lens may be controlled electrically. The focus may be controlled automatically using, for example, a range finder, or a tilt meter, or triangulation based on the direction of both eyes, the forces exerted on the lens by the muscles of the eye. Alternately, the focus may be controlled by the decisions of the user by way of a remote control.

Third, electrical control creates the potential for correcting complex and high order visual defects. Conventional intraocular lenses are limited to addressing certain visual defects for various manufacturing reasons. However, an electro-active lens with a large number of individually addressable controlled small elements (for example, an array of very small pixels) may address very complex and high order visual defects. Further, the control may be simplified by creating individually addressable elements in arbitrary configurations, such as a series of concentric circles, or a series of approximately concentric ellipsis, or whatever customized configuration efficiently corrects the visual defect. The design, manufacture, and control of an array of small pixels has similarities with the manufacture of Liquid Crystal Displays (LCDs). Correction of complex visual defects such as higher order aberrations of the eye creates the possibility of "superhuman" visual acuity, wherein the vision is not limited by the lenses (either biological or corrective), but rather is limited by the inherent anatomy and physics of the photoreceptor cells in the retina. 20/10 vision or better is possible even before additional magnification is considered. Further, it is possible for an electro-active lens to act as a telescope or as a microscope.

Fourth, electrical control creates the potential for changing the optical characteristics of the electro-active IOL as desired. For example, the desired optical characteristics may be determined after the IOL is surgically implanted in order to compensate for any changes that occur during surgery, or for that matter an error in calculating or estimating the post surgery refractive error. Similarly, the optical characteristics of the IOL may be varied over time to compensate for changes in the user's eye. For example, if the user has a degenerative disease that affects a portion of the retina, then it is possible to remotely cause the implanted electro-active IOL to create prismatic power or even change its prismatic power in order to shift the image to a portion of the retina that is undamaged. By way of example only, each month (or as needed) the image may be shifted to the remaining undamaged portion of the retina with the highest concentration of receptor cells. This change can be accomplished post-surgically and remotely (meaning without additional surgery).

Fifth, electrical control creates the potential for the user to automatically or instinctively control the focus. For example, contractions of the muscular ciliary body can be measured by an piezoelectric element (as a strain gauge), and these contractions can then be used as a control input to electrically adjust the focus of the IOL, similar to the way the ciliary body would focus the natural crystalline lens by physical deformation. Additionally, in theory, the focus could be controlled by electrical signals directly from the brain. Recent development with artificial limbs use this technique.

Sixth, electrical control creates the potential to shift the field of view, and thus compensate for diseases that prevent the eyeball from moving. Nervous signals to diseased muscles (that can no longer move the eye) may be intercepted, translated, and used to electrically shift the field of view.

Seventh, there are many types of electro-active element configurations. These configurations include: pixelated (typically a two dimensional array of pixels similar to a liquid crystal monitor on a computer), rotationally symmetric pixelated (for example, a set of concentric circles), and diffractive. Electro-active individually addressable pixelated diffractive lenses may use concentric ring shaped electrodes to product the diffractive lens power with varying index of refraction without physically machining, molding or etching diffractive elements into the surface of the lens.

The electro-active element may be used in combination with a conventional lens, wherein the conventional lens may provide a base refractive power. The electro-active element may be used in combination with a diffractive lens having a machined, molded, or etched surface or geometry. The electro-active element may be used in combination with a second electro-active element, wherein each may perform a different function. For example, the first electro-active element may provide focus, and the second may provide tinting or may serve as an electrically controlled aperture, or the second could cause a prismatic shift of the image to the healthy area of a retina of a deceased eye.

Eighth, as discussed above, it is possible to electrically replace many of the optical functions of a natural eye: tinting may replace or augment the light reducing effect of the contraction of the iris, focusing may replace the natural deformation of the crystalline lens, focusing and prismatic shifting may replace movement of the eyeball, and so forth. Among other factors, the present invention addresses: positioning the IOL, energy storage, energy recharging, power generation, control, steering of the line of site to a targeted region of the retina altering the refractive power of the eye, augmenting or replacing the accommodative power of the crystalline lens, remote tuning post surgery of the electro-active IOL. Tuning comprises altering the power of the IOL and/or altering the location of the focus on the retina of the IOL.

FIG. 1 displays the major anatomical components of a human eye. The major anatomical components are: conjunctiva 110, ciliary body 112, iris 114, aqueous humor 116, pupil 118, anterior chamber 120, crystalline lens 122, cornea 124, extraocular muscles 126, sclera 128, chorid 130, macula lutea 132, optic nerve 134, retina 136, and vitreous humor 138. Although a human eye is described, this invention is also applicable to non-human eyes such as horses or dogs.

As background, the optical components of the eye will be described in detail. Light entering the eye first enters the cornea 124. The cornea 124 is transparent and provides about 40 diopters of the approximately 60 diopters total refractive power of the eye. Light then passes through the pupil 118. The pupil 118 is an aperture, and is variable in diameter from 1 mm to at least 8 mm. This gives an aperture range in excess of f20-f2.5, and a ratio of 32:1 for the amount of light permitted to enter the eye. The iris 114 serves as an adjustable diaphragm creating a pupil 118. The light then passes through the crystalline lens 122. The crystalline lens 122 is a transparent, encapsulated, biconvex body which is attached circumferentially to the ciliary body 112. The crystalline lens 122 contributes about 17 diopters to the total refractive power of a relaxed eye. The refractive power of the crystalline lens 122 may be altered by contractions of the ciliary muscles in the ciliary body 112, which deform the crystalline lens 122 and alter its refractive power. The light then passes through the vitreous humor 138 and finally contacts the retina 136. The retina 136 is the sensory neural layer of the eyeball and may be considered as an outgrowth of the brain, and is connected to the brain through the optic nerve 134. Near the center of the retina 136, the macula lutea 132 contains a central region of highest visual sensitivity called the fovea centralis or foveola (see FIG. 7) with a diameter of approximately 0.4 mm where the visual resolution is the highest. The small diameter of the foveola is one of the reasons why the optical axes must be directed with great accuracy to achieve good vision.

Thus, the human eye has an adjustable diaphragm (iris 114) and an adjustable refractive power (due to the ciliary body 112 deforming the crystalline lens 124).

An IOL can be placed in one of three locations: in the anterior chamber 120, which is between the cornea 124 and the iris 114; or in the posterior chamber (not shown) which is between the iris 114 and the crystalline lens 122; or as a replacement for the crystalline lens 122.

Generally, if the crystalline lens is diseased or damaged, then an IOL may be used to replace the crystalline lens. This IOL replacement for the crystalline lens may be accommodative, or non-accommodative. Replacing the crystalline lens allows the IOL to be conveniently positioned inside of a clear bag-like capsule that previously held the natural crystalline lens, and also allows the possibility of retaining some variable focus capability through interaction with the muscular ciliary body which circumferentially surrounds the clear bag-like capsule. In other cases, the IOL is placed extra capsulary (without the bag-like capsule).

However, if the crystalline lens is still functional, then it may be preferable to leave the crystalline lens undisturbed and to place the electro-active IOL into either the posterior chamber or the anterior chamber 120 of the eye, or into the corneal tissue similar to the Small Diameter Corneal Inlay (SDCI) discussed above. In these embodiments, the electro-active IOL could, by way of example only, provide optical power to correct for conventional refractive errors, correct for non-conventional refractive errors, create a prismatic image shifting effect that moves the location of focus to a healthier area of the retina, and add a tint, as opposed to replacing the optical power of the otherwise healthy crystalline lens.

Conventional refractive error is defined as one or more of: myopia, hyperopia, presbyopia, and regular astigmatism. Non-conventional (or higher order) refractive errors are defined as all other refractive errors or aberrations which are not conventional refractive error.

In many cases, the electro-active IOL may be used during cataract surgery when the existing crystalline lens is defective. In this case, the electro-active IOL will actually replace the removed defective existing crystalline lens, and may provide a range of electro-active optical correction including conventional and/or non-conventional refractive errors, as well as provide refractive power to make up for the lost optical power resulting from the removal of the crystalline lens. In addition, the electro-active IOL can provide for the ability to accommodate without any movement, translation or change in its surface geometry. This is accomplished by localized programmed changes in the index of refraction of the electro-active IOL.

The most common and advanced cataract surgery technique is phacoemulsification or "phaco." The surgeon first makes a small incision at the edge of the cornea and then creates an opening in the membrane that surrounds the cataract-damaged lens. This thin membrane is called the capsule. Next, a small ultrasonic probe is inserted through the opening in the cornea and capsule. The probe's vibrating tip breaks up or "emulsifies" the cloudy lens into tiny fragments that are suctioned out of the capsule by an attachment on the probe tip. After the lens is completely removed, the probe is withdrawn leaving only the clear (now empty) bag-like capsule, which may act as support for the intraocular lens (IOL).

Phacoemulsification allows cataract surgery to be performed through a very small incision in the cornea. Stitches are seldom needed to close this tiny entry, which means that there is less discomfort and quicker recovery of vision than with other surgical techniques. Small incisions generally do not change the curvature of the cornea (unlike larger incisions that were required with older surgical techniques). Small incisions for more rapid rehabilitation of vision and possibly less dependence on glasses for good distance vision.

After removal of the cataract-damaged lens, an artificial intraocular lens (IOL) may be implanted. The IOL may be produced from soft acrylic or solid medical-grade silicone. IOLs may be folded so they can be implanted with a small injector, which uses the same incision through which the phaco probe was inserted at the beginning of the procedure. As the IOL is implanted, it may be allowed to unfold and anchor itself behind the eye's pupil over the remaining clear capsule. The IOL(s) to be implanted may be selected based on power calculations made before surgery. In the case of the present invention, the electro-active IOL may also be selected based on the range of electro-active correction required, the type of any other ocular disease being treated, and any special needs of the patient.

In most cases, the electro-active element would contribute typically +2.5 Diopters, +2.75 Diopters, +3.0 Diopters, or +3.25 Diopters of optical power. The base lens portion (which the electro-active element is in optical communication) which would contribute most, if not all, of the approximately 17 Diopters normally provided by the crystalline lens, would be measured and selected prior to surgery. However, unlike a conventional IOL, an electro-active IOL allows for remote tuning of its optical power (for example, in case the calculations made prior to surgery are not optimum after surgery).

FIGS. 2A and 2B illustrate an IOL assembly 200 according to an embodiment of the invention. FIG. 2A displays a front view of the IOL assembly, which includes an electro-active lens element 218 powered by a thin, annular charge storage capacitor 216 arranged around the perimeter of the electro-active lens element 218. The charge storage capacitor 216 is charged by a piezoelectric film 212. The piezoelectric film 212 generates this charge as a result of mechanical forces applied by the ciliary body (not shown). The piezoelectric film 212 is attached to the ciliary body by a ciliary body attachment tab 210.

The ciliary body expands and contracts as the eye attempts to focus from near to far and from far to near. The ciliary body movement may produce tension and/or compression of the piezoelectric film 212 which produces electricity. The electricity may be transferred through charging leads 220 and used to charge the charge storage capacitor 216 (or a rechargeable battery). The charge storage capacitor 216 may power the electro-active lens element 218 and any related control circuitry (not shown). Typically, the electro-active lens element 218 requires approximately 1.0 to 5.0 volts, with a preferred range of 1.5 to 2.5 volts. These relatively low voltages decrease the risk involved with surgical placement of electrical devices.

The electrical characteristics of the piezoelectric film 212 under tension or compression may be used as a gauge to determine the desired viewing distance, and may be used to focus the electro-active lens. Thus, it is possible for the user to instinctively and automatically control the focus of the electro-active IOL 200 using the muscular ciliary body. The contractions of the muscular ciliary body previously focused the subject's crystalline lens by physically deforming it. Using the electro-active IOL 200 the instinctive and automatic contractions of the muscular ciliary body will change the electrical characteristics of the piezoelectric film 212, and these electrical changes may be monitored by a processor disposed, for example, on a chip (not shown) and used to electrically, variably focus the electro-active IOL 200. Alternatively, the piezoelectric film 212 may be used solely as a gauge for focusing, in which case, the electro-active IOL 200 would be provided with a different source of power.

In some embodiments, the piezoelectric film may be attached circumferentially to the ciliary body by multiple attachment tabs (more than two) in order to take advantage of the natural circumferential contraction and expansion of the surrounding ciliary body.

One or more lens anchors 214 may be used to stabilize the electro-active lens in the desired location. For example, a lens anchor 214 may be used to center the electro-active lens inside of the capsule or "bag" or membrane which formerly contained the natural crystalline lens (creating an intracapsular IOL). Alternately, the lens anchor 214 may be attached to the ciliary muscle directly, and thus be outside of the capsule (creating an extracapsular IOL).

Multiple lens anchors 214 may be used. For example, 3 or 4 lens anchors 214 may be used. The lens anchors 214 may have different shapes, customized to the specific application.

An optional base lens 252 may provide a base refractive power using a conventional lens configuration, and may be equivalent in refractive power to the crystalline lens when no accommodation is needed. The base lens 252 may also serve as a means of encapsulating the electro-active element in a hermetically sealed enclosure that consists of a biocompatible material similar to those materials currently used to make IOLs, by way of example only, soft acrylic or solid medical-grade silicone.

FIG. 2B displays a side view of an intraocular lens embodiment with an electro-active lens and piezoelectric material as a power supply. Specifically, FIG. 2B illustrates the optional base lens 252 which may surround the electro-active lens element 218 and which may provide a fixed or base refractive power. In a particular embodiment, the fixed or base refractive power may be adapted to focus the eye at near distances when the electro-active element is inactive. In another embodiment, the fixed or base lens may be adapted to focus the eye at far distances when the electro-active element is inactive. The optional base lens 252 may have multiple focal points, and/or may be tinted.

Other sources of power may include: solar cells, inductive charging, conductive charging, laser, thermoelectric, and harnessing the mechanical energy from blinking. The capacitor 216 (or optionally, a battery) may be recharged inductively with a pair of special glasses (spectacles) that may also remotely turn off the electro-active lens while the battery is being recharged. The special glasses may also be configured to provide vision correction while the battery is recharging.

Figure 5:
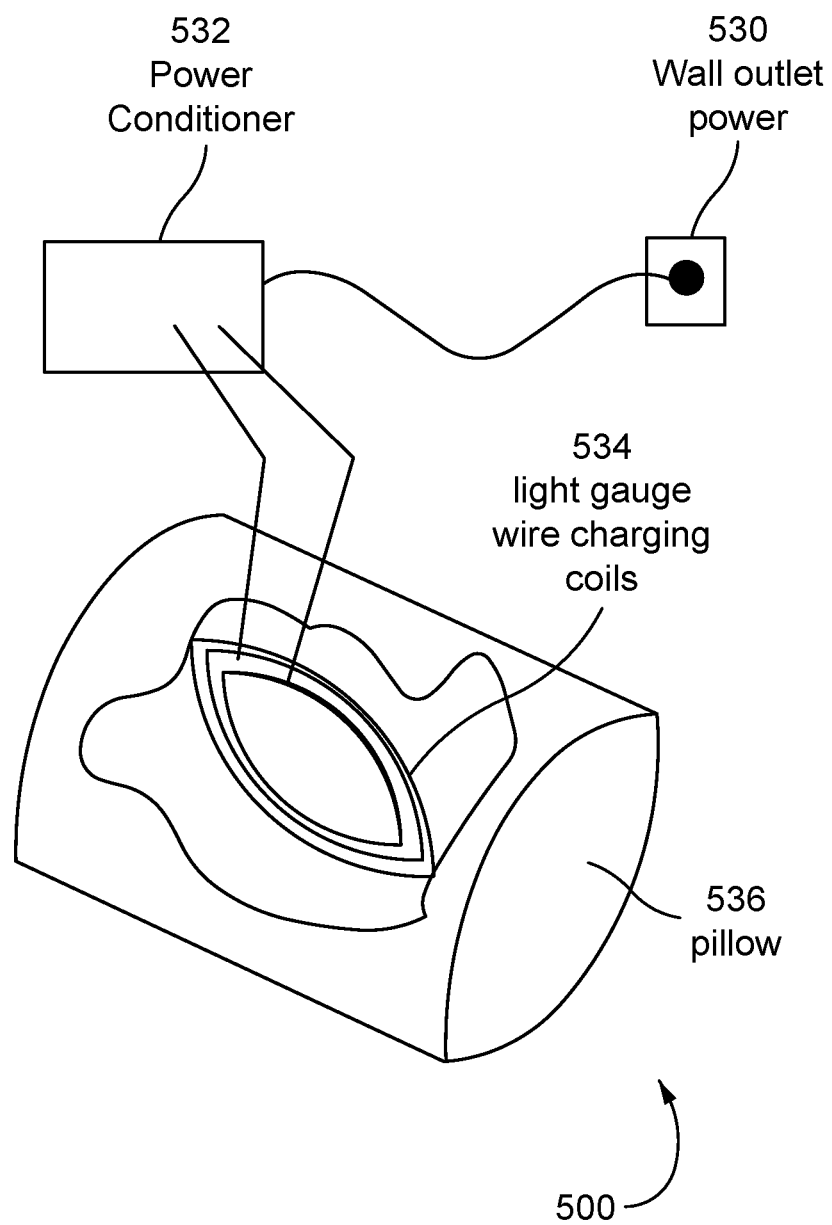

In some embodiments, the capacitor 216 in the electro-active IOL 200 may be charged with a special pillow that has very light gauge wires through which current runs. The pillow may thus be used to charge the batteries inside the electro-active IOL 200 at night while the patient sleeps. An exemplary arrangement of this type is illustrated in FIG. 5 and will be discussed in more detail below. A power conditioning circuit is used to reduce the voltage and limit the current to safe levels for low power charging and to adjust the frequency for more efficient charging.

Alternately, the electro-active IOL may not have a capacitor 216 or battery, but may be constantly powered conductively by an externally located battery, or may be constantly powered inductively by an externally located inductively coupled power supply, or solar cell, or solar cell coupled to a properly tuned laser, or a thermal-electric power supply that generates electricity by dumping body heat (typically 98 degrees F.) into the relatively cool ambient air (typically 70 degrees F.).

Figure 3A:
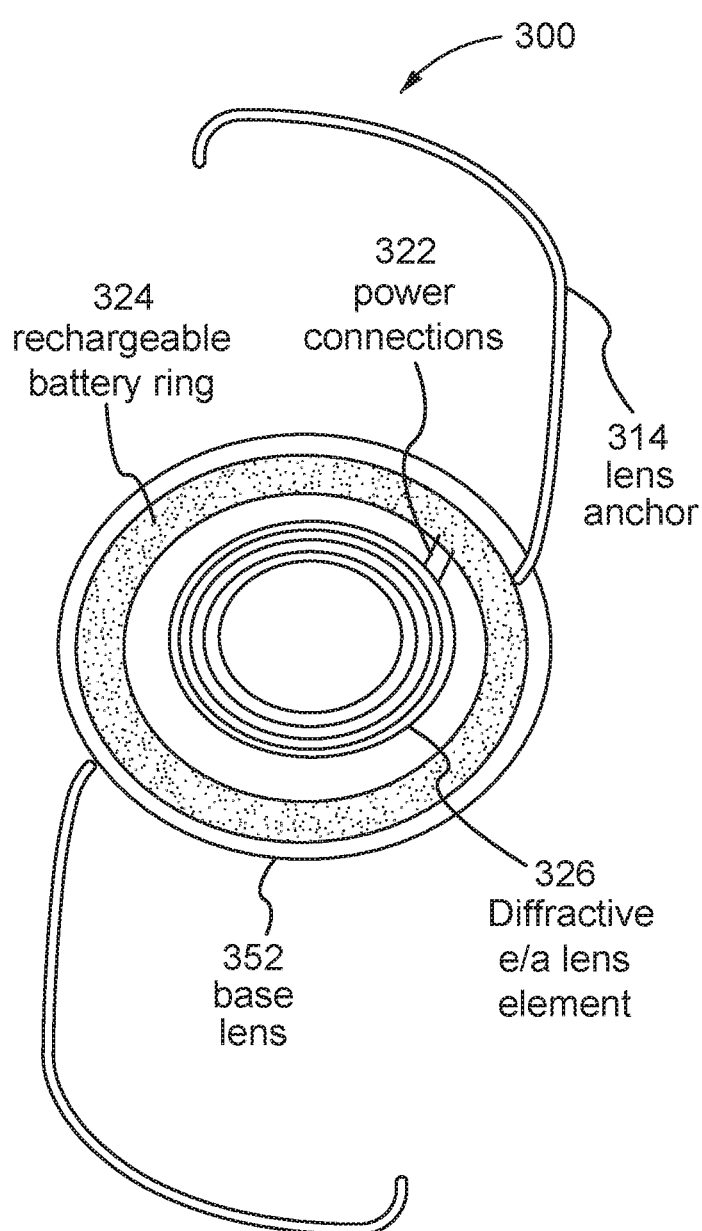
Figure 3B:
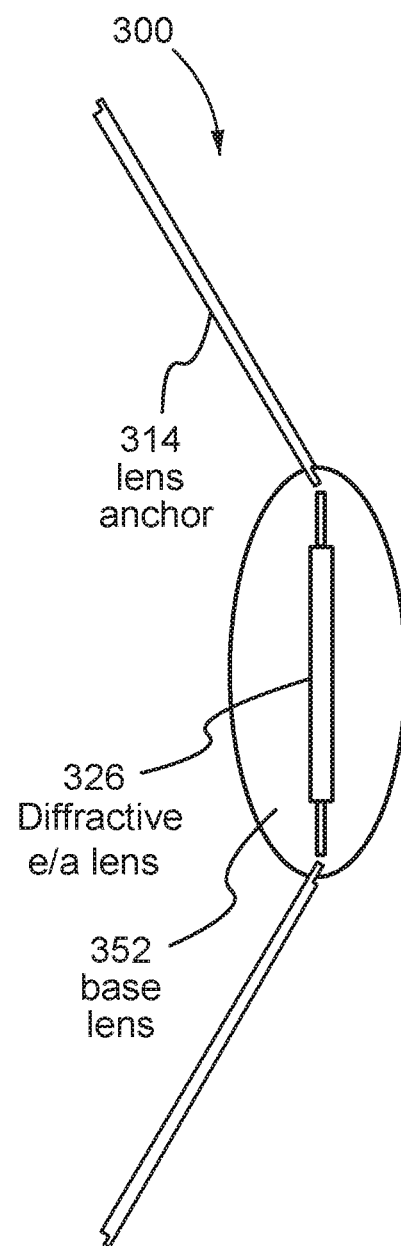

FIGS. 3A and 3B display an intraocular lens system 300 having a diffractive electro-active lens element 326 and a rechargeable battery ring 324. FIG. 3A provides a front view of the diffractive electro-active lens element 326, said diffractive lens element can be either electrically diffractive with circular concentric electrodes, or mechanically diffractive with etched surfaces that are activated electrically by controlled by index matching and mismatching. which is connected by power connections 322 to the rechargeable battery ring 324. Lens anchors 314 may be used to stabilize and position the diffractive electro-active lens element 326 in the desired location and orientation. The rechargeable battery ring 324 may be powered with a capacitor similar to that of intraocular lens system 200 of FIGS. 2A and 2B. Further, the rechargeable battery 324 may be shaped differently and located inside of or adjacent the lens anchor 314, and thus be moved away from the optical elements.

FIG. 3B displays a side view of the intraocular lens 300. Specifically, FIG. 3B illustrates an optional base lens 352, which is similar to the base lens 252 of the intraocular lens system 200 of FIGS. 2A and 2B. This base lens 352 may have a base or fixed optical power, or may have no optical power and merely serve as a protective capsule or substrate.

FIGS. 4A and 4B display an intraocular lens system 400 having a pixelated electro-active lens element 430 and a rechargeable battery ring 424. FIG. 4A shows a front view of the pixelated electro-active lens element 430, which is connected by power connections 422 to the rechargeable battery ring 424. Lens anchors 414 may be used to stabilize and position the diffractive electro-active lens element 430 in the desired location and orientation. The rechargeable battery ring 424 may be powered in the same ways as capacitor 216 from FIG. 2.

FIG. 4B displays a side view of the intraocular lens 400 showing the base lens 452, which is similar to the base lenses of the previous embodiments.

FIG. 5 displays an external power supply 500 for use in charging the internal power supply of IOLs according to some embodiments of the inventions. In the power supply 500, a power conditioner 532 is electrically connected to a wall outlet 530. The power conditioner 532 is connected to light gauge wire induction coils 534 inside of a pillow 536 for inductively charging a capacitor or battery of a rechargeable electro-active IOL. The power conditioner 532 may be configured to reduce the voltage and limit the current to safe levels for low power charging and to adjust the frequency for more efficient charging. The power supply 500 may be configured so that the electro-active IOL may be charged while a subject rests his head on or near the pillow 536. It will be understood that the induction coils 534 may alternatively be placed in a subject's bedding or in a headrest, seatback or other location that can be in close proximity to a subjects head for a sufficient period of time.

Figure 6:
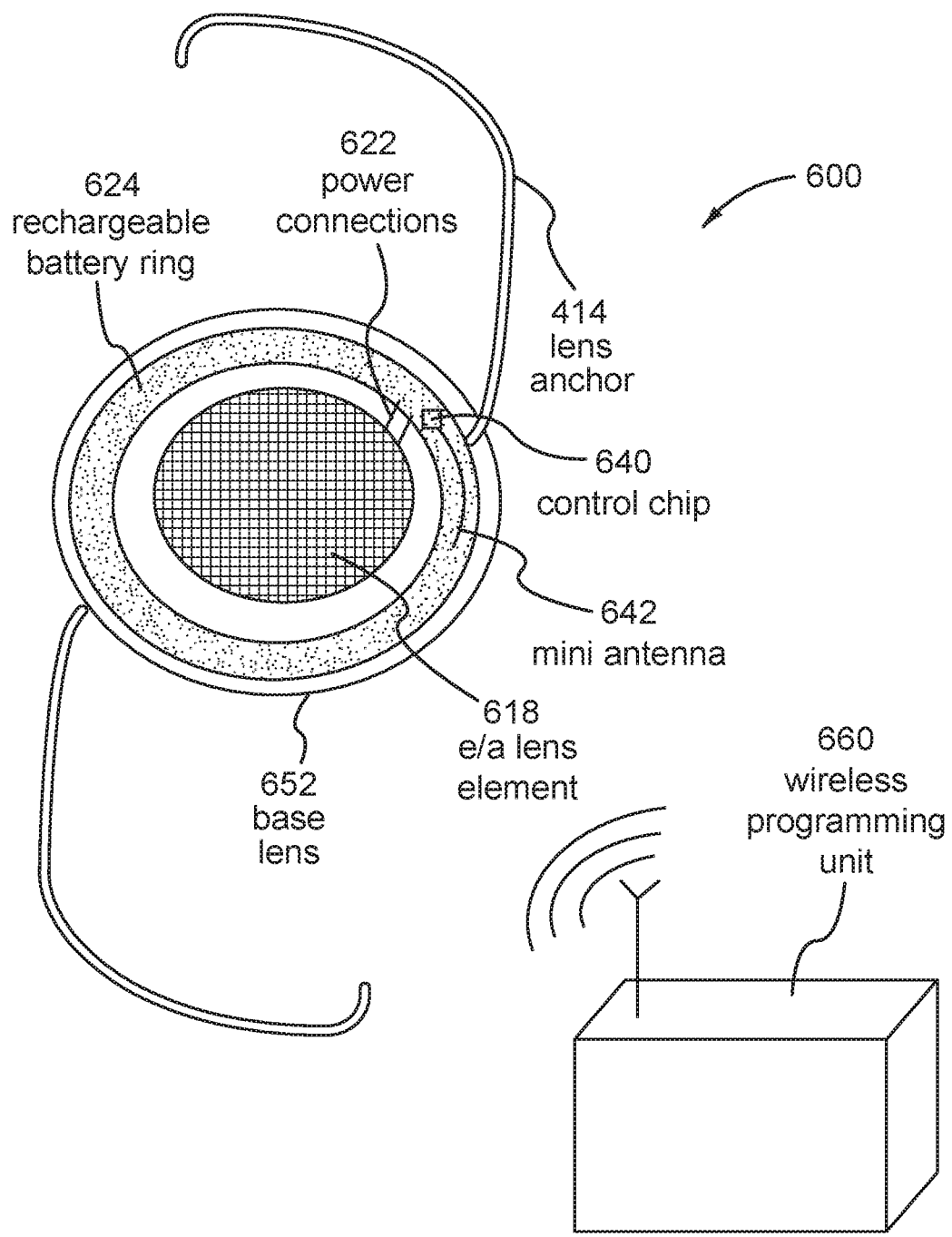

FIG. 6 displays an intraocular lens assembly 600 with an electro-active lens element 618, a control chip 640 and an antenna 622 for use with a wireless programming unit 660. The wireless programming unit 660 is configured to communicate with the control chip 640 through radio waves. The radio waves are picked up by the mini antenna 642 which communicates with the control chip 640. The control chip 640 may be remotely tuned through the use of these radio waves. Such tuning may include setting or adjusting the optical characteristics of the electro-active lens element 618. The control chip 640 controls the electro-active lens element 618, and may have bi-directional communication with the wireless programming unit 660. For example, the control chip 640 may be configured to alert the wireless programming unit 660 that the battery 624 voltage is low. Alternately, programming communication with the control chip 640 may be through a laser (light waves), instead of through radio waves.

The electro-active lens element 618 may be connected by power connections 622 to a rechargeable battery ring 624 or a capacitor (not shown), and may be charged by induction coils or by piezoelectric elements as in previously described embodiments.

In some embodiments, the correction provided by the electro-active IOL may vary depending upon the needs of the patient and the desired results. In some embodiments the electro-active element may only provide correction for presbyopia. In some embodiments, the electo-active IOL may provide remote fine tuned conventional correction. In some embodiments, the electo-active IOL may provide higher order (non-conventional) aberration corrections, by way of example only, coma, spherical aberration, trefoil, and other higher order aberrations. In some embodiments the electro-active element may also adjust the position of the image on the retina, by way of creating a prismatic shift of the image electronically. When correcting for higher orders aberrations and or correcting a prismatic shift of where the image is located on the retina, the electro-active IOL may utilize a plurality of pixels. A prismatic shift of the image is very useful in patients having conditions, by way of example only, macula degeneration of the retina (which may include alterations in color due to disease or specific degeneration of the macula lutea), macula holes, retinal tears, and neurological abnormalities that cause scotomas or a loss of vision in particular segments of the visual pathway (such as blind or dark spots in the field of vision, and blurred vision). It should be pointed out that in each of the use embodiments above the inventive electro-active IOL can be tuned remotely post surgery to effect the optimized effect desired.

Figure 7A:
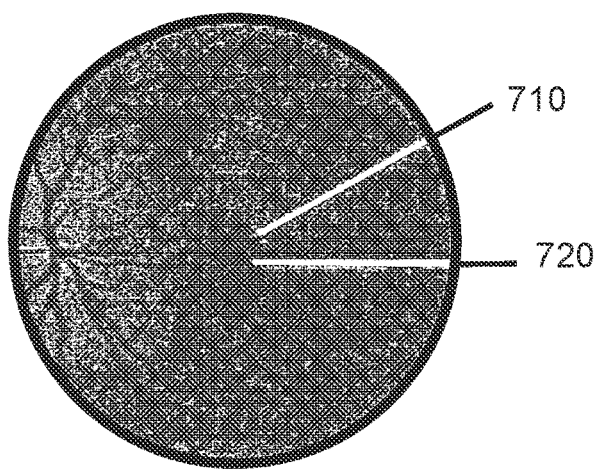
FIG. 7A is an image of an healthy retina illustrating the location of the macula and the fovea on the retina.
Figure 7B:
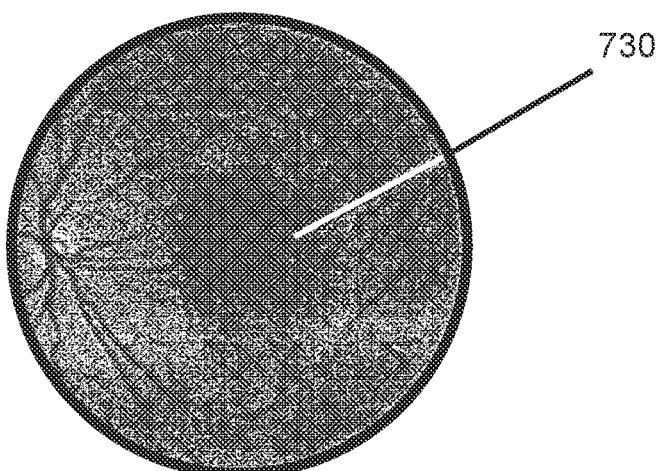
FIG. 7B illustrates an area of the macula that has been damaged by "wet" macular degeneration.
Figure 7C:
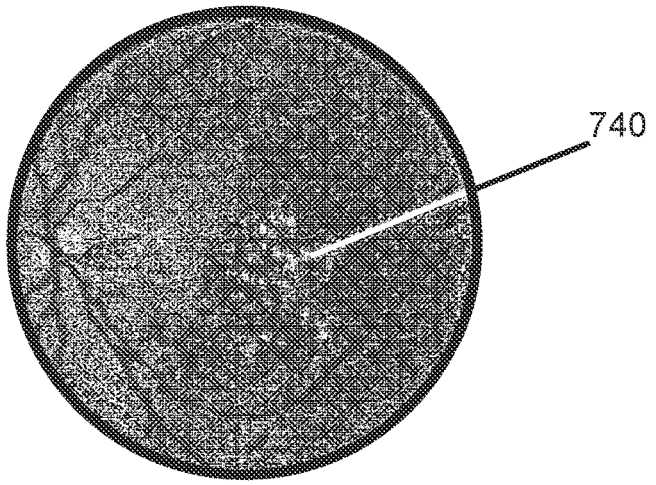
FIG. 7C illustrates an area of the macula that has been damaged by "dry" macular degeneration.

FIG. 7A illustrates an image of a healthy retina with a healthy fovea 720 and healthy macula 710. FIG. 7B illustrates an area of the macula 730 that has been damaged by "wet" macular degeneration, usually caused by bleeding from behind the retina that moves across membrane of the retina. FIG. 7C illustrates an area of the macula 740 that has been damaged by "dry" macula degeneration, which is caused by the build-up of drusen on the retina in the area of the macula. By moving the image to another location on the retina, vision can be improved for people suffering from macular degeneration. An image location change of 0.25 mm to 3.00 mm may make a major improvement in one's vision in the case of a diseased or damaged macula or retina. The preferred range is 0.50 mm to 2.00 mm.

Figure 8:
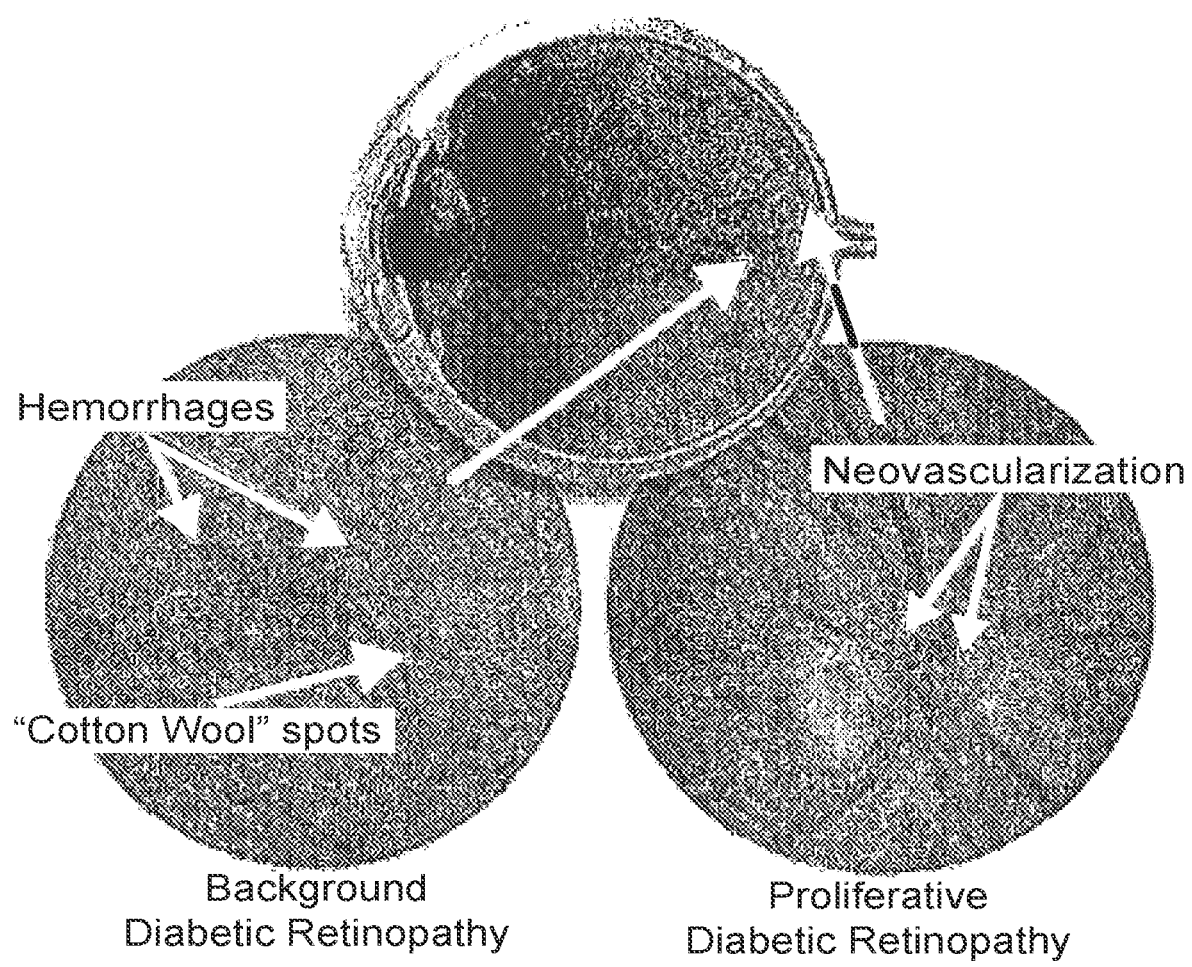
FIG. 8 illustrates the various manifestations of diabetic retinopathy.

FIG. 8 illustrates the effects of diabetic retinopathy on the eye. Again, by redirecting the image on the retina with a prismatic IOL, some of the visual clarity effects of this disease may be mitigated.

FIG. 9 schematically illustrates an embodiment whereby electro-active lenses with linear electrodes may be stacked to produce any combination of vertical and horizontal displacement of an image on the retina. The first lens 910 has horizontal electrodes used to produce vertical prismatic power. The second lens 920 has vertical electrodes used to produce horizontal prismatic power. The combined lens 930 would be able to produce a combination of vertical and horizontal image displacement. By changing the voltages on each electrode and invoking a technique known as phase-wrapping, a variety of prismatic powers may be produced by such a lens. Also, multiple lenses may be stacked to produce larger values of prismatic power. The amount of prismatic power required and the resulting amount of image shift will vary depending upon the extent of the disease. A preferred range of image movement is between 0.1 mm and 3.0 mm, with a preferred range of 0.5 mm to 2.0 mm.

Figure 10:
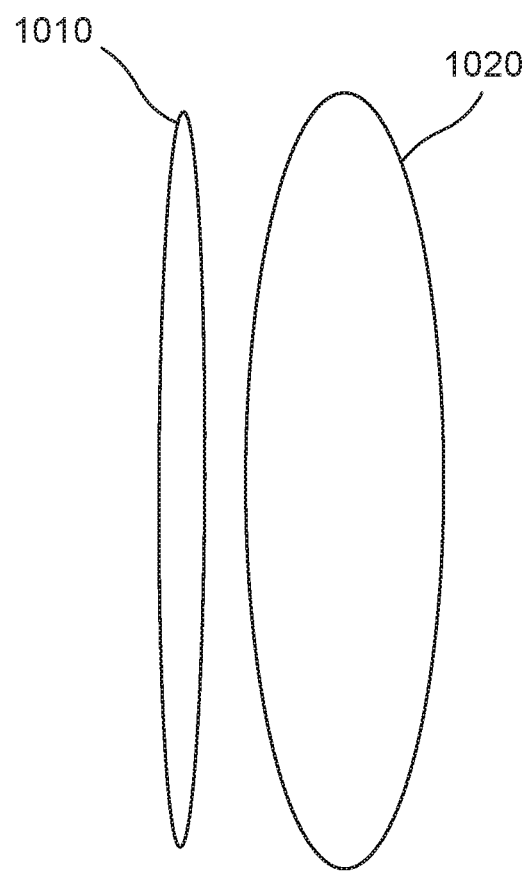
FIG. 10 illustrates an electro-active IOL in optical communication with a non-electro-active accommodative IOL.

FIG. 10 illustrates an electro-active IOL in optical communication with a non-electro-active accommodative IOL. Element 1010 is an electro-active lens that is in optical communication with non-electro-active accommodative IOL element 1020. Note that elements 1010 and 1020 are in optical series, but they are not physically touching each other.

While much consideration has been given to powering an electro-active lens, some electro-active materials retain their optical power in the absence of applied electricity (such as by way of example only, a bi-stable liquid crystal). Using these type of electro-active materials, the prismatic power, an additive or subtractive power that is additive or subtractive to the base optical power of the IOL, and/or the higher order corrections could be set while the device is being powered, and then would remain set after the power is removed. This may negate the need for recharging the power source in the IOL. If the patient's vision changes and requires new correction, he could return to the eye-care professional and have the IOL adjusted to a new combination of prismatic and/or higher order correction. The changes could be externally powered remotely. For example, the external power may be RF energy similar to the way RFID tags work today, where the reading device provides the power to the RFID tag inductively so that the RFID can transmit it's information to the RFID reader.

In same manner as the RFID tags, a tuning instrument for changing the IOL power could provide power to the controller on the electro-active IOL, so that the controller could change the voltages on the electrodes of the IOL thus setting the localized index of refraction that determines the optical properties of the electro-active IOL.

Alternately, the power may also be supplied optically by shining a bright light or eye-safe laser into the eye and onto a photocell built into the electro-active IOL that would then provide the temporary electrical power needed to adjust the optical power of the electro-active IOL. This system may also be used for communication, in addition to supplying power.

Bi-stable twisted nematic, cholesteric and ferroelectric liquid crystals have been used in flexible low cost LCD displays, and similar materials may be used in the electro-active elements of an IOL. This type of electrically adjusted (but otherwise non-powered) prismatic adjustment, additive or subtractive, for retinal disease tuning or higher order aberration correction may be added to (i.e., placed in optical series with) any accommodative non electro-active IOL that corrects for presbyopia. For example, electro-active elements could be placed in optical series with non-electrical or non-powered IOLs, such as non electro-active IOLs that mechanically change their optical power by changing one or more surface curvatures and/or the position of the IOL in the eye.

The addition of the electro-active lens or electro-active elements may be accomplished in at least three ways: first, a separate electro-active IOL may be placed in non-touching optical communication (optical series) with the non-electro-active accommodating IOL; second, an electro-active element can be built into one of the IOL's surfaces that does not change contour during accommodation; and third, an electro-active element may be placed inside of a layered non-electro-active.

For example, an electro-active element could be added in the anterior chamber and used in optical series with an individual's functioning crystalline lens. In this case, the crystalline lens will provide natural accommodation, and the electro-active IOL may steer the image to a healthier part of the retina, or may tune the non-electroactive IOL, or may correct for higher order aberration.

As noted above, in some embodiments, it may be a major advantage to tune or adjust the electro-active IOL remotely. After inserting the electro-active IOL in the eye, the optical power and the prismatic power can be fine-tuned remotely to accomplish the optimal vision correction to correct for conventional refractive error, or higher order aberrations, or the precise location of the image on the retina. Further, the IOL could be tuned again at a later date to compensate for changes in the eye over time, due to disease or aging. In cases of correcting solely for conventional refractive error, the electro-active IOL could either utilize diffraction or pixelation or both. The electro-active element may also perform any number of these functions in combination, as required by the patient's conditions and at the discretion of the eye care professional.

Figure 11:
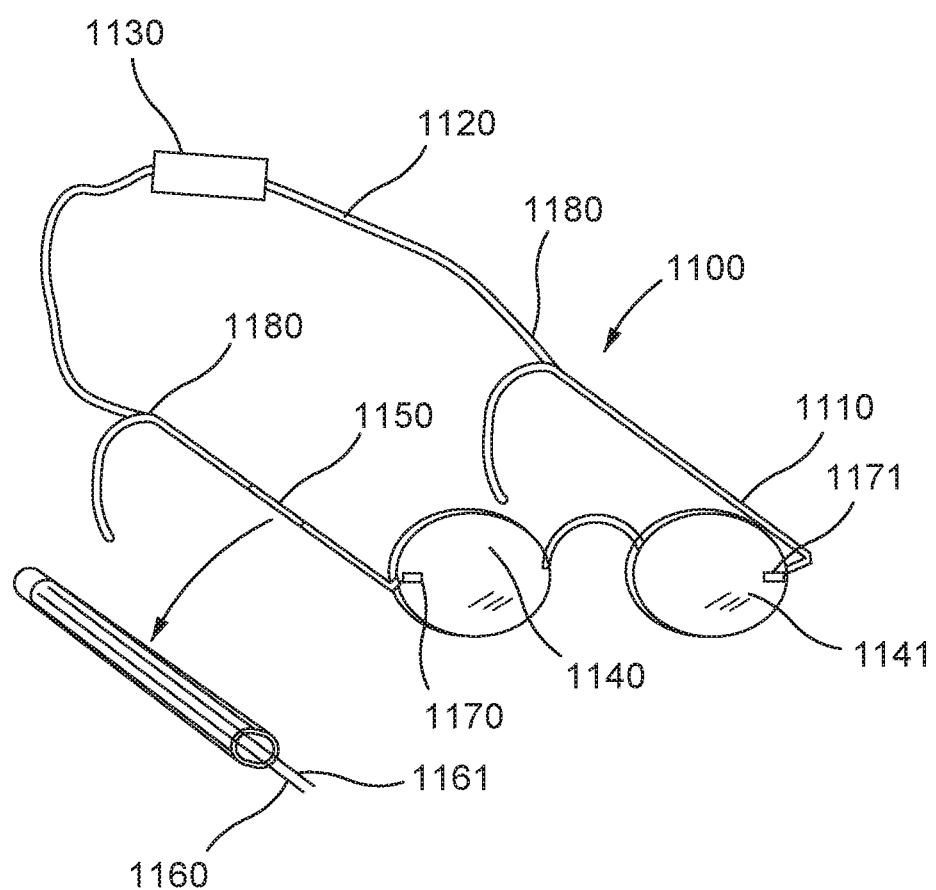
FIG. 11 illustrates an exemplary eyewear system according to aspects of the invention.

Shown in FIG. 11 is a diagram of the invention showing a pair of eyeglasses which can be mechanically and electrically coupled to an electronic lens feature, by way of example only, an electro-chromic lens, electro-active lens, microoptical display or heads-up display affixed to a spectacle lens or frame. The invention is designed in such a way that the electrical power source, by way of example only, battery or miniature fuel cell, in certain embodiments is stored in a pocket or enclosure that is connected to a tether, cord, chain or Croakie, which is then connected to the eyeglasses. In other embodiments of the invention the accessory or feature is connected to the tether, cord, chain or Croakie, but no pocket or enclosure is utilized.

The invention improves upon the conventional eye glass chord, chain or Croakie by modifying it to allow for not only being uses as a means of securing the eye glass frames to ones head, but in addition to provide for a means away from the eye glass frame to house or support the power source, and of course electrical connections. The invention further provides for off loading certain electrical accessories and features from the eyeglass frame, as well as the electrical connections to be detachable and re-attachable to the eyeglass frame in a very convenient and user-friendly manner. In one application of the invention, electrical connections are provided within the temple pieces of the glasses that allow the electrical signal (digital or analog) to travel to the lens by way of electrical conductors located internally in the frame. In another inventive embodiment, the electrical connectors are located on the outer surface of the temple and applied, by way of example only, with an adhesive film. In this case, the connectors are built into the film and then the film is affixed to the temple or temples. In still other cases, the connectors are applied directly to the frame and then covered by the adhesive film, which then connects to the lens.

The invention shown in the figure provides an electronic enabling tether that contains a power source such that it can be securely hung from the rear of the frame temples and be allowed to extend down to the wearer's upper back, just below the neck. The power source, in some embodiments, can be further secured to the wearer's back by: locating it under the shirt, using, by way of example only, an adhesive patch, Velcro applicator, snap, or clamp to adhere the unit to the wearer's back or shirt. Securing in this way prevents the unit from flopping around while the wearer is walking, jogging or engaged in some other athletic exercise or active work. When the invention is affixed to either one's body or shirt it should have enough length to allow the wearer to bend their head down at the neck without unduly tightening or pulling tautly on the audio unit. In most cases the power source is small and lightweight enough to be confined solely within the inventive tether. Therefore, it is not necessary to affix the enabling tether to one's body or shirt, etc.

In certain embodiments, elastic or rubber fittings are used to secure the inventive electronic enabling tether to the temple or temples. These embodiments may allow for a notch or grove to be placed or built into the temple. In certain other embodiments, the end of the temple or temples provides for a circular fastener, which may or may not be conductive, to which the invention is secured using, by way of example only, a clip.

The inventive electronic enabling tether is connected mechanically and electrically to the frames in a removable fashion. The inventive electronic enabling tether in certain embodiments utilizes a magnet connecting means. In other embodiments, no magnet is used. One such embodiment where a magnetic connector is used allows for the tether to be separated at some point near the mid-line of the tether for easy removal. In other embodiments, the tether is magnetically connected to the temple by way of a magnet attraction/ receiving member that is built into the temple connection device, such as by way of example only, an elastic, plastic, or metal fastener that connects the tether to the temple or eyewear frame. In certain cases where power is being supplied to the eyewear, the magnetic connection device also serves as an electrical conductor to provide the electrical connection from the inventive tether to the eyewear (lenses and/or frame). The power source contained within the electronic tether can be either rechargeable or non-rechargeable, in which case it will need to be readily accessible or removable within the tether to be changed from time to time.

The spectacle lenses can be constructed to contain a micro-optical display that is visible to the wearer, located in a fixed space in such a manner as to not obstruct the central vision area of the leases. In this version, an audio unit is replaced or enhanced by additional electronic capability to supply video or informational data. For example, if the unit contained a cell phone or PDA, emails can be transmitted to the micro-optical display or telephone calls can be transmitted to earphones. In this second function, a microphone would have to be added into the spectacle frames near the nose bridge to allow for two-way communication. The inventive electronic enabling tether provides the needed power and the potential offloading capability from the eyewear of items that need to be electronically connected but do not need to reside on the eyeglass frame or lenses.

Thus, the invention contained herein solves a pressing and growing need of enabling electronic frames in a manner that allows for the proliferation of various electronic applications that are now being applied to eye wear. It does this while preserving the fashion aesthetics, comfort and ergonomics of the electronic eyeglasses as compared to the current popular conventional non-electronic eyeglasses.

When reading about the inventive embodiments disclosed herein, it should be pointed out that the words "stem or temple" have the same meaning in what is disclosed herein as do the words clip-on and snap-on. A clip-on can be either monocular (attaching to one eyewire or one half of the frame front) or binocular (attaching to both eyewires or the complete frame front). Further, the electronic tether can be affixed to hinged temples, hinge-less temples, the frame front, or for that matter anywhere on the eyewear. The term eyewear is meant to be interpreted broadly, and may include one or more of a frame, lens, tether, and/or clip-on. The tether is considered an electronic tether when an electrical connection is affixed to it or travels within it. A temple is considered to be an electronic temple if an electrical connection is affixed to it or travels through it. A frame is considered to be an electronic frame if an electrical connection is affixed to it or travels through it. A lens is referred to as an electronic lens when electricity affects the lens' optical power or tint. A lens can be that of a fixed/static lens or a dynamic focusing electronic lens. The word tether includes that of a Croakie, chord, chain, and connecting attachment from one temple to another. Clip-ons can be that of electronic when an electrical connection is associated with the clip-on or non-electronic when no electrical connection is associated with the clip-on. Tints can be that of an electrochromic tint, a photochromic tint, or a fixed imbedded tint.

In FIG. 11, one embodiment of the present invention is shown. A pair of spectacles 1100 is shown with a frame 1110; attached to the frames is a tether 1120, which connects to the frame near the rear of the stems 1180, 1181. A cross-sectional view through the center of the stem center 1150 shows two conductors 1160, 1161 running through the frame stems or temples to provide electrical power from the power source inside the enclosure 1130 to the electronic controllers 1170, 1171 located on each lens 1140, 1141. The details of attachment will be addressed in subsequent drawings. It should be pointed out that the enclosures can be made from any number of materials including but not limited to cloth, fabrics, plastic, or even foam rubber. In the case of cloth or fabric, the access to the power source inside the enclosure may be via a Velcro™ strip cover. Such access or pockets are well known in the art. In the case of plastic, the enclosure may be done with a sliding door.

Figure 12:
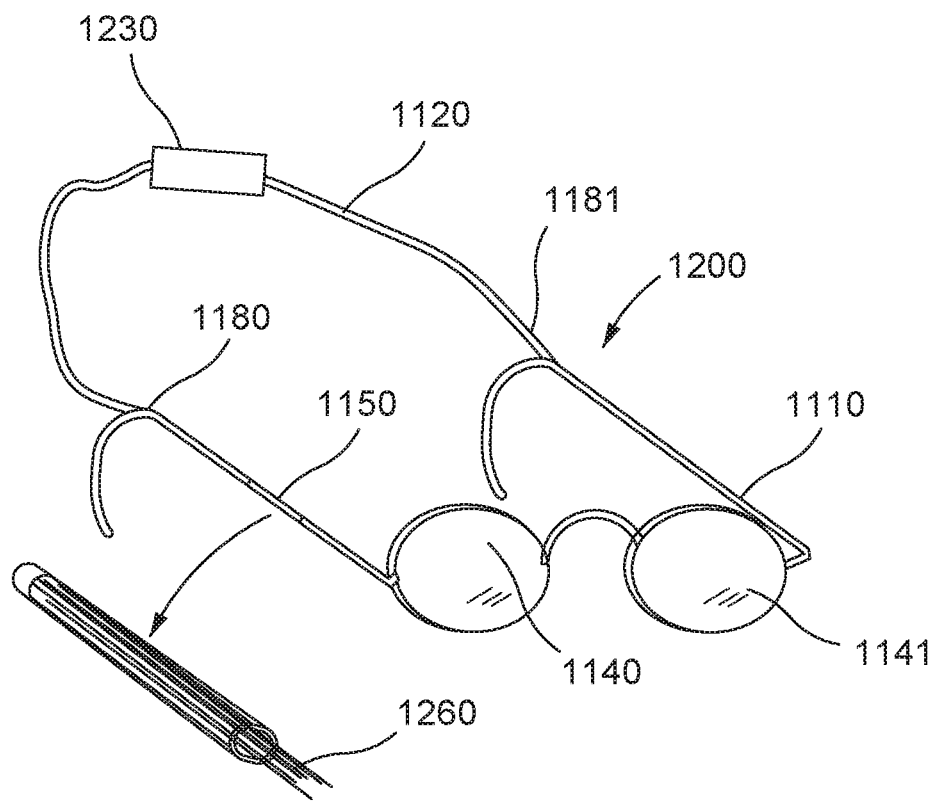
FIG. 12 illustrates another exemplary eyewear system in which an enclosure contains both a power source and an electronic controller according to further aspects of the invention.

FIG. 12 illustrates another embodiment of the present invention where the enclosure 1230 now contains both a power source and an electronic controller designed to control a pair of lenses. In such cases, depending on the type of electrically activated lenses being used, multiple electrical conductors 1260 will need to be run through the tether and through the frame stems as shown in the detailed section of FIG. 12.

Figure 13:
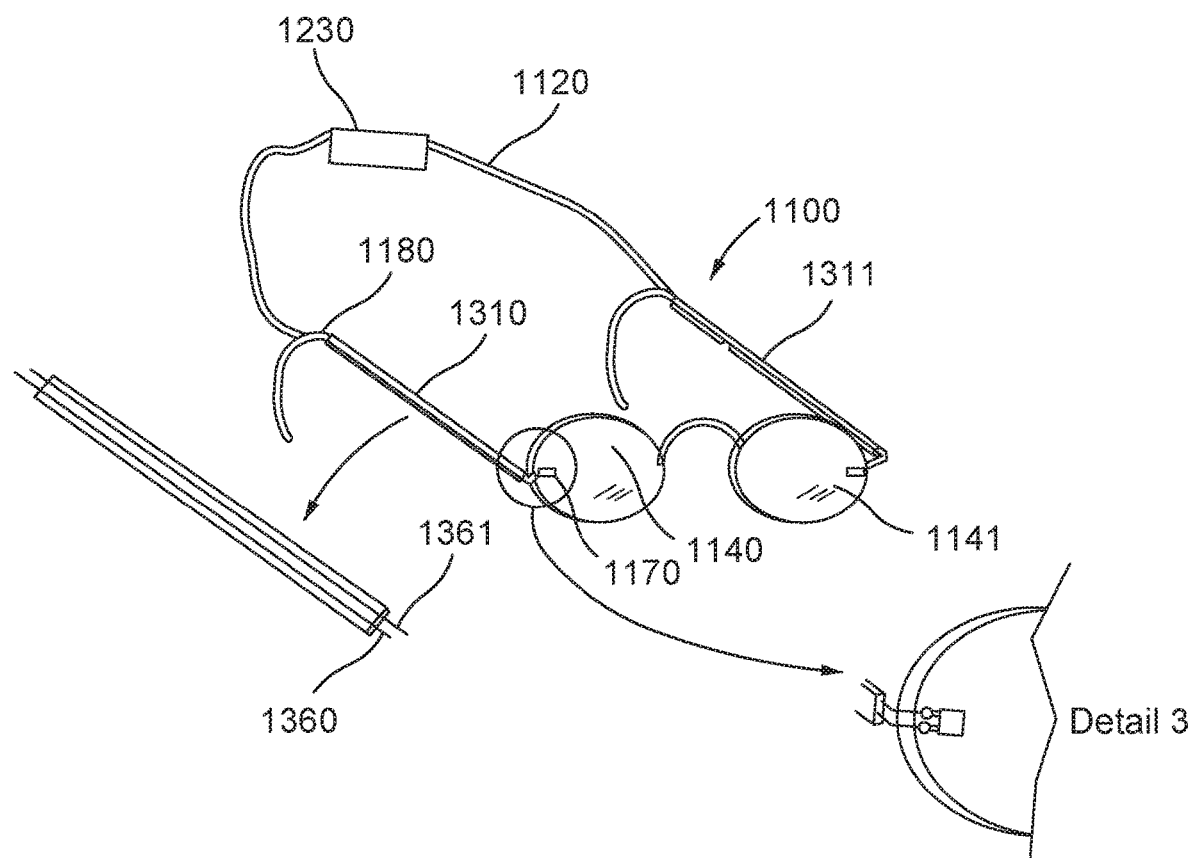
FIG. 13 illustrates another exemplary eyewear system, including details of conductor connections, according to further aspects of the invention.

FIG. 13 illustrates yet another embodiment where by the controller/power source in the enclosure 1230 is connected to the frame with an adhesive strip or conformal film 1310, 1310 on each side of the frame 1110. The detail in FIG. 13 illustrates two conductors 1360, 1361 running inside the film 1310 to provide power to the controllers 1170, 1171 on the lenses 1140, 1141. In this embodiment almost any frame may be used to provide power to the electro-active lenses.

FIG. 13 also illustrates how the two conductors may make contact with the controller on the lens. In this case, small holes are drilled near the contact points for the controller power on the lens. The wires are then placed in each hole and secured with as electrically conductive adhesive, such as, by way of example only, epoxy or acrylic filled with silver or other metallic flakes or powder. Such conductive adhesives are well known in the art. The wires are strain-relieved by virtue of the adhesion of the strip to the frame stem or temple (not shown in FIG. 13 for clarity of electrical attachment details).

Figure 14:
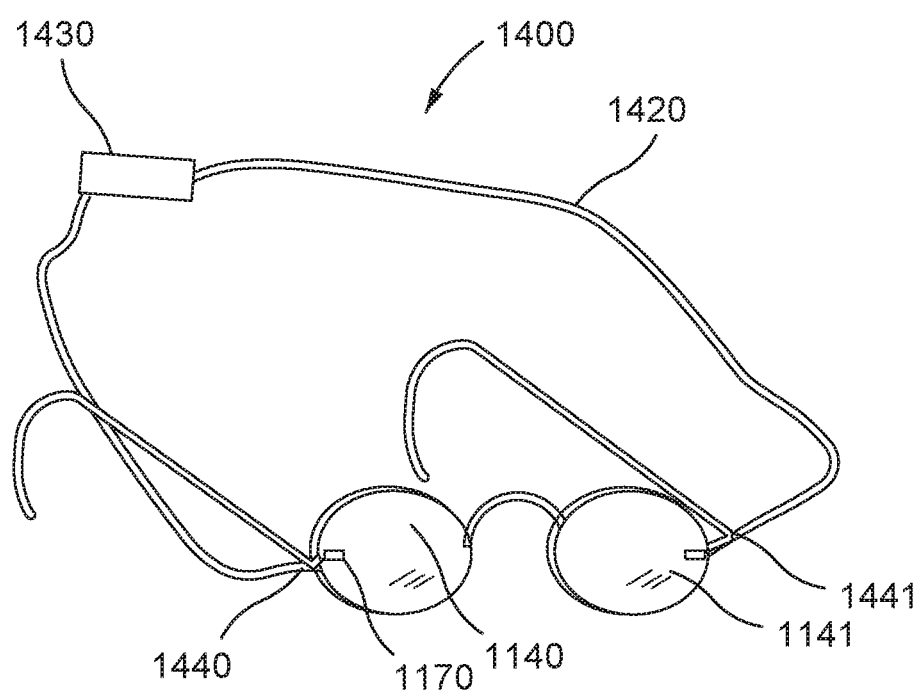
FIG. 14 illustrates another exemplary eyewear system in which a controller and power source are connected directly to the frame temples according to further aspects of the invention.

FIG. 14 illustrates yet another embodiment where by the controller/power source in the enclosure 1430 is connected directly to the frame temples 1440, 1441 to provide power to the controllers 1170, 1171 on the lenses 1140, 1141. In this embodiment the tether 1420 may need to be longer. This embodiment may be totally frame-independent and may be preferable for female wearers.

Figure 15:
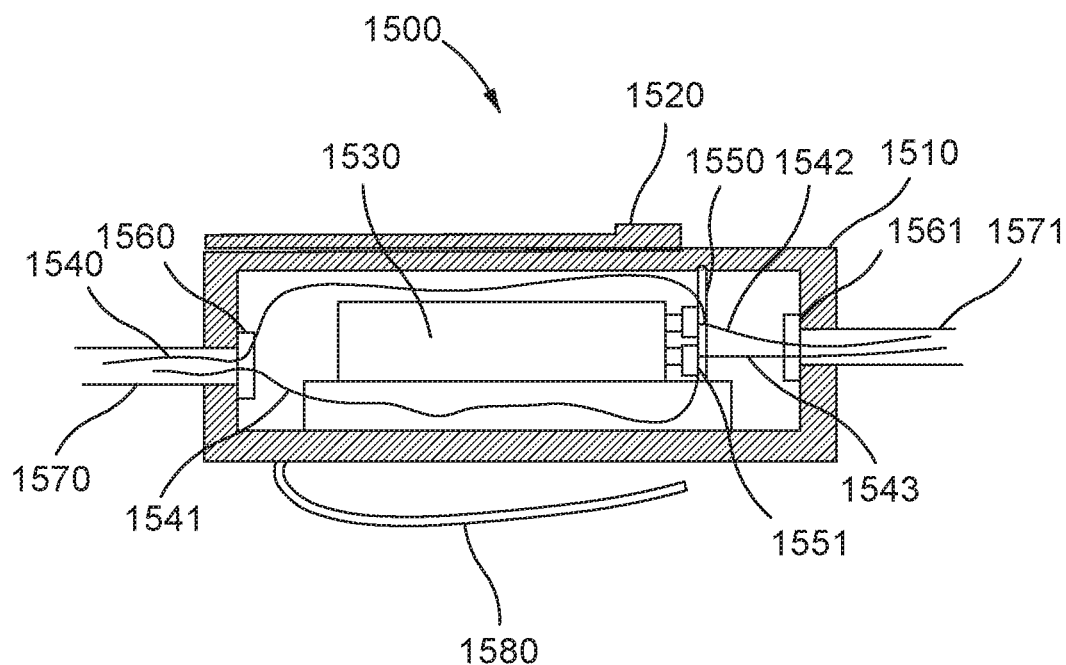
FIG. 15 illustrates an enclosure including a power source according to further aspects of the invention.

FIG. 15 illustrates the details of the enclosure described above where the enclosure 1510 includes a power source or battery 1530. A sliding door 1520 allows for access into the enclosure for changing the power source. Electrical conductors 1540, 1541, 1542, 1543 provide power to the lenses through the tethers 1570, 1571. The tethers are secured to the housing of the enclosure with strain reliefs 1560, 1561 so that any tension in the tether is applied to the outer covering of the tether and not the conductors inside the tether. The power source is connected to terminal blocks 1550, 1551 that make connection to the four conductors. Finally, a clip 1580 is attached to the enclosure to secure the enclosure to a part of the clothing such as the collar of a shirt. Many types of power enclosures for small electronic devices are known in the art, and while the inventor has illustrated an example herein, other designs are anticipated and would be considered within the scope of the present invention. It should be pointed out that the enclosures can be made from any number of materials including but not limited to cloth, fabrics, plastic, or even foam rubber. In the case of cloth or fabric the access to the power source inside the enclosure may be via a Velcro™ strip cover.

Figure 16:
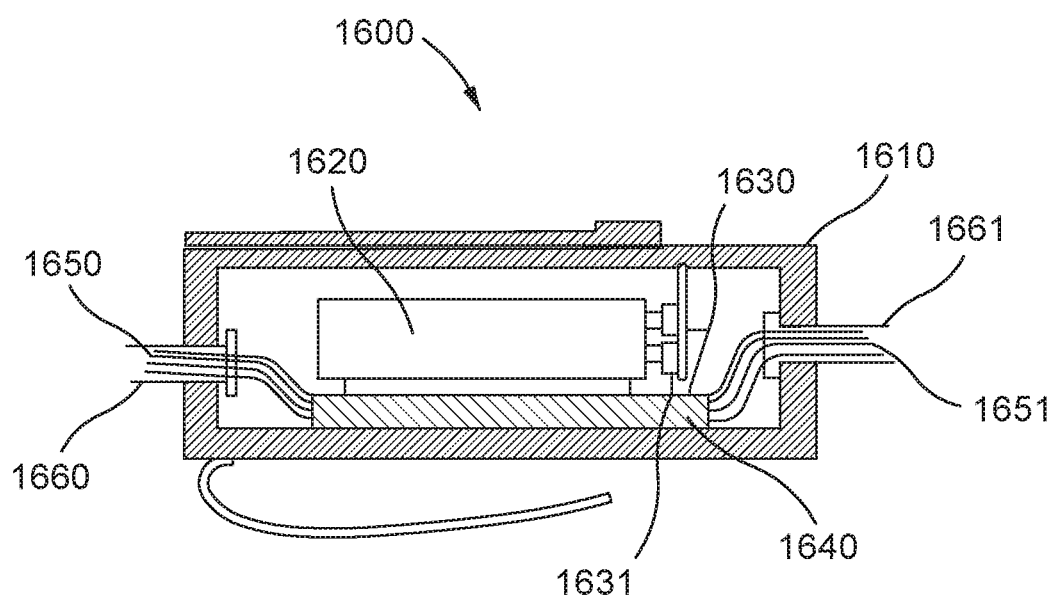
FIG. 16 illustrates an enclosure including a power source and a controller according to further aspects of the invention.

FIG. 16 illustrates the details of the enclosure described above where the enclosure 1610 includes both a power supply 1620 and a controller or control circuit 1640. The power supply 1620 provides power to the controller 1640 via two conductors 1630, 1631. The controller then provides drive signals to the lenses via multiple conductor bundles 1650, 1651 that reside inside the tether sleeves 1660, 1661. The number of conductors in each bundle will depend on specific requirements for the particular type of electrically activated lenses that are placed in the frame.

Figure 17:
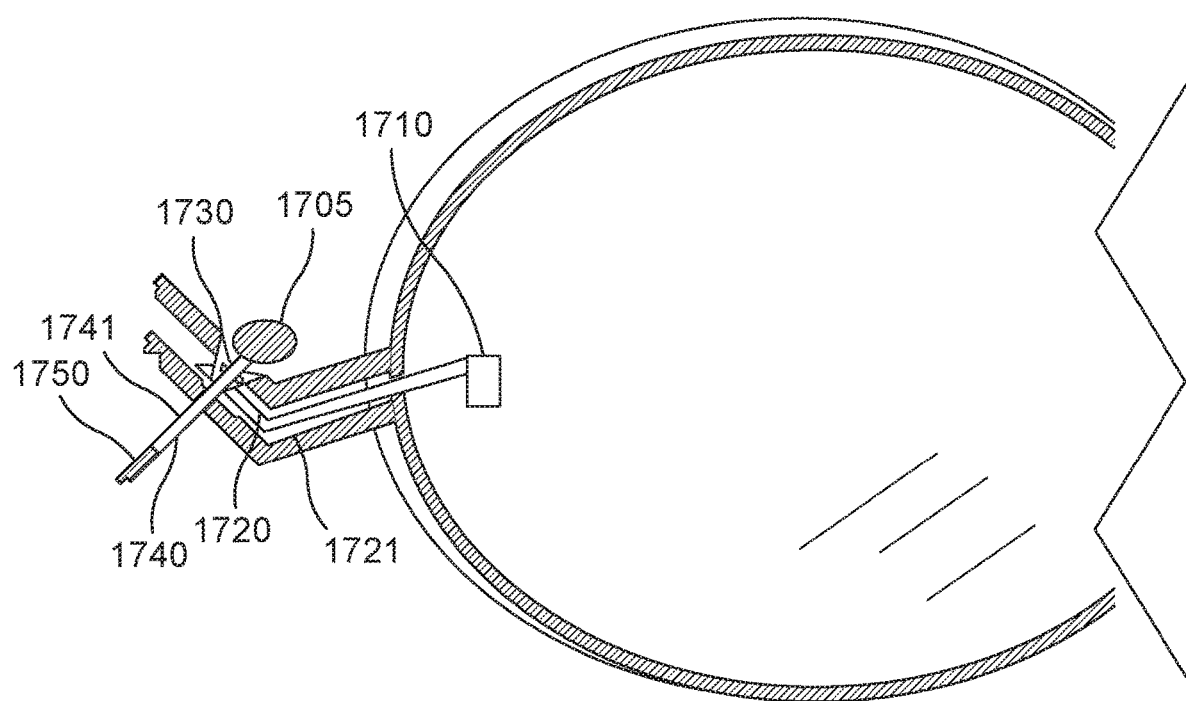
FIG. 17 illustrates an exemplary tether attached to eyewear frame according to further aspects of the invention.

FIG. 17 illustrates one embodiment for attaching the tether to the frame. In this case an elastic member 1705 slides into a groove notched in the frame stem. Each side of the groove is connected to the controller 1710 via small wires 1720, 1721. The sides of the grooves are isolated from one another with an insulator or gap (not shown). The tether 1750 contains the two conductors 1740, 1741 coming from the power source, and on each side of the tether a contact point 1730 is placed to establish electrical contact to each side of the grove. By shaping the tether such that its cross section is roughly triangular, proper polarity can be maintained upon connection. Further, the rubber nature of the elastic member and tether sleeve can act as a strain relief and avoid damage to the conductors inside the tether.

Figure 18:
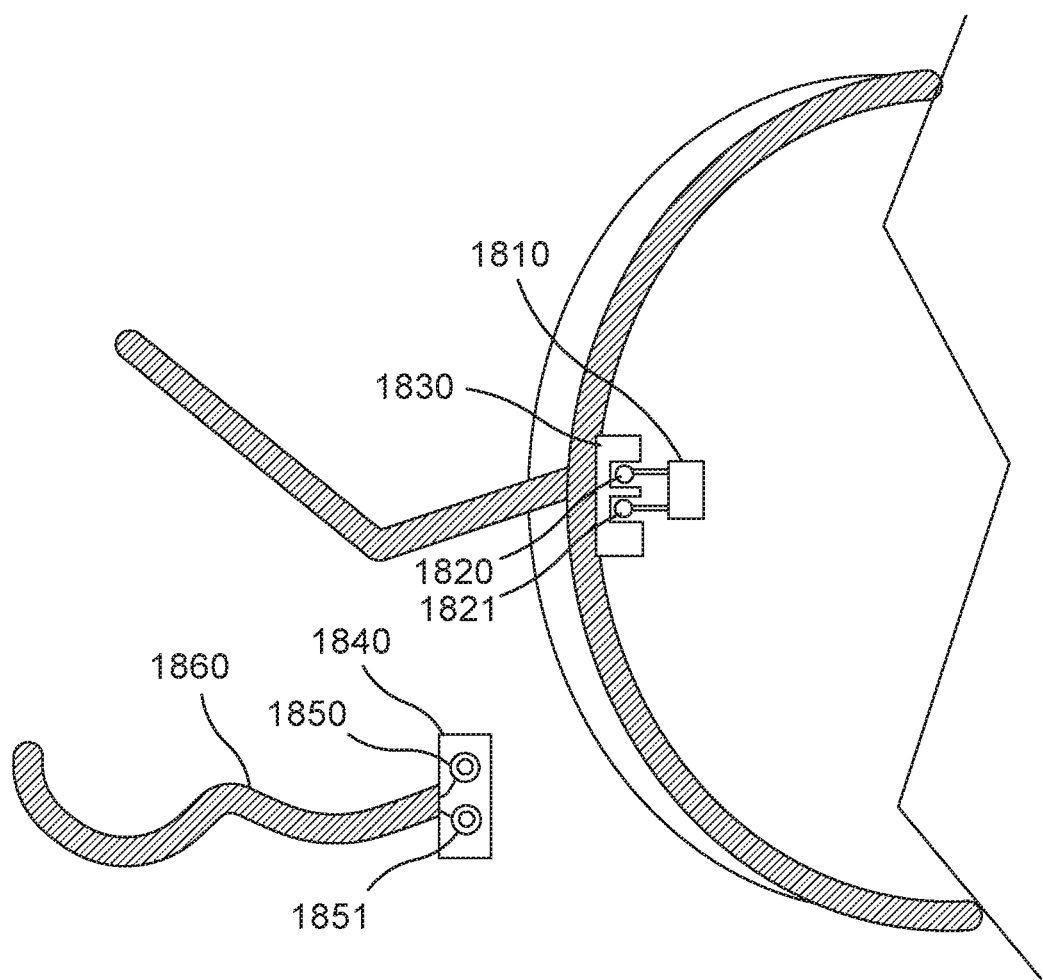
FIG. 18 illustrates details of an edge connection using magnetic attraction according to further aspects of the invention.

FIG. 18 illustrates a connection mechanism utilizing magnetic attraction. In this case the controller 1810 is electrically connected to two contact points 1820, 1821 via ultra thin wires or ITO buses. The contact points are surrounded by a tiny steel plate (or other material having good magnetic properties) 1830 with small cut-outs to avoid shorting out the two contact points. Meanwhile; the tether 1860 has a small but powerful magnetic plate 1840 attached to its ends. Within the magnetic plate are two holes that contain contact points 1850, 1851 to the two conductors within the tether. In this manner the attraction of the steel plate to the magnetic plate force both a physical and an electrical connection from the tether to the lenses. The front side of the magnetic plate can be painted or coated with a finish that is similar to the frame finish so that the connection is cosmetically acceptable to consumers. While this type of connection has been shown at the lens surface, a similar connection can be made at any point on the tether if so desired. It should also be pointed out that this inventive connection can also be located on the surface of the frame as opposed to that of the lens, in which case a further connection would be made to the lens. Moreover, while the shape was illustrated as a rectangle, other geometries could be used where appropriate and would be considered within the scope of the present invention. Also, the magnetic connection could be used exclusively as a mechanical connection to a tether as opposed to one that always provides electrical connectivity.

Figure 19:
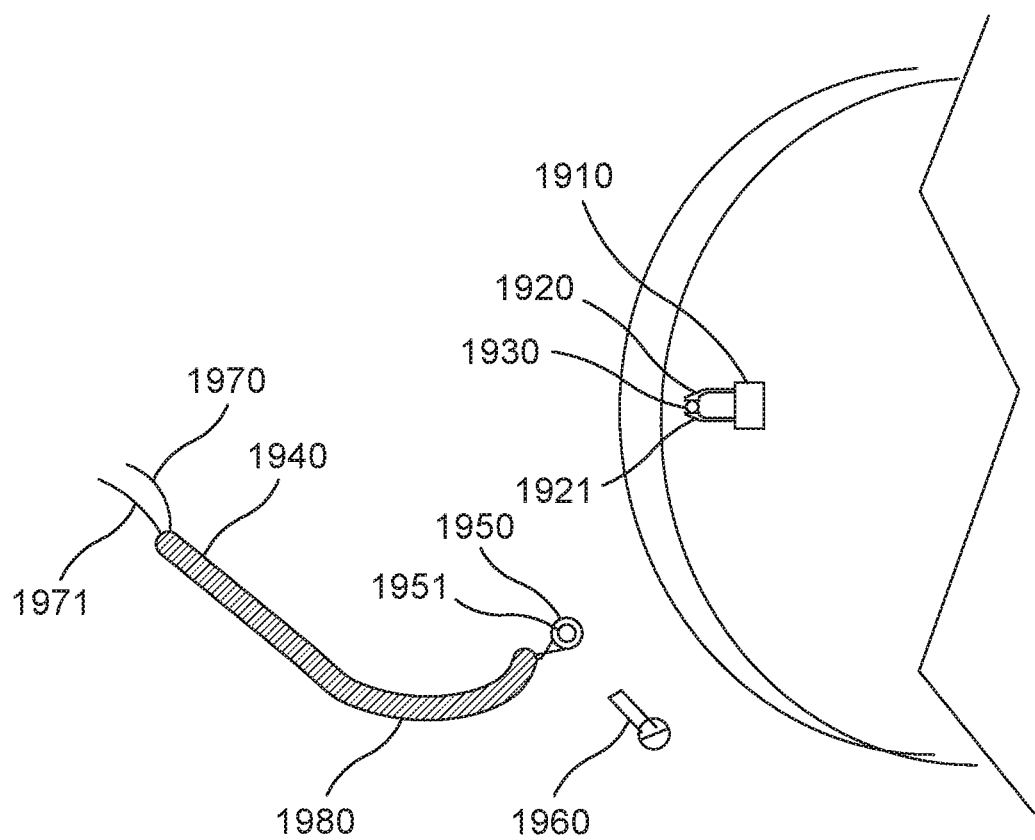
FIG. 19 illustrates details of an attachment design whereby the temple contains conductive wiring according to further aspects of the invention.

FIG. 19 illustrates an attachment design whereby the temple contains conductive wiring and is designed for a rimless mounting of the lenses. In this case the controller 1910 has contact points 1920, 1921 that are semicircular and are located about the location for a through hole 1930 that will be drilled through the lens as part of the mounting process. The frame temple 1940 has a loop with two conductive contact rings 1950, 1951 that attach to each of the two conductive wires 1970, 1971 within the frame temple. Finally, a screw 1960 can be used to hold the lens to the temple 1980 of a rimless/hingeless frame made from high strength metals such as titanium (which is widely used in the fabrication of hingeless frame), while establishing the electrical connection. Either the hole in the lens can be tapped with threads or a small bolt (not shown) can be placed on the back of the lens for fastening. In the case of this embodiment, it is possible to conduct electricity over the full or partial length of the temple to the lens without having any connections at or through the frame hinges, as no hinges are needed.

Figure 20:
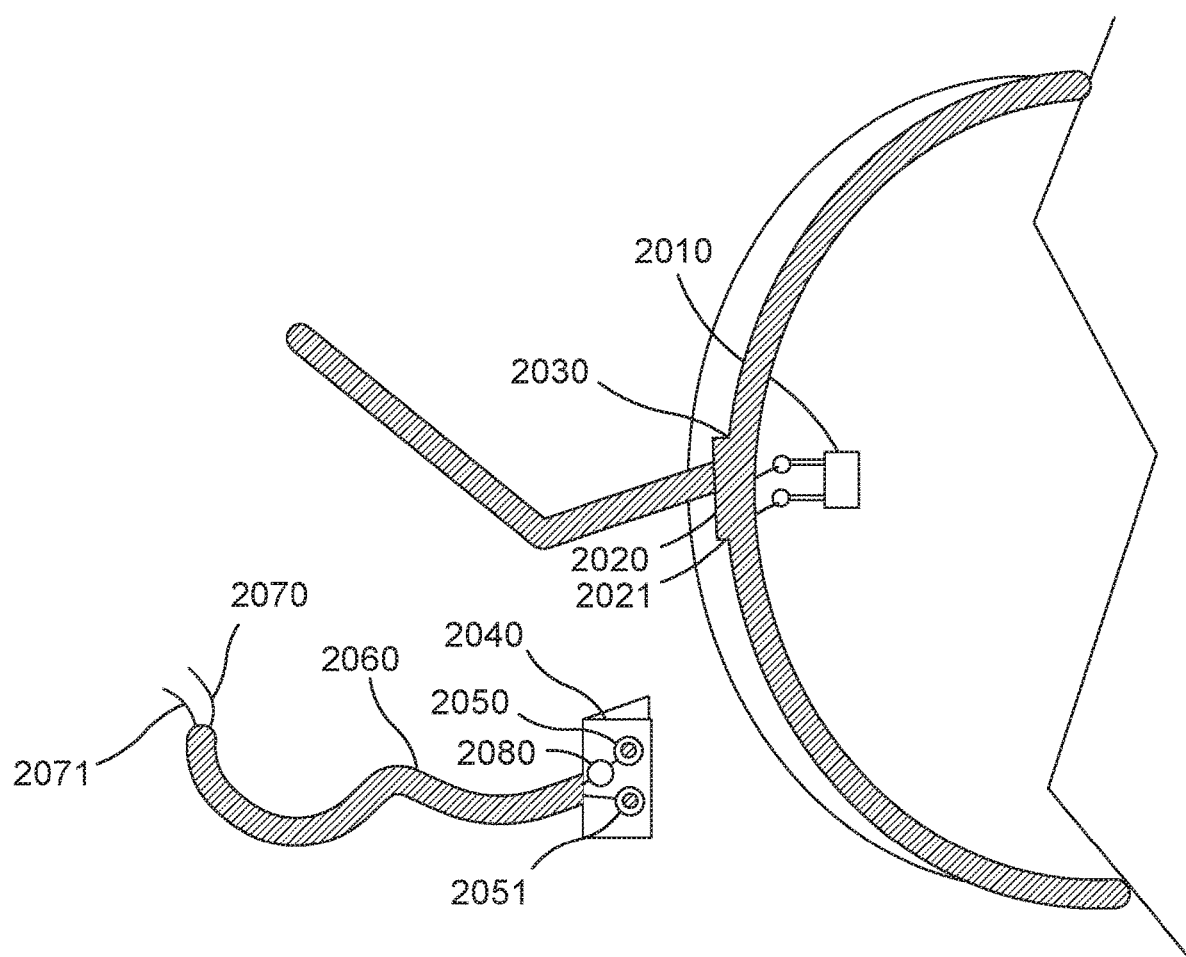
FIG. 20 illustrates details of attachment of a tether using a clamp according to further aspects of the invention.

FIG. 20 illustrates attachment of the tether using a clamp. Again, the controller 2010 has contact points on the lens 2020, 2021 near a flange 2030 on the outer perimeter of the frame. The tether 2060 has a clamp 2040 (in this case a v-shaped clamp) that contains two conductive contact points 2050, 2051 for providing power to the lens once the tether is in place. Additionally, a tilt switch 2080 may be used to break the electrical connection from one of the two conductive wires 2070, 2071 as part of a control mechanism for electro-active lenses used for, by way of example only, correcting presbyopia.

Figure 21:
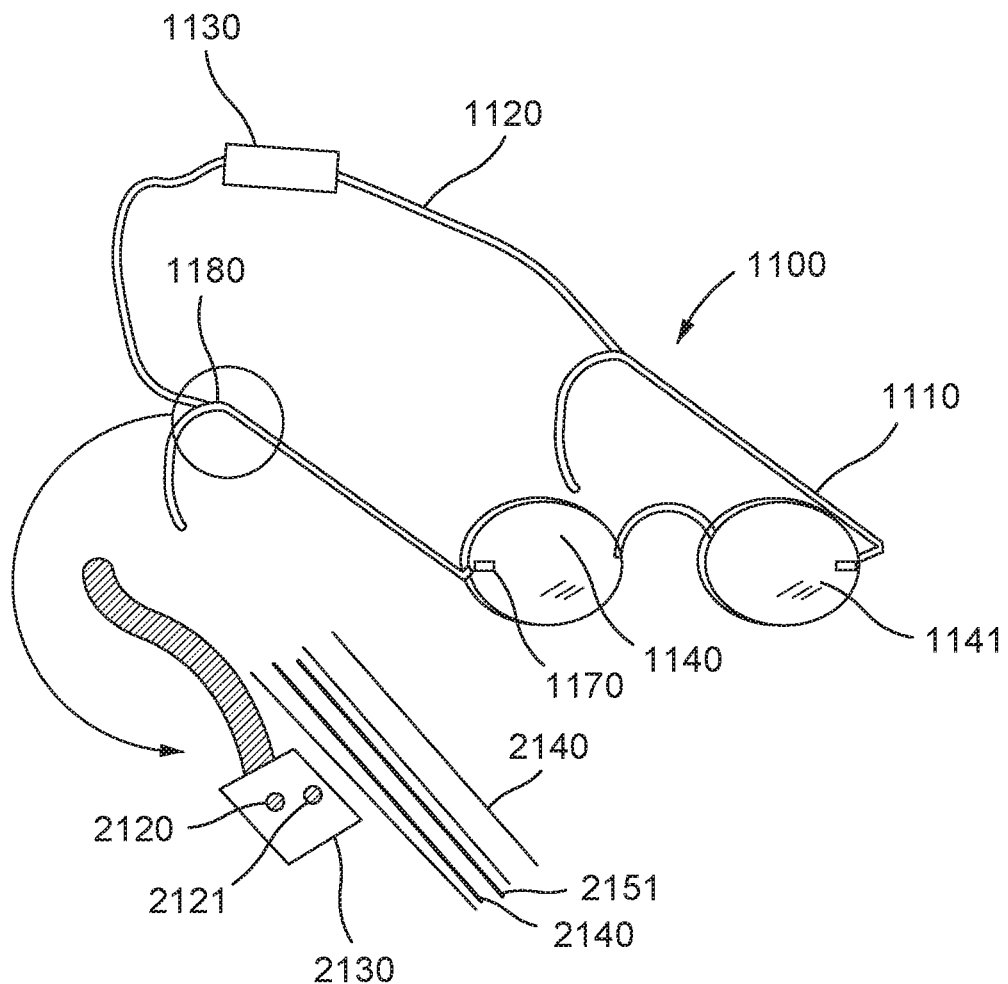
FIG. 21 illustrates another exemplary eyewear system including a magnetic connection to the frame temple or frame stem according to further aspects of the invention.

FIG. 21 illustrates a magnetic connection to the frame temple or frame stem. In this case electrical contact points 2120, 2121, within the magnetic tab 2130 on the tether 1120 make electrical contact to the two bus bars 2150, 2151 on the frame stem 2140. Two insulated bus bars on the frame stem may be used to prevent shorting of the power source when making contacts.

FIGS. 22A-22D illustrate yet another embodiment where the spectacles may be powered and controlled. In FIG. 22A, a power supply and/or controller 2210 is connected to a pair of spectacles via two connection points 2220, 2221 on the frame stems 2240, 2241 to cables or tethers 2230, 2231 running from the power supply/controller. The details in FIG. 22B illustrate a combination of pins 2260 and holes or receptacles 2261 in addition to magnetic contacts 2263, 2264. The side view in FIG. 22C illustrates the conductors 2267, 2268 within the tether 2231 or 2230 coming from one side of the connection point with pins, and conductors 2265, 2266 within the frame stems 2240, 2241 with receptacles 2261. FIG. 22D shows, as added mechanical security, a rubber flap 2280 with an expandable small slit or hole is mounted to the tether 2230, 2231 and slides over a pin 2290 mounted on the frame stems 2240, 2241.

Figure 23A:
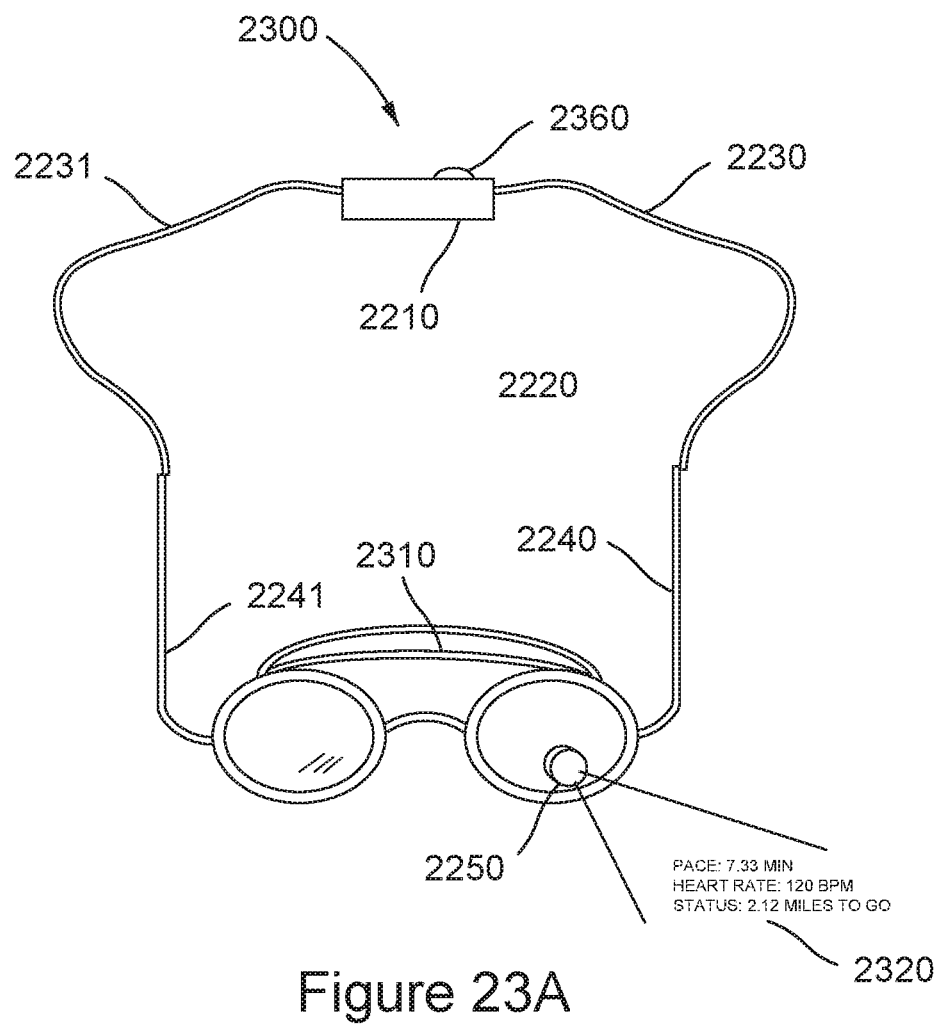
FIGS. 23A and 23B illustrate another exemplary eyewear system, including an optical viewing visor, according to further aspects of the invention.
Figure 23B:
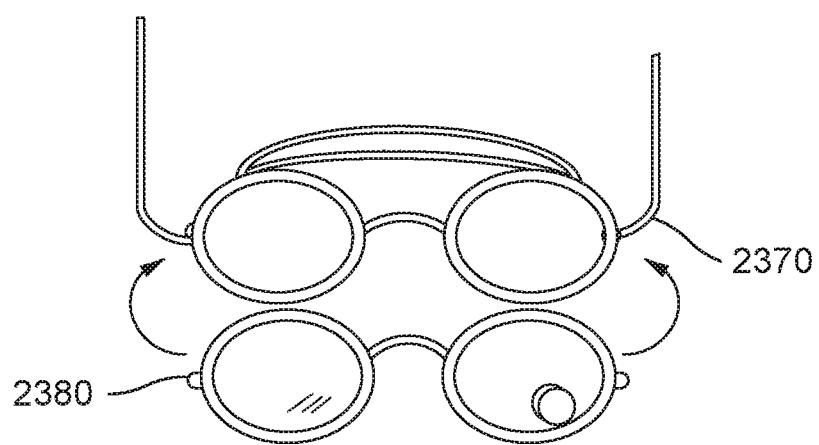

FIG. 23A illustrates another embodiment. In this case a visor 2310 is added to a pair of sports goggles with an optical display viewer 2250, where said viewer is used to display important information to the individual n training, in this case, the pace, the heart rate, and the distance left in the race. This allows the runner to check his critical information without having to break stride to look at a wrist-worn device as is normally done today. The controller may also include a small camera 2360, which would allow the user to view what is behind them in the optical display viewer 2250. FIG. 23B illustrates the embodiment of FIG. 23A as a clip-on device. Here the clip-on 2380 includes the micro-optical display that is powered and fed data via attachment to the frame 2370. Attachment may be via any of the methods described herein.

FIGS. 24A-24F illustrate embodiments where any electronic lens, by way of example only, an optically variable and/or focusing lens as is the case of an electro-active, electro-fluid, electro-pressure, electro-mechanically moving lens system, and also that of an electro-chromic tinted lens, etc.) may be snapped over or clipped onto the front of a conventional pair of lenses 2430 that may contain the patient's conventional distance Rx. This can be accomplished by either affixing the electronic clip-ons to the lenses 2430 or to the frames 2420. Since the distance Rx will take into consideration any astigmatic correction, the placement of the electronic lens, such as by example only, an electro-active focusing optic, can be more forgiving regarding its orientation within the frame. Such an electro-active lens is described in the following U.S. Pat. Nos. 6,491,391, 6,491,394, 6,517,203, 6,619,799, 6,733,130 and 6,857,741. Moreover, this would greatly reduce the complexity of providing electro-active focusing correction where both the distance and near correction are required.

Figure 24A:
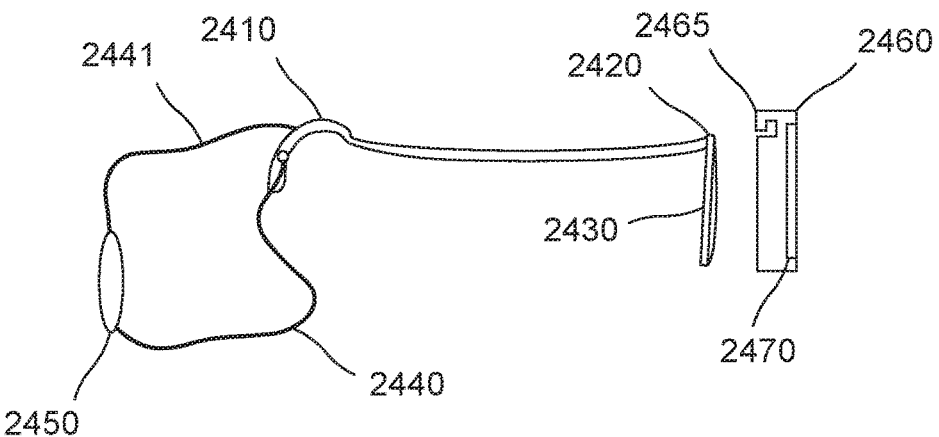
FIGS. 24A-24G illustrate another exemplary eyewear system, including adjustable lenses, according to further aspects of the invention.
Figure 24B:
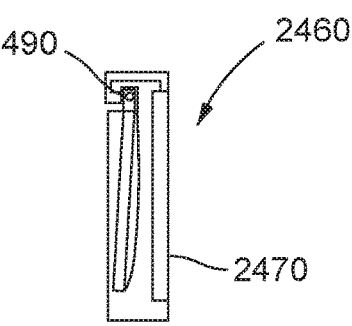

By decoupling the fixed lens from the electro-active lens, an electro-active focusing lens product could be offered with far fewer SKUs. In fact, the invention anticipates having a limited line of electro-active focusing electronic clip-ons that have preset decentrations. By way of example only, the electronic clip-ons could be available with near vision inter-pupillary measurements of 63 mm, 60 mm and 57 mm, as shown in FIGS. 24D, 24E, and 24F, respectively. The proper clip-on would be selected depending upon the patient's near vision inter-pupillary measurement. Until the electro-active lenses are activated by electricity, there is no near optical power and therefore, the base conventional lens 2430 contained within the eye glass frames 2420 provides the patient's distance vision/inter-pupillary measurement set within the eyewear 2420 and functions properly for distance vision. However, when the electronic clip-ons now become activated, the electro-active lenses focus for intermediate or near vision. The resulting inter-pupillary measurement then becomes the selected electronic clip-on having a preset inter-pupillary measurement. In this manner the optician may order the appropriate decentration for the optics within the electronic clip-on based on his measurement of the patient's inter-pupillary distance.

While the above discussion was directed to electro-active focusing near and intermediate lenses, it should be pointed out that the invention contemplates electro-active lenses that are full or partial pixilated lens(es), full or partial diffractive lens(es) or a combination of both. In addition, the invention contemplates the electronic clip-ons or electronic snap-ons that house an electroactive lens or lenses that corrects for only higher order aberrations. The electronic clip-on or electronic-snap on would be used to allow the patient to see better than 20/20, perhaps better than 20/10 by correcting his or her higher order aberrations. In this case, the inter-pupillary measurement would be set for one's distance vision needs. This proper inter-pupillary measurement would be properly established by way of the location of the higher order aberration correction location within each clip-on lens. It should be pointed out that in this inventive embodiment the clip-on correcting the patient's higher order aberration(s) can be that of either a fixed static non-electronic lens or that of an electronic pixelated lens.

The power source and/or controller 2450 is attached to the electrifiable frame temple 2410 in any of the manners described herein. The electronic snap-on or electronic clip-on device 2460 containing the electro-active elements 2470 is slightly over-sized to that of frame 2420 so that the side of the conventional lens is covered from view by a person looking at the side of the frame. FIG. 24B illustrates the snap-on device 2460 in place over the frame with at least one electrical contact 2490 being made from the frame to the electro-active element 2470 within the snap-on device 2460. The connection to the frame may also be done with magnets. These magnets can be contained within the frame 2420 and/or in the electronic clip-on 2460. The magnets can be positioned to attach the electronic clip-on 2460 to the frame 2420 either at the top, bottom, front, middle, sides or any place on the frame 2420 or the electronic clip-on 2460.

Figure 24C:
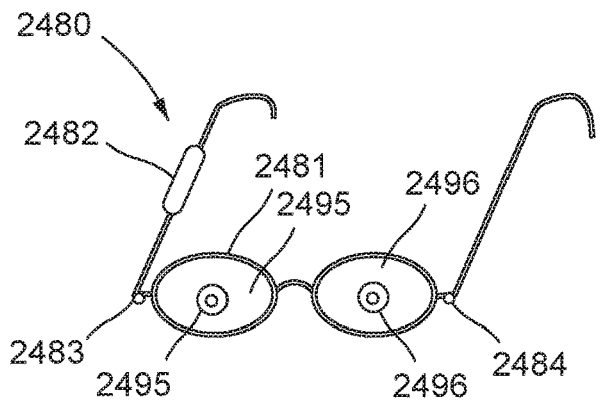
Figure 24G:
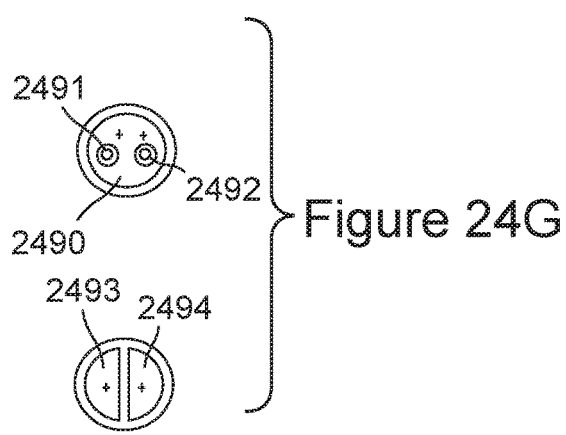
Figure 24D:
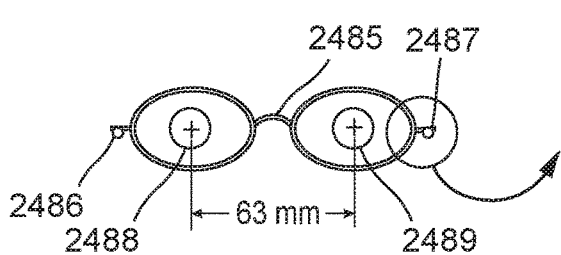
Figure 24E:
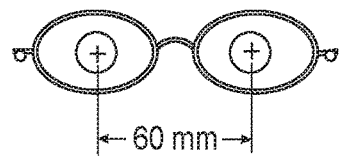
Figure 24F:
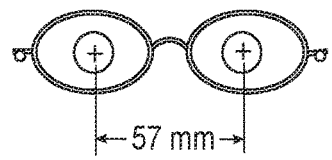

FIGS. 24C-24D further illustrate the inventive embodiment of using an electronic clip-on that attaches to an electronic conducting frame to power electro-active lenses 2488 and 2489. A pair of spectacles 2481 designed to be used with a pair of electronic clip-on lenses 2485 is shown. In this case, the electronic frame may include a power source 2482 located anywhere on the electronic frame.

Connection points 2483, 2484 that are either mechanical of magnetic are located on the electronic frame 2481. The electronic clip-on lenses 2485 also include connection points 2486 and 2487 similar to the ones on the electronic frame. The electronic clip-on lenses may include electro-active lenses 2488, 2489 for electronic focusing to supplement the focusing power of the fixed lenses 2495, 2496 located in the electronic frame 2481. In other inventive embodiments, the electronic lenses may be electrochromic lenses that create a variable, electronically-controlled tint or a combination of an electro-chromic tint and electro-active focusing lenses to either correction higher order aberrations, provide presbyopia correction, or focus for conventional needs, for that matter.

The details in FIG. 24G illustrate two possible electrical connections using magnetic physical attachment means. In one case a single magnet 2490 is placed in the connection point and a positive 2491 and a negative 2492 electrical terminal connection are placed inside the magnet 2490. The same configuration would be used on both the electronic frame 2481 and electronic clip-on lenses 2485. Alternatively, since most magnetic material can also be electrically conductive, the physical connection can be done with a split magnet, where one half-of-the magnet 2493 forms the positive electrical terminal 2493 and the other half 2494 forms the negative electrical terminal. In this case, the half-magnets would need to be electrically insulated from each other. While FIGS. 24A-24G illustrate what amount to essentially temporary attachment of electrically activated lenses, the electronic clip-ons could be permanently affixed to the frame by any number of methods including adhesive bonding, for example.

Figure 25:
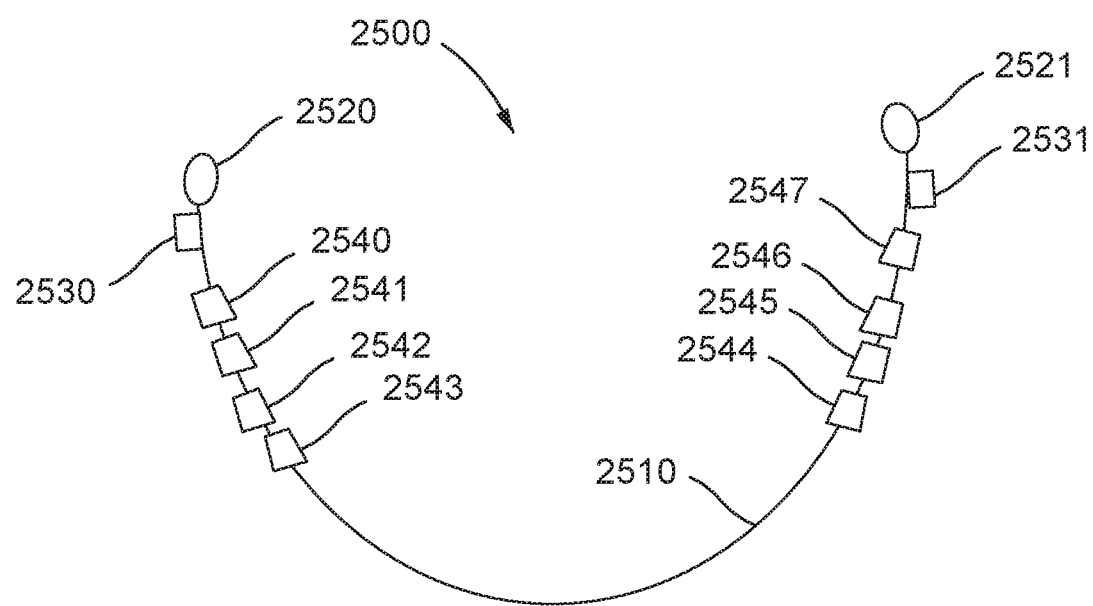
FIG. 25 illustrates an electronic chain according to further aspects of the invention.

FIG. 25 illustrates an inventive electronic chain 2510 that could be worn by women in association with electronic reading glasses. In this case, in addition to loops 2520 and 2521 to connect the chain to the frame, this chain has multiple decorative beads 2540 thru 2547, any of which may comprise a power source for powering an electro-active spectacle. The shape and design of the decorative beads or jewelry is such to hide the power source that is contained within. Magnets 2530, 2531 may be used to establish electrical connection as described earlier, or other mechanical connections as described herein may also be employed.

Figure 26:
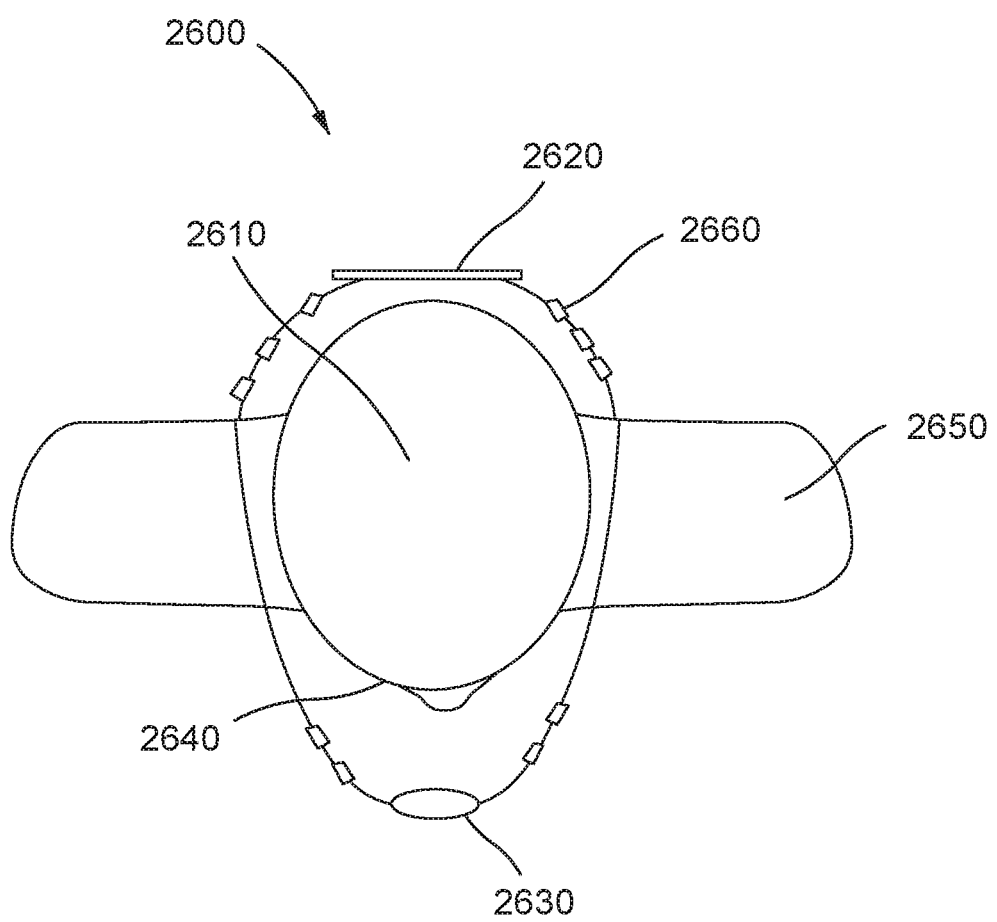
FIG. 26 illustrates an electronic chain with a pair of electronic reading glasses according to further aspects of the invention.

FIG. 26 illustrates an electronic chain with a pair of electronic reading glasses 2260 that may include electro-active lens functions. The electronic reading glasses in this case may be worn behind the head 2610 when not in use. In this inventive embodiment a power source/controller 2630 designed to look like a decorative locket or any other piece of jewelry may be placed in front of the wearer 2640 when the glasses are not required. In this manner the wearer can have a decorative necklace when reading glasses are not required. Further, if the reading glasses have electrical functionality, then the power and/or control is available.

FIGS. 27A-27D illustrate embodiments whereby small earplug speakers 2730 and 2731 are connected to an electrical tether containing audio signals from a music player or other audio device 2710 via slides 2720 and 2721. Details in FIGS. 27B and 27C illustrate alternative center attachments to those-currently used in the art. FIG. 27D illustrates a charger shaped like a human nose, that can be used to charge the battery for the controller stored in the enclosure on the tether. By plugging both or either end of center connections into the nose shaped charger the battery can be recharged. This would eliminate the need for charging electronics in the controller that is worn behind the neck. It should be pointed out that the invention contemplates the audio device 2710 being that of, by way of example only, an Apple iPod®, MP3 player, Audio Cassette, Satellite Radio, conventional radio, pager, cell phone transceiver, micro-DVD or digital video file player, video transceiver, etc.

FIGS. 28A-28C illustrate alternative inventive methods of breaking the connection in the device described in FIG. 27. In this case the connection is done on one side of the electronic spectacle frame with either magnets 2820 as shown in FIG. 28B, or with a pin 2840 and a receptacle 2830 as shown in FIG. 28C.

Figure 29A:
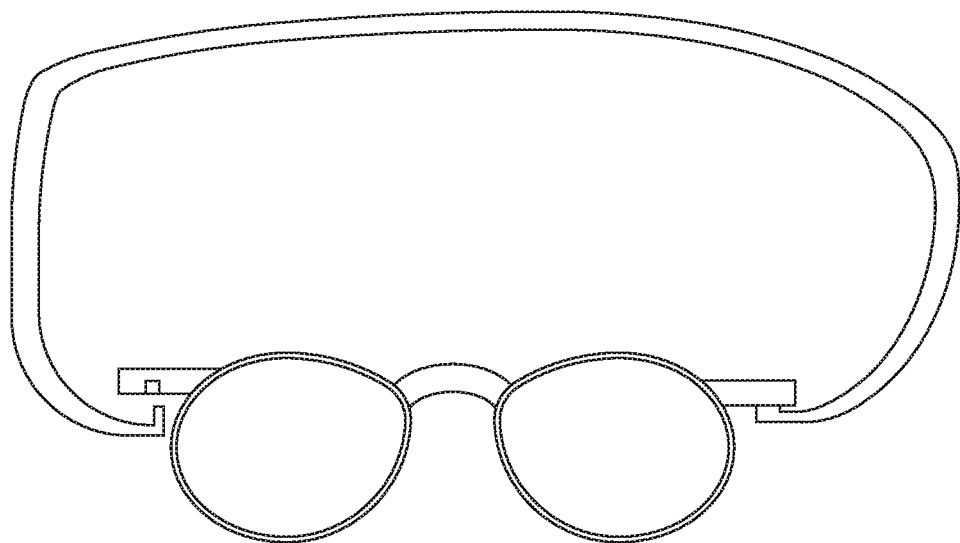
FIGS. 29A and 29B illustrate further embodiments including one or more temple connectors, according to further aspects of the invention.
Figure 29B:
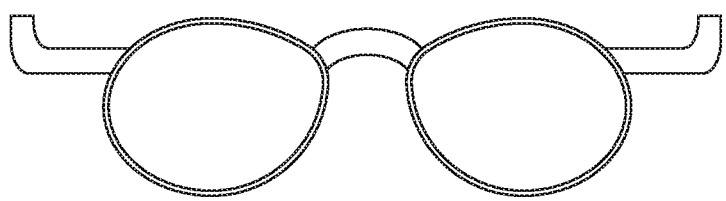

FIGS. 29A and 29B illustrate additional attachment embodiments. In FIG. 29A, a single connection point is made with a pin on one side of the front of the spectacles. In this case, it can be on the front, back, side, top, or bottom. However as shown in FIG. 29A, the preferred attachment in this embodiment is on the bottom of the electronic eyewear. In FIG. 29B the electronic frame is shown where connections like the ones illustrated in FIGS. 28A-28C and 29A may be made on both sides of the front of the spectacles.

Figure 30A:
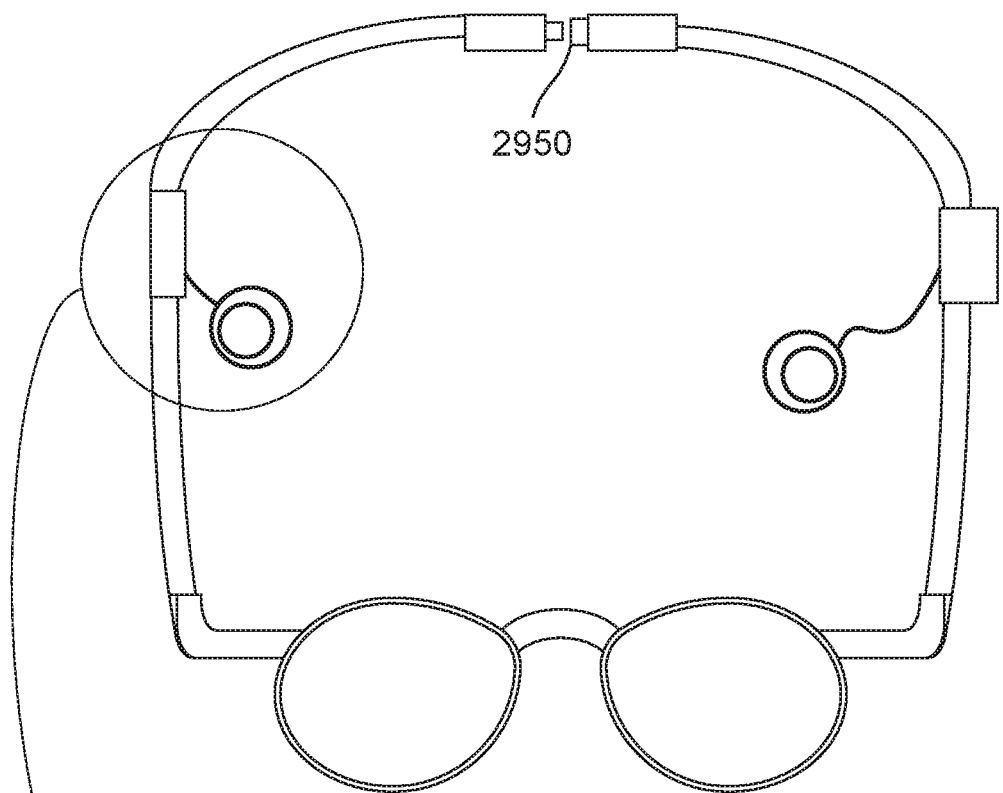
FIGS. 30A and 30B illustrate another exemplary eyewear system, including audio connectors, according to further aspects of the invention.

FIG. 30A illustrates further embodiments similar to that described in FIG. 27, whereby the connection point 2950 is in the back of the device as opposed to the bridge of the spectacles. It should be pointed out that in each of these cases of FIGS. 27A-27D, 28A-28C, 29A, 29B, and 30A, the manner in which the electronic connection is made can allow for charging, and can allow for an easy manner of putting on and taking off the inventive electronic eyewear disclosed herein.

Figure 30B:
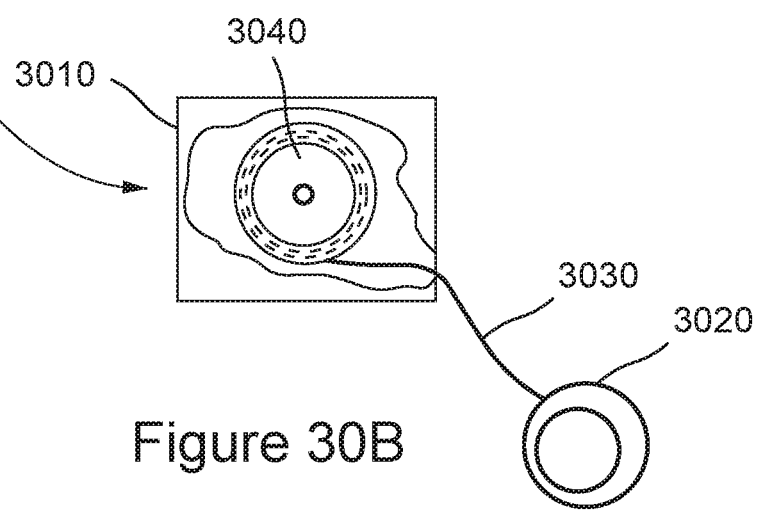

FIG. 30B illustrates an embodiment whereby a housing 3010 is used to store extra audio cable 3030 for the earplug 3020 on a spring loaded spool 3040. In this manner the length of the audio cable can be adjusted for different users. Moreover, this would also allow the wearer to still use the audio features of the invention while not wearing their electronic eyewear on their face, for example, when they are just letting the electronic eyewear hang over their neck.

Figure 31:
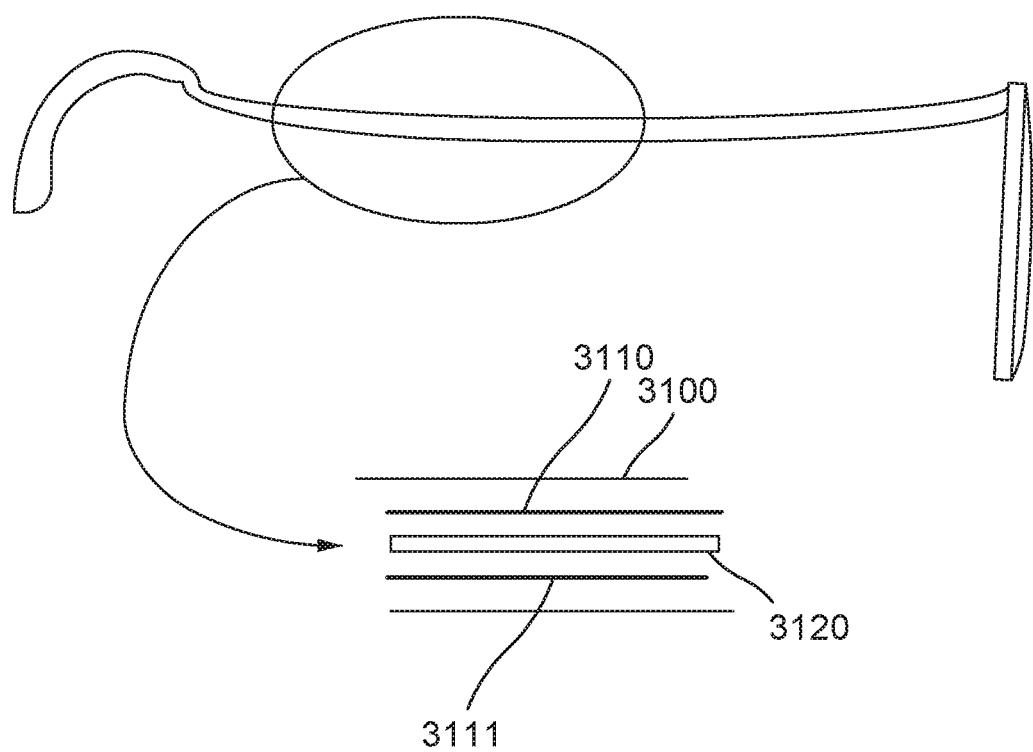
FIG. 31 illustrates an embodiments in which two electronic conductive buses or wires run along the inside wall of an electronic frame stem or temple according to further aspects of the invention.

FIG. 31 illustrates an inventive embodiment whereby power and/or audio signals may be sent down the inside wall of an electronic frame stem or temple 3100. Two electronic conductive buses or wires 3110 and 3120 run along the inside wall of the electronic frame stem or temple 3100. A magnetic or metal strip capable of magnetic attraction 3120 runs down between the two buses. In this manner, power or audio can be provided to a device connected to the electronic frame stem or temple. As an alternative to magnetic connection, a track system similar to track lighting may also be used to secure attached devices to the electronic frame stem or temple. This method of electrical connection and mechanical connection may also be used on the electronic chains and electronic tethers described in the present invention.

Figure 32:
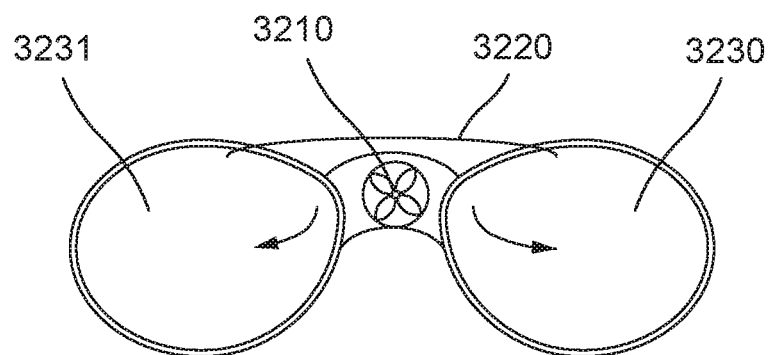
FIG. 32 illustrates another exemplary eyewear system, including a fan in the bridge of an electronic frame, according to further aspects of the invention.

FIG. 32 illustrates an inventive embodiment where a small fan 3210 is placed in the bridge 3220 of an electronic frame to blow cool air over the inside surfaces of the lenses 3231 and 3230 to prevent fogging during sports activities. To date most efforts to mitigate fogging have be marginal. While there are antifogging solutions that can be applied to the lens surface, depending upon the level of activity, the fit of the eyewear, and the ambient temperature when the glasses are worn, lenses still fog and thus create visual problems for wearers. Since electrical power will be available with the present inventive eyewear described herein, an electrically powered fan would solve the fogging problem very effectively. In this case the air flow is directed by the design of the frames bridge to flow to the fog affected areas of the lens. In most cases this area is the most nasal, inside, sections of the lens. The invention anticipates external deflectors and internal channels that direct the air from the fan. Alternatively transparent conductive heating elements fashioned from a transparent conductive layer, such as, by way of example only, ITO or conductive polymer, may be placed in the lens and could be used to drive fog off the lenses in conditions where fogging is likely to occur.

Figure 33:
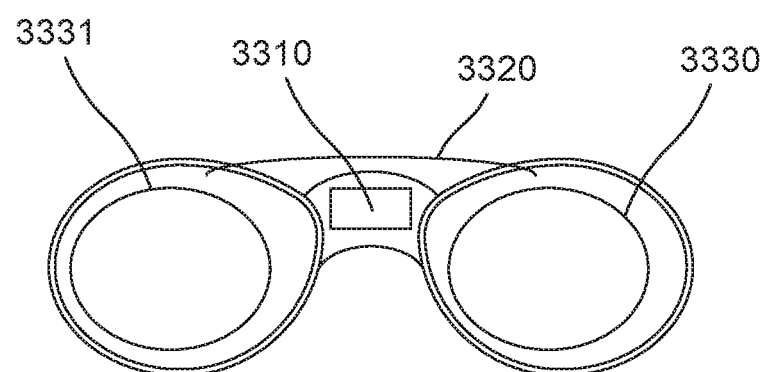
FIG. 33 illustrates another exemplary eyewear system, including a self-contained electronic clip-on module, according to further aspects of the invention.

FIG. 33 illustrates a self-contained electronic clip-on or electronic snap-on that may be used in spectacles or sports goggles. In this inventive embodiment the electronic clip-on would include a power supply. Controller 3310 is in the center portion of the clip 3320 for controlling and powering the electro-active elements 3331 and 3330. In this inventive embodiment, the self-contained electronic clip-on can be used not only to power the electronic lenses contained within the electronic clip-on but also that of other electronic features contained within the electronic frames or the inventive self contained electronic clip-on can be used to solely power the electronic lenses, by way of example only, electro-active focusing lenses or electro-chromic lenses that are housed within the electronic clip-on.

It should be pointed out that nearly all the inventive embodiments described herein can be made to work with rimmed frames, rimless frames, hinged temples, and hingeless temples. Also, the present invention described herein could also be used with Clic Goggles™ that utilize non-electronic eyewear that joins together at the frame bridge to form a frame from two separate eyewear pieces that are connected by way of a tether in the back. This tether secures the Clic Goggle™ eyewear to ones head after the two eyepieces are attached at the bridge. Additionally, the present invention includes electronic and non-electronic connections made by magnetic means, mechanical means, utilizing pins and friction fits and other physical connection techniques, including the combination of magnetic and mechanical connections.

Figure 34:
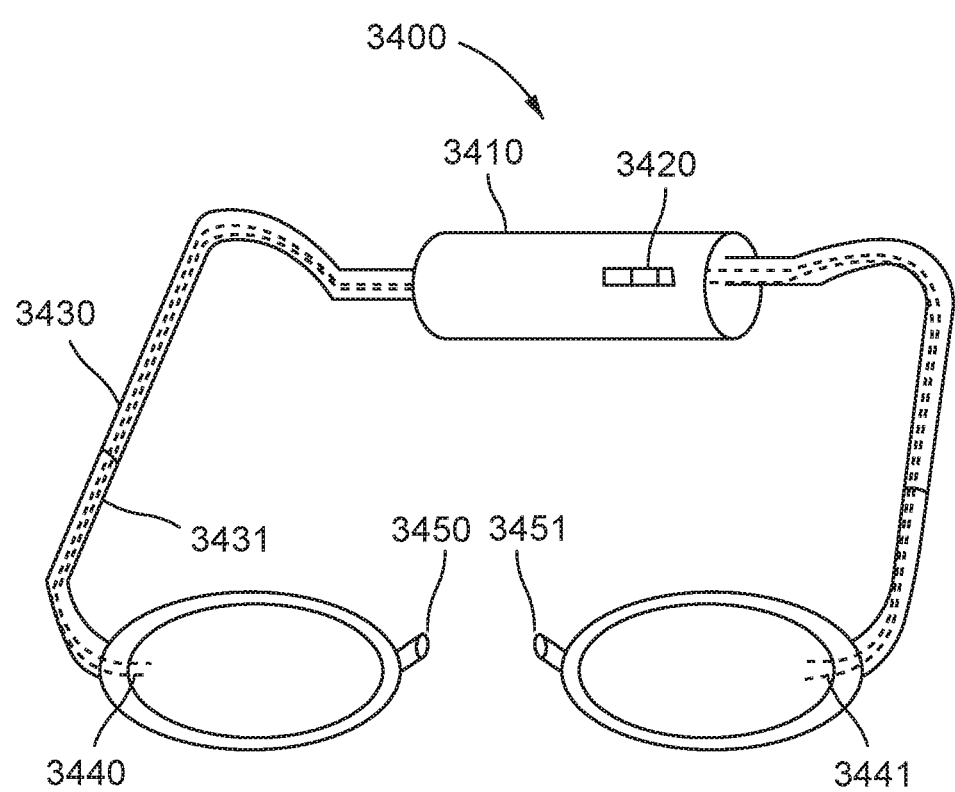
FIG. 34 illustrates another exemplary eyewear system according to further aspects of the invention.

FIG. 34 illustrates an inventive embodiment whereby a pair of spectacles 3400 similar to the branded Clic™ spectacles is redesigned to provide power to electronic lenses, by way of example only, electro-chromic sunglasses, electro-active focusing lenses, or electro-active supervision lenses that correct for higher order aberrations. In this embodiment, a power source, by way of example only, a battery, fuel cell, solar panel) is placed in an enclosure 3410 that is attached to the back portion of the electronic frame tether 3430. The power can be turned on or off with a small switch 3420 on the enclosure. Two pairs of conductors 3440 and 3441 extend from the power source inside the enclosure 3410 to provide power to whatever type of electronic lens is placed in the front portion of the electronic frame 3431.

The electronic stem or temple on the front portion of the electronic frame 3431 is sized to fit into the stem on the back portion of the electronic frame tether 3430. In the Clic™ product, the stems or temples on the front portion of the frame are solid plastic. In the present invention, these stems or temples become electrical stems or temples and need to be either hollow to allow for the conductors 3440 and 3441 to be extended down to the lenses, or electronic connections can be applied to the external surface of the stems or temples as taught in FIG. 13.

The conductive pairs may be as long as the fully extended length of the electronic frame stems or temples and may be flexible so that they do not break or crack when the front stems are pushed all the way into the back electronic frame stems or temples. A similar set of mechanical locks (not shown) can be placed in the electronic frame stems or temples to hold the position of the front frame stems or temple sections to that of the back frame stems or temples sections. The present invention may join together at the bridge of the nose with any number of methods described herein, including magnets 3450 and 3451.

Utilizing the inventive embodiment allows for a continuous end-to-end electrical circuit that is never disconnected when the electronic eyewear is taken off and decoupled. In this inventive embodiment, the electrical connection to either the speakers, the electronic lenses or the electronic clip-ons remains intact. When utilizing a product where the connection is in the front eyewear bridge, two monocular electronic clip-ons may be used. In this case, each monocular electronic clip-on is applied separately so that it is possible to decouple the eyewear in the bridge without having to take off the clip-on first. However in still other embodiments, a one piece binocular electronic clip-on is used and when this occurs the binocular clip-on may be removed prior to decoupling the eyewear.

Figure 35:
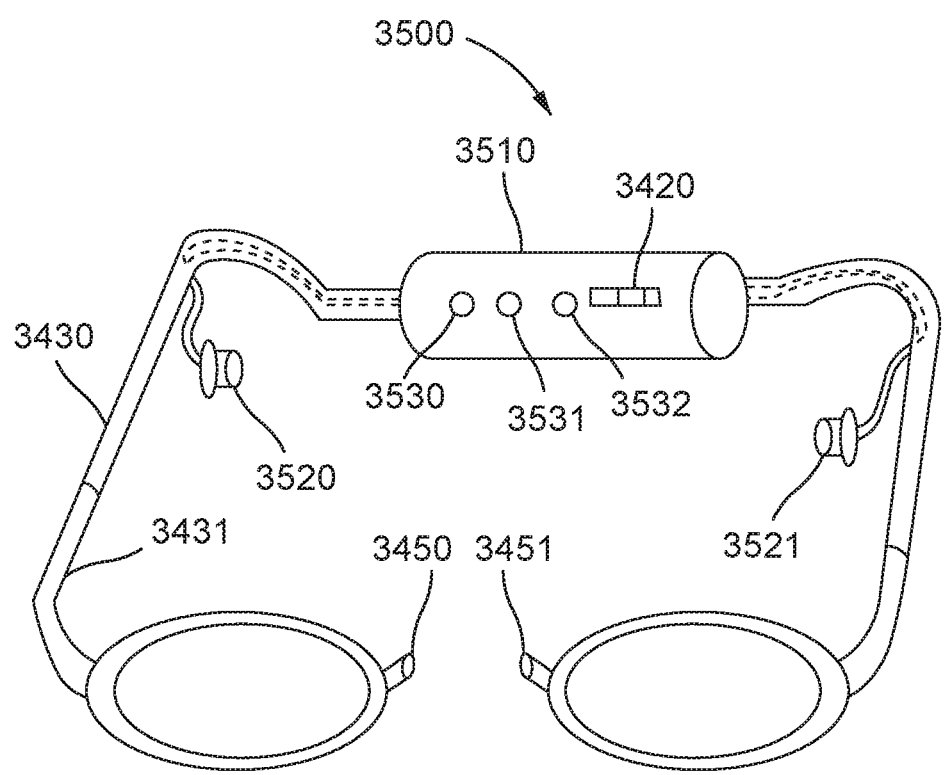
FIG. 35 illustrates another exemplary eyewear system, including an electronic device placed on the back portion of the electronic frame tether, according to further aspects of the invention.

FIG. 35 illustrates yet another inventive embodiment whereby an electronic device 3510 is placed on the back portion of the electronic frame tether 3430. Types of devices that may be placed on the back of the electronic frame tether include, by way of example only, an MP3 player like the Apple iPod®, a small terrestrial radio, a small satellite radio, or a small cell phone or paging device. Small buttons 3530, 3531 and 3532 may be placed on the outside of the electronic device to control it. For example, one button might change the volume of the sound sent to each earplugs 3520 and 3521 attached to the electronic device through the electronic frame stems or temples. Other buttons could be used to change the track that is being played on an audio device. Any number of functions may be addressed via numerous buttons placed on the outside of the electronic device 3510. In the case where the small electronic device is a cell phone, the earplugs could be fitted with microphones (not shown) to allow the user to send talk into the cell phone. In-ear, microphones are well known in the cell phone accessory art. Also, in the case of a cell phone, it would be advantageous to use voice recognition to perform dialing and other functions normally done on a keypad, since the cell phone will be behind the users head in the present invention.

Figure 36A:
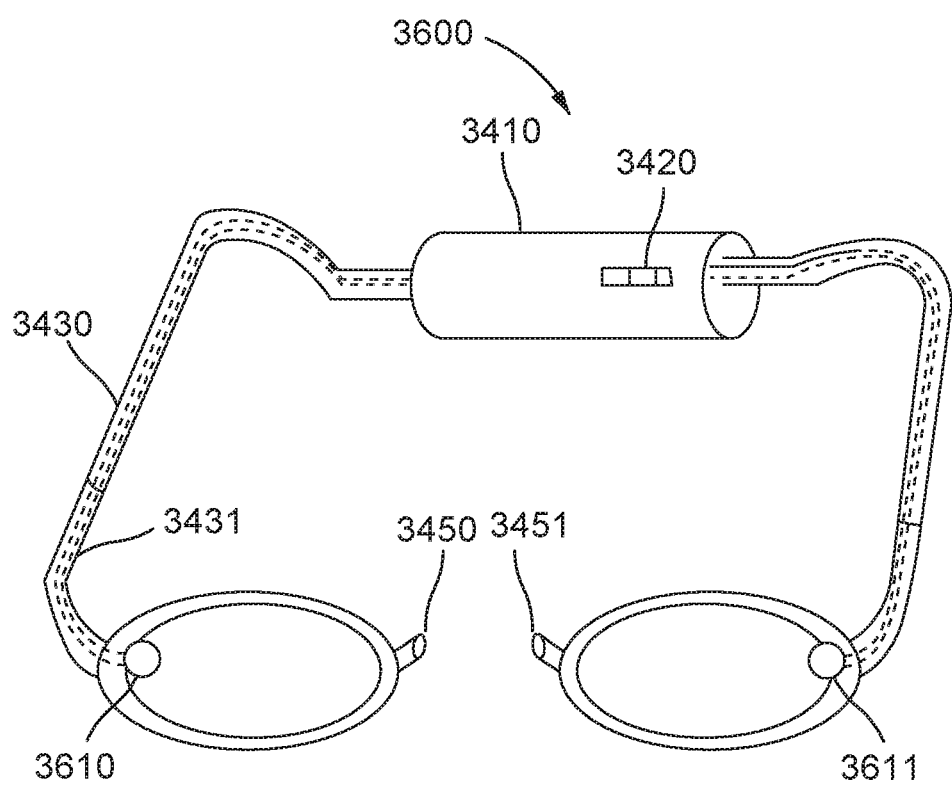
FIGS. 36A and 36B illustrate another exemplary eyewear system, including lights placed near the front of the frame, according to further aspects of the invention.

FIG. 36A illustrates an inventive embodiment whereby two small lights 3610 and 3611 are placed near the front of the frame close to the lenses to provide reading light in dark places such as restaurants. This is particularly important for wearers who suffer from presbyopia. The lights would be powered by the power sources described in the discussion of FIG. 34. Attachment of the conductive pairs to the light sources could be done with any of the methods described above, including simply soldering the wires to the two terminals of the light source. Light sources may include by way of example only, small incandescent light bulbs or LEDs (preferably white). It should be pointed out that the battery or power source can be also placed anywhere in the electronic eyewear so long as it makes the proper electrical connection with the light source. One preferred eyewear style utilized with the inventive lights would be that of electronic readers or reading glasses. However, this inventive application can be utilized for all kinds of electronic eyewear.

Figure 36B:
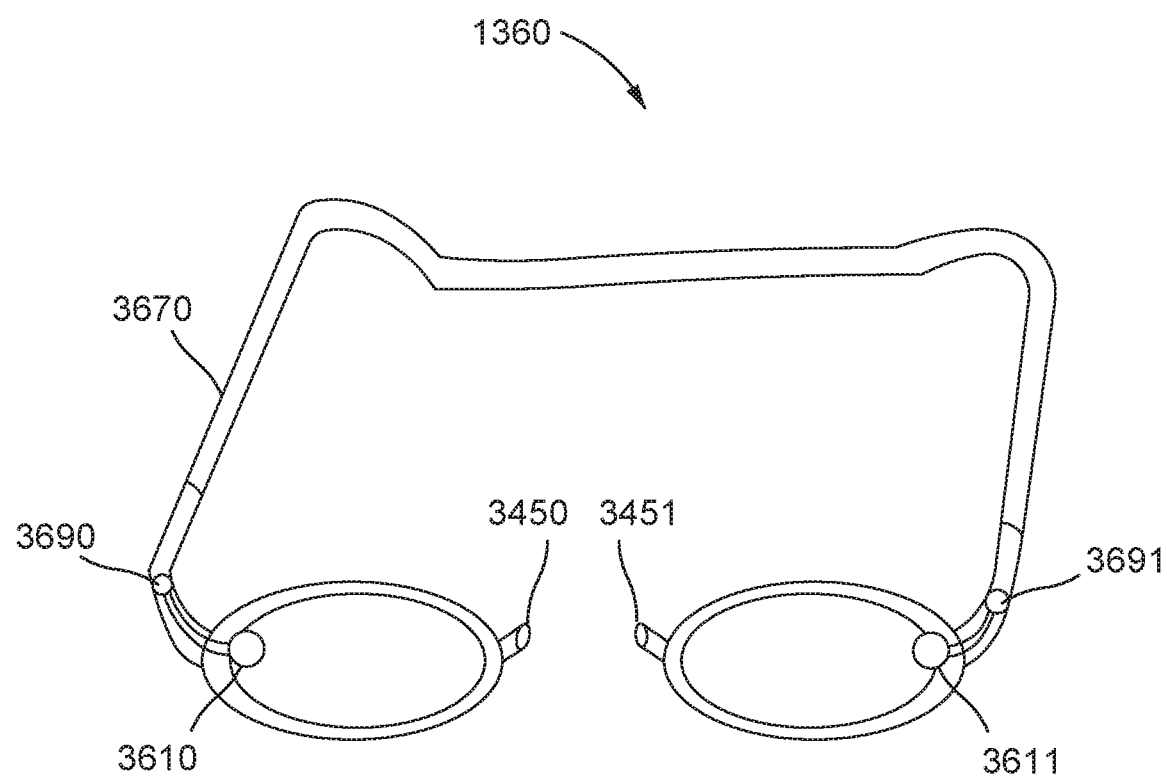

FIG. 36B illustrates a similar inventive embodiment as FIG. 36A except in this embodiment, the light sources 3610, 3611 are powered by small batteries 3690, 3691 placed in the front portion of the frame stems.

Figure 37A:
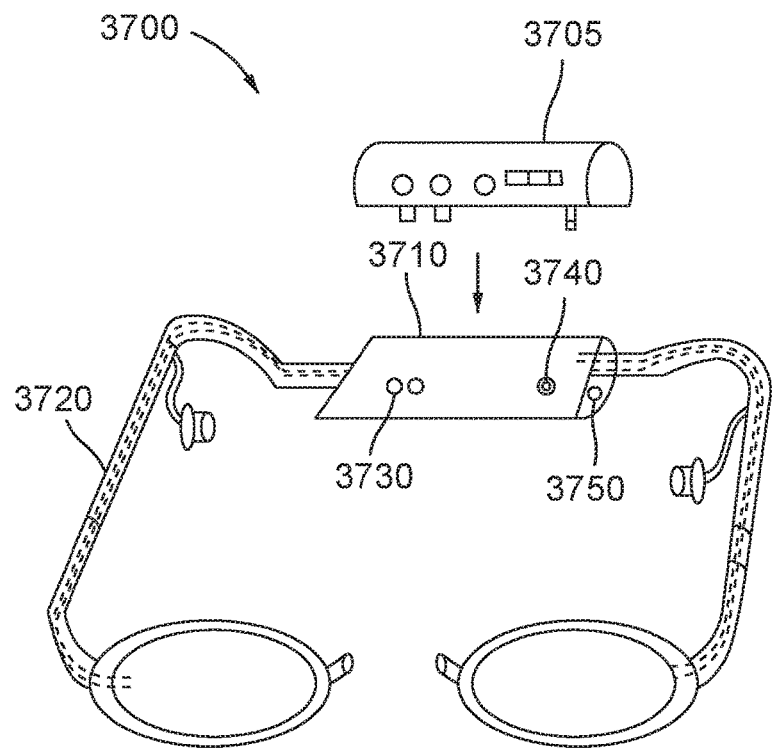
FIGS. 37A and 37B illustrate another exemplary eyewear system, including an electronic docking station placed on the back portion of the electronic frame tether, according to further aspects of the invention.

FIG. 37A illustrates an inventive electronic docking station 3710 placed on the back portion of the electronic frame tether 3720. The electronic docking station includes at least one pair of power terminal contacts 3730, and at least one audio (stereo or mono) or video connection port 3740. The electronic docking station also has a charging port 3750 where a standard charger could be connected for recharging the power source located in either the electronic docking station, or the electronic device 3705 that is to be placed in said electronic docking station or both.

While the electronic docking station in this inventive embodiment was located on the back portion of the frame tether, the docking station might also be located anywhere that makes sense on the frame, for example on the frame stem or temple. Once again it should be pointed out that any electronic audio and/or video device can be fabricated to function within the electronic docking station. These could be, by way of example only, an Apple iPod®, MP3 player, tape cassette, satellite radio, conventional radio, pager, cell phone transceiver, microDVD or video file player, video transceiver, etc.

Figure 37B:
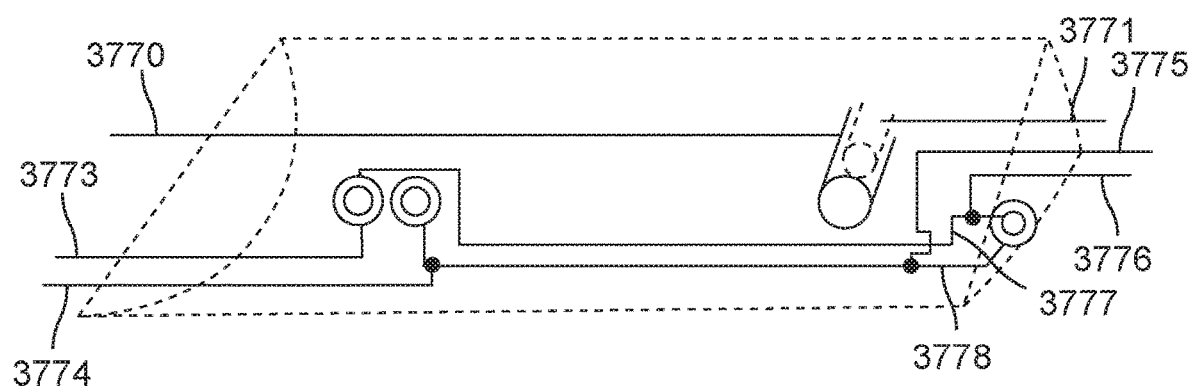

FIG. 37B illustrates a possible wiring diagram for the docking station shown in FIG. 37A. In FIG. 37B, a shielded or unshielded wire 3770 provides audio signal to the right earplug, while wire 3771 provides audio for the left earplug. Please note that the audio ground/shield wires were not shown for simplicity of illustration; however, proper grounding and shielding of audio signal wires is well known by those normally skilled in the audio art. Wires 3773 and 3774 provide power out to right lens, while wires 3775 and 3776 provide power out to the left lens. Wires 3777 and 3778 provide connection to the power terminals 3730 to the charging port 3750. In this case, power is provided by the power source on the docked electronic device. Alternatively, power could be provided by a power source on the docking station, which would result in a slightly different wiring arrangement.

Figure 38:
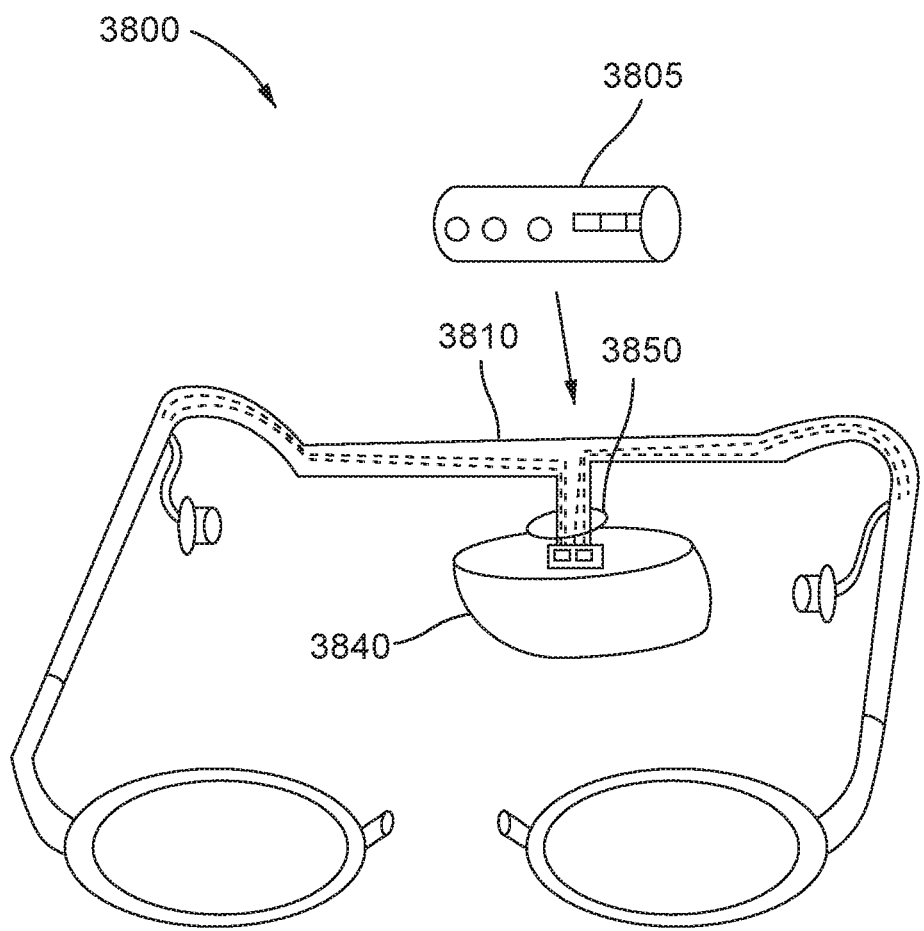
FIG. 38 illustrates another exemplary eyewear system, where the back of the electronic frame tether forms a T shape, according to further aspects of the invention.

FIG. 38 illustrates an inventive embodiment whereby the back of the electronic frame tether 3810 forms a T shape. At the bottom of the T shape, a connection point 3850 is available for attaching the electronic device 3805 to the electronic frame tether electrically and mechanically. A pouch 3840 is also attached to the bottom of the T to support the electronic device 3805. A strip of Velcro™ or double-sided tape (not shown) may be placed on the front side of the pouch so that the pouch and the electronic device enclosed therein may be affixed to the back of the wearer's shirt, thus removing any pull or heaviness of the device being hung on the electronic frame tether. Also as shown in FIGS. 15 and 16, a clip may be used to affix the pouch to the clothing being worn.

Figure 39:
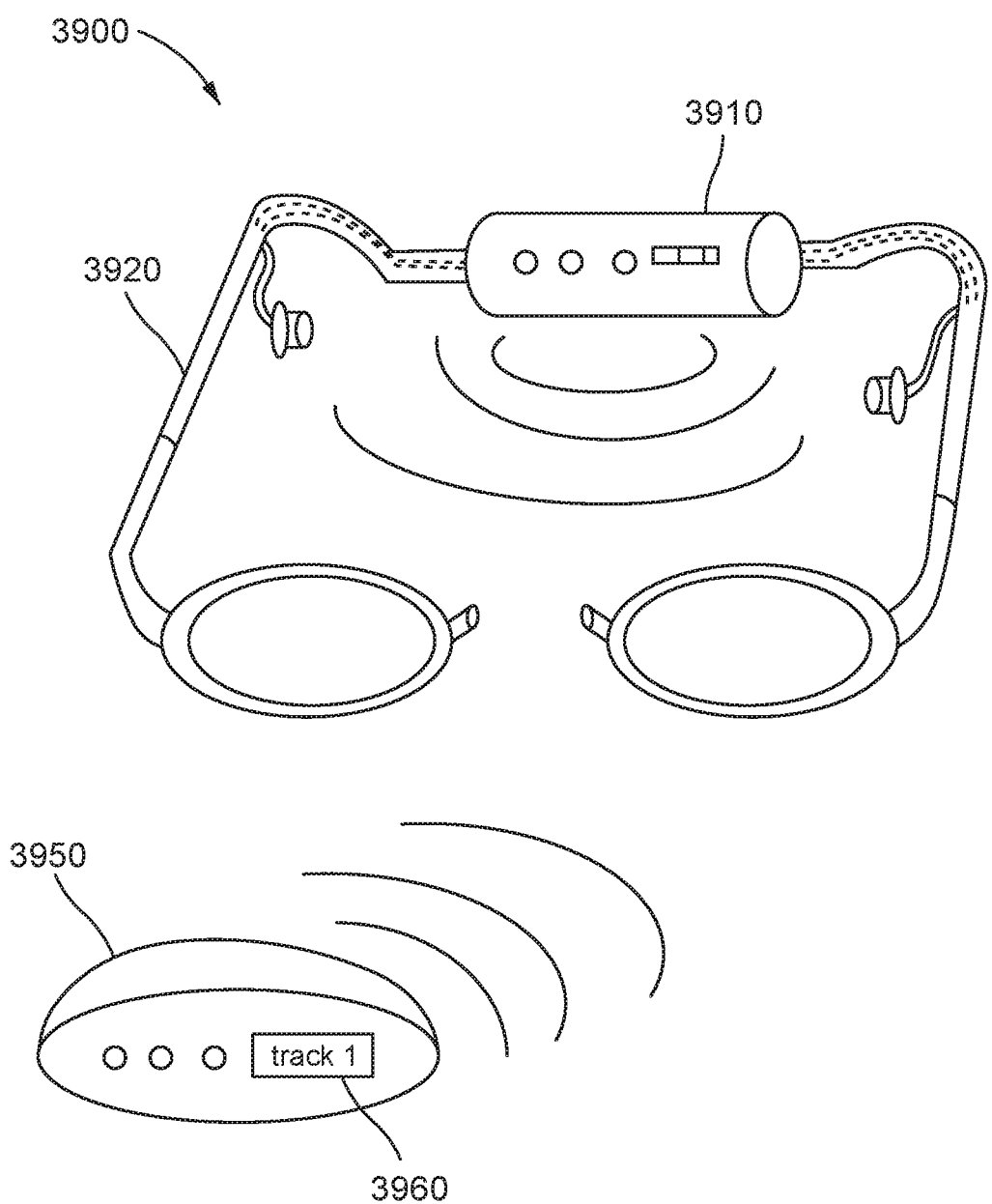
FIG. 39 illustrates another exemplary eyewear system, including an electronic device attached to the back of the electronic frame tether that may be controlled with a hand-held remote controller, according to further aspects of the invention.

FIG. 39 illustrates an inventive embodiment where the electronic device 3910 attached to the back of the electronic frame tether may be controlled with a handheld remote controller 3950 that can be held in the wearers hand. This would allow the user to control the electronic device without having to reach behind his or her head. This device may communicate via any number of known short range wireless technologies including, but not limited to, blue tooth, WiFi, or 802.11 protocol. The hand-held remote controller 3950 may include a small display 3960 to provide information regarding the status of the electronic device on the electronic frame tether. The communication between the hand held remote controller and the electronic device may be one-way or two-way depending upon the nature of the electronic device. In the case of one-way communication, it is most likely that the hand-held controller would contain a transmitter and the electronic device would contain only a receiver. In the case of two-way communication, both devices would have either a transceiver or a transmitter and a receiver.

Figure 40:
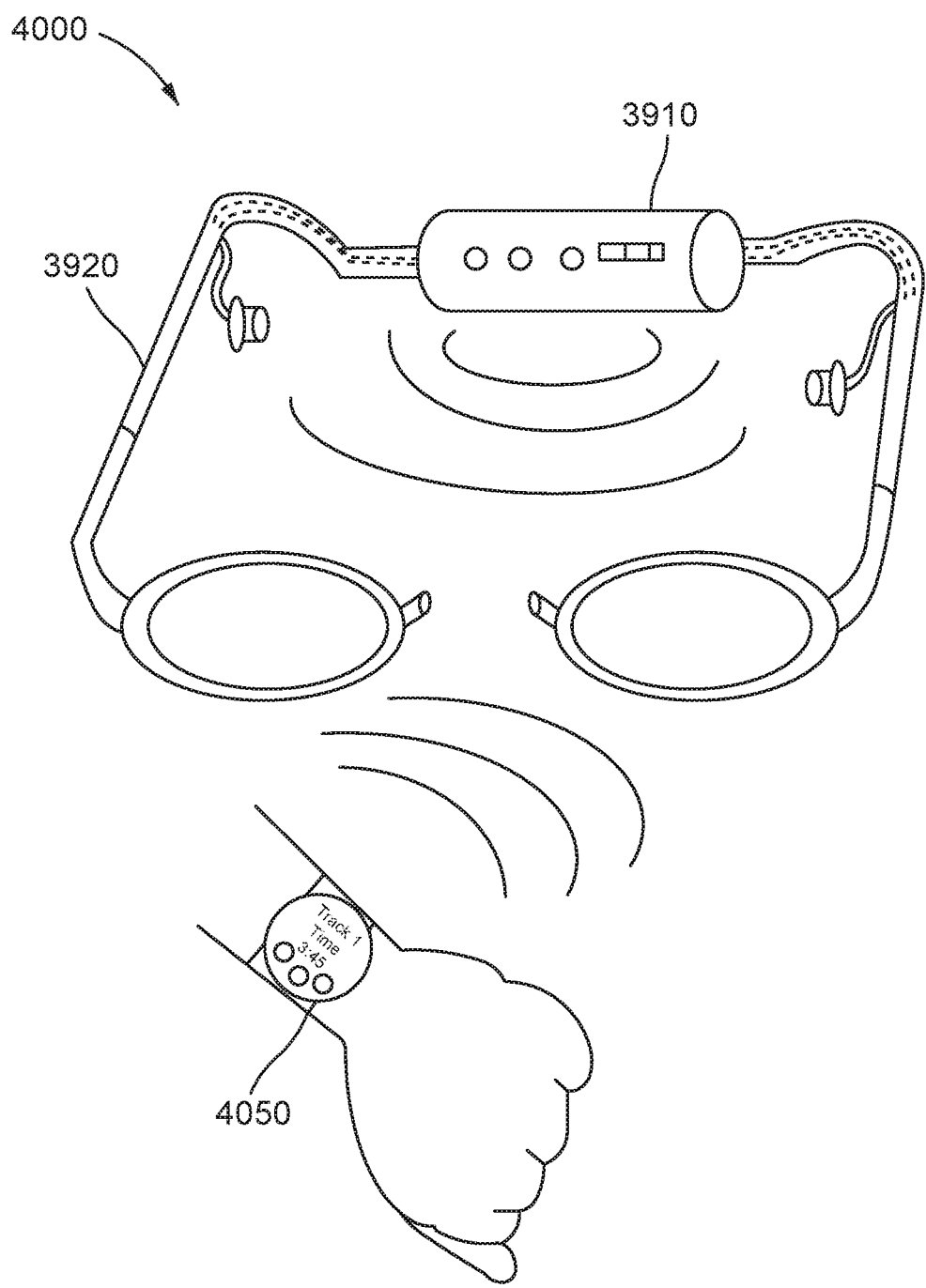
FIG. 40 illustrates another exemplary eyewear system, including a remote controller, according to further aspects of the invention.

FIG. 40 illustrates another inventive embodiment for remote control and/or communication with the electronic device 3910 placed on the back of the electronic frame tether 3920. In this case, the remote control device is that of an electronic wristwatch 4050 that not only acts as time-piece, but also functions as an effective means of controlling the electronic device 3910. It would work in a similar fashion as described above, except it would have the added advantage of being worn on the wrist. This would be particularly important for sports goggle applications where the wearer is likely to be a runner or a jogger. Once again, it should be pointed out that the device 3910 can be by way of example only, any audio and or video device such as an Apple I iPod®, MP3 player, cassette, satellite radio, conventional radio, pager, cell phone transceiver, micro-DVD player, etc.

Figure 41A:
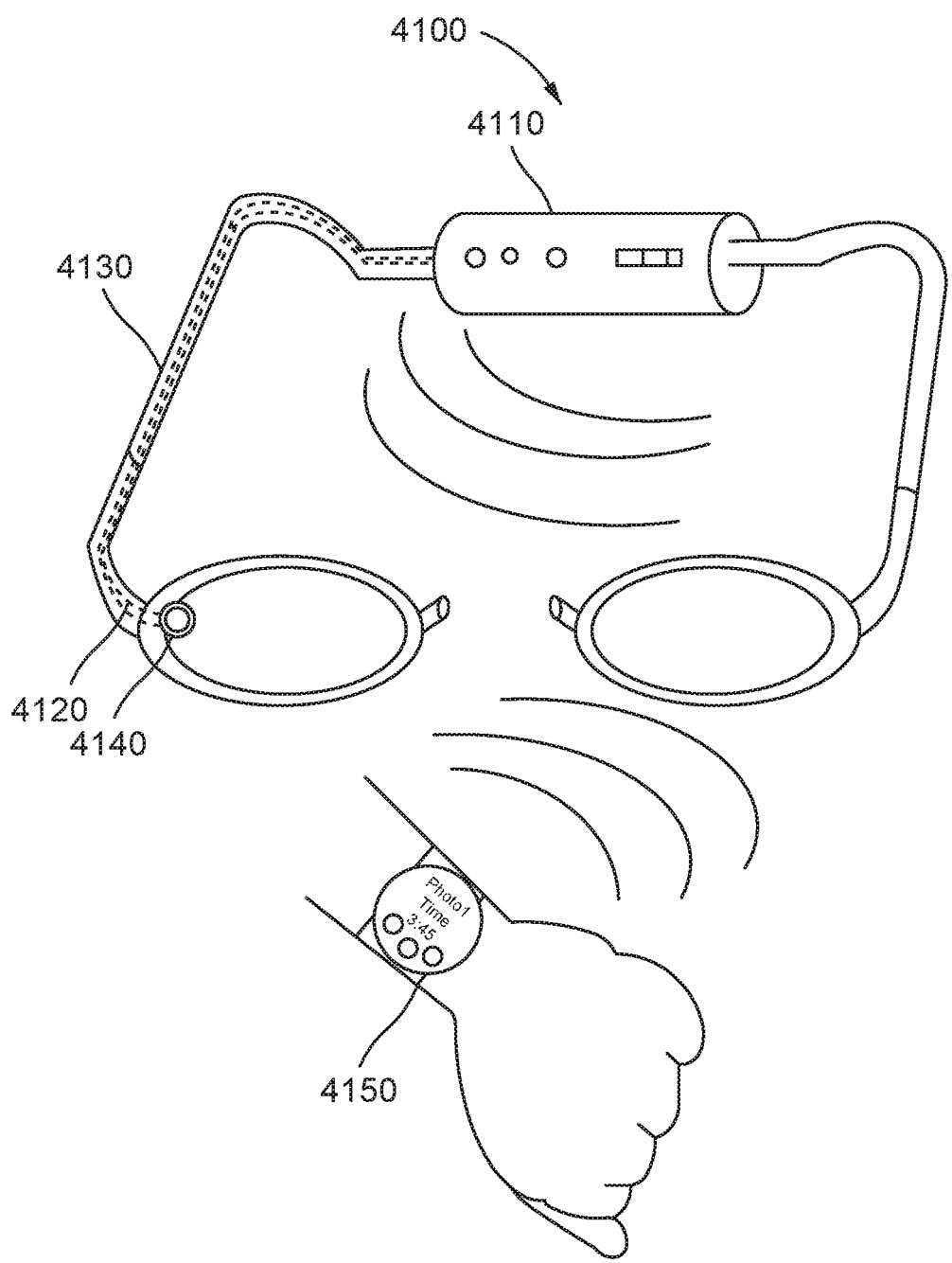
FIGS. 41A and 41B illustrate another exemplary eyewear system, including a camera that is controllable by a remote controller, according to further aspects of the invention.

FIG. 41A illustrates another embodiment for remote control and/or communication with the electronic camera or video camera 4110 placed on the back of the frame tether. This case the remote control device is a wristwatch 4150 that allows the wearer to snap photographs or to take videos of whatever he or she is looking at. A fiber optic bundle 4120 in the frame stem 4130 would pipe an image to the camera 4110 that was focused into the bundle by an external camera lens 4140. In this manner, a person could walk about and never need to reach into their pocket or pocket book to find their camera. It should be pointed out that the camera lens 4140 can be located anywhere on the electronic eyewear including the electronic tether. Also, multiple camera lenses could be used with a still camera or a video camera. Finally, the electronic camera or video could be utilized within the electronic clip-on described earlier in this disclosure.

Figure 41B:
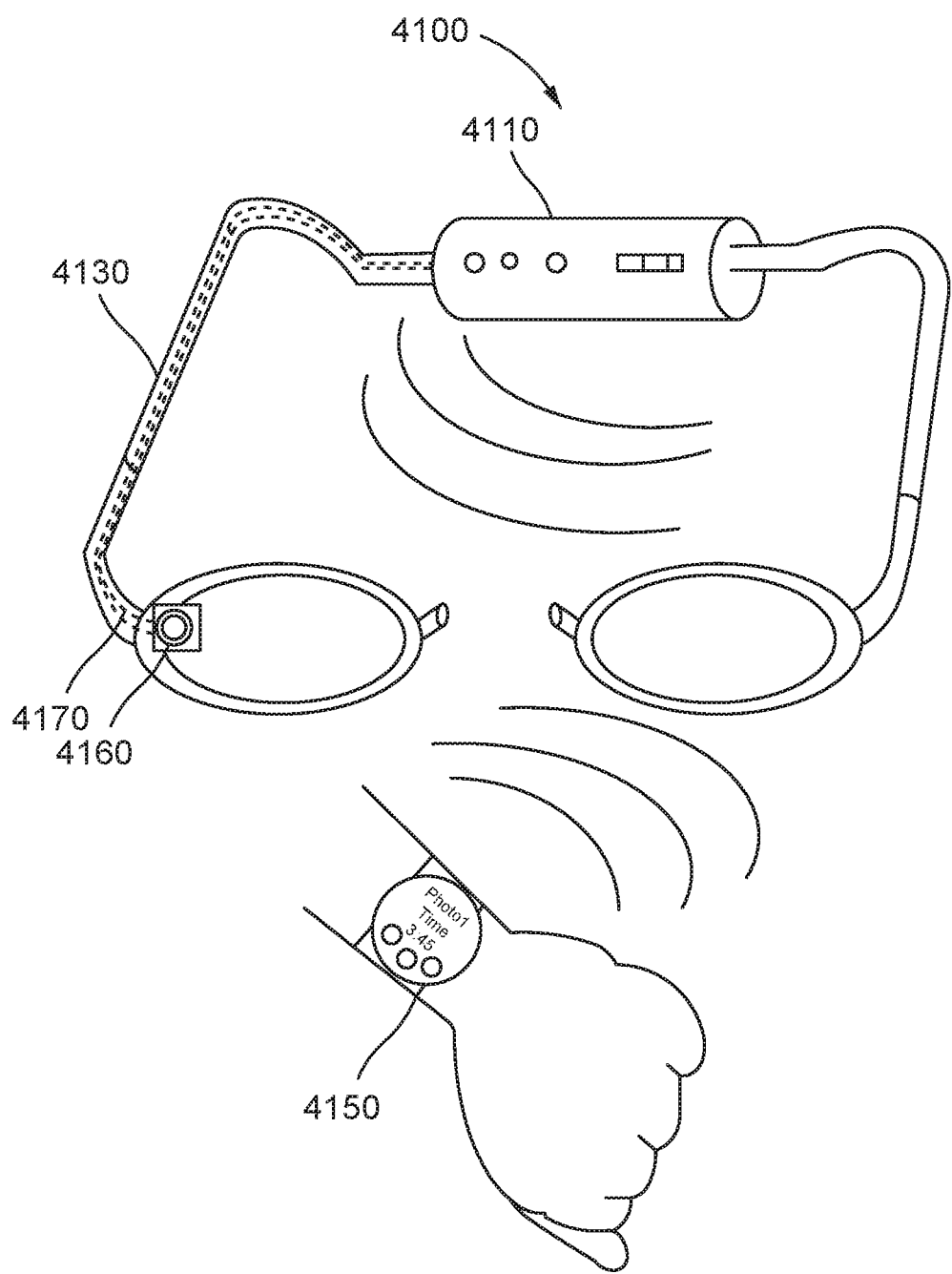

FIG. 41B illustrates an embodiment whereby the video or still camera 4160 is located directly on the front of the frame or lens, and the video signal travels down a video cable or a data bus 4170 back to the controller for storage.

Figure 42A:
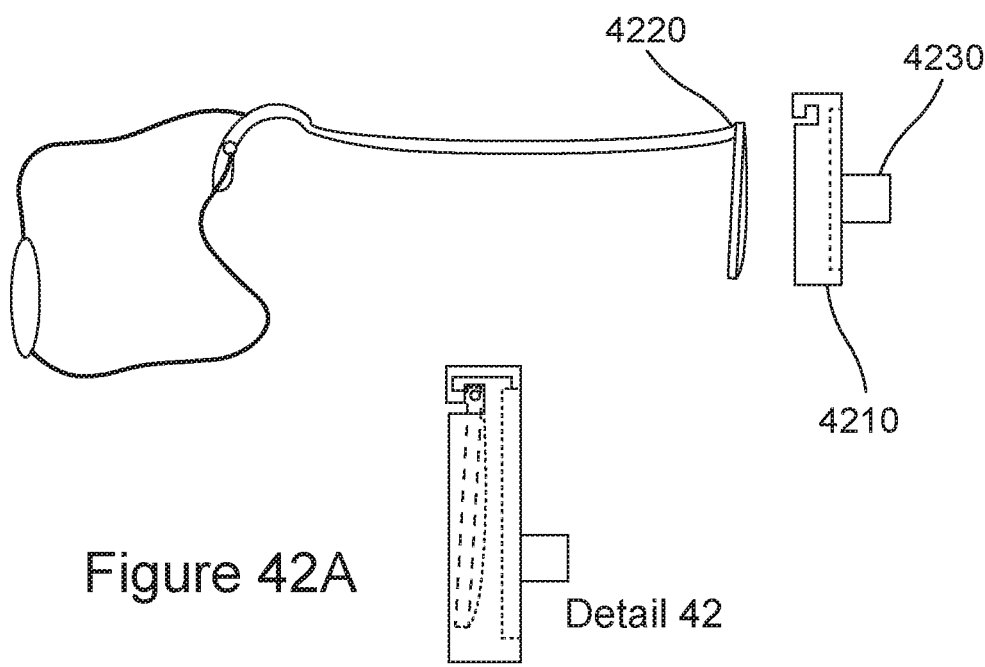
FIGS. 42A-42C illustrate another exemplary eyewear system, including a clip on heads up display, according to further aspects of the invention.
Figure 42B:
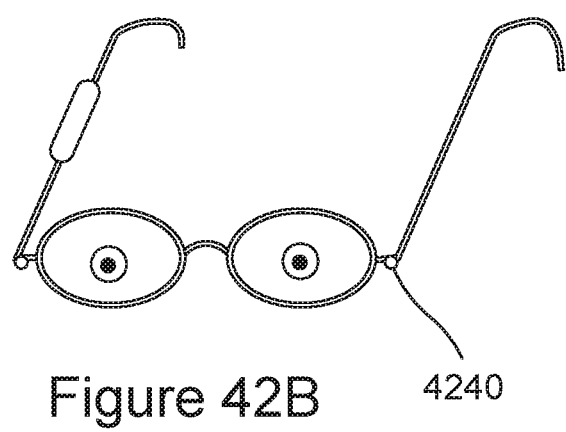
Figure 42C:
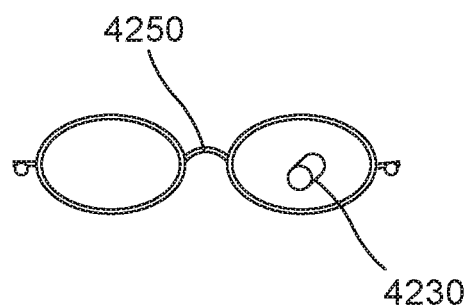

FIG. 42 shows yet another inventive embodiment of the invention. In this invention the electronic clip-on or snap-on 4210 houses a heads up display 4230. The heads up display can be that of a partial or full VGA or other available format. In the case of the preferred embodiment, a partial VGA display is utilized. In this case, when the electronic clip-on is applied to the electronic eyewear it will enable the micro-optical display housed within or on the electronic clip-on. Published patent application WO 01/06298 A1, incorporated here by reference, teaches a micro-optical display utilized with eyewear. The inventive electronic clip-on contained herein allows for a much more simplified way to position the micro-optical display within in the line of sight and also to electrically enable the micro-optical display. It should be pointed out that such a micro-optical display can be utilized with or without any electronic lens housed within the electronic clip-on. A clip on with magnetic attachment is illustrated in FIGS. 42B and 42C.

In certain other inventive embodiments, a mirror optical splitter is included within the lens housed by the clip-on and an optical image is directed through the lens house within the clip-on where it optically communicates with the optical splitter housed within the lens. In this case the clip-on allows for a virtual image to appear as if it is floating in space in front of the wearer.

Figure 43A:
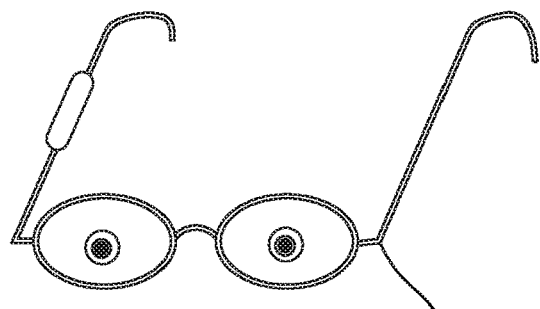
FIGS. 43A-43D illustrate another exemplary eyewear system, including a clip on heads up display and/or camera, according to further aspects of the invention.
Figure 43B:
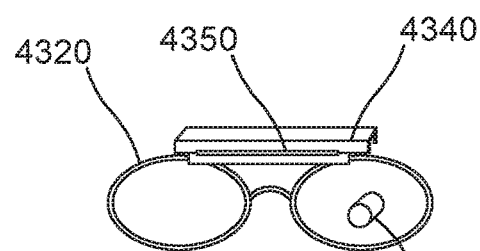
Figure 43C:
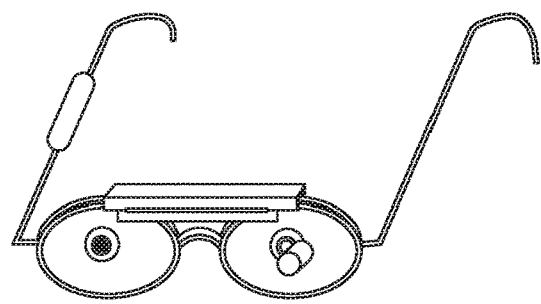
Figure 43D:
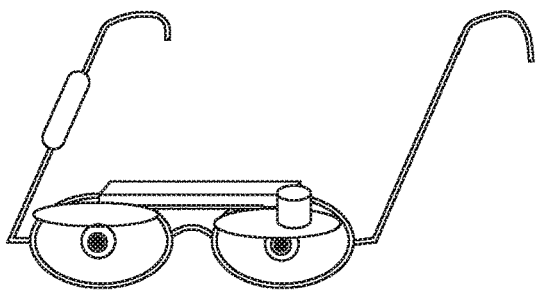

FIGS. 43A thru 43D show how the inventive electronic clip-on or electronic snap-on 4230 can remain connected at the top of the electronic eyewear 4310 to which it is attached but rotate up horizontally or pivot out of the way, using a hinge or pivot 4350 attached to a clip 4340. In this case, when wearing the inventive embodiment contained within FIG. 43B of a heads up display, the display can be positioned out of the way when it is not being utilized. Also as shown in FIGS. 43C and 43D, the inventive electronic clip can house a camera which can be positioned out of the way when not being utilized.

Figure 44:
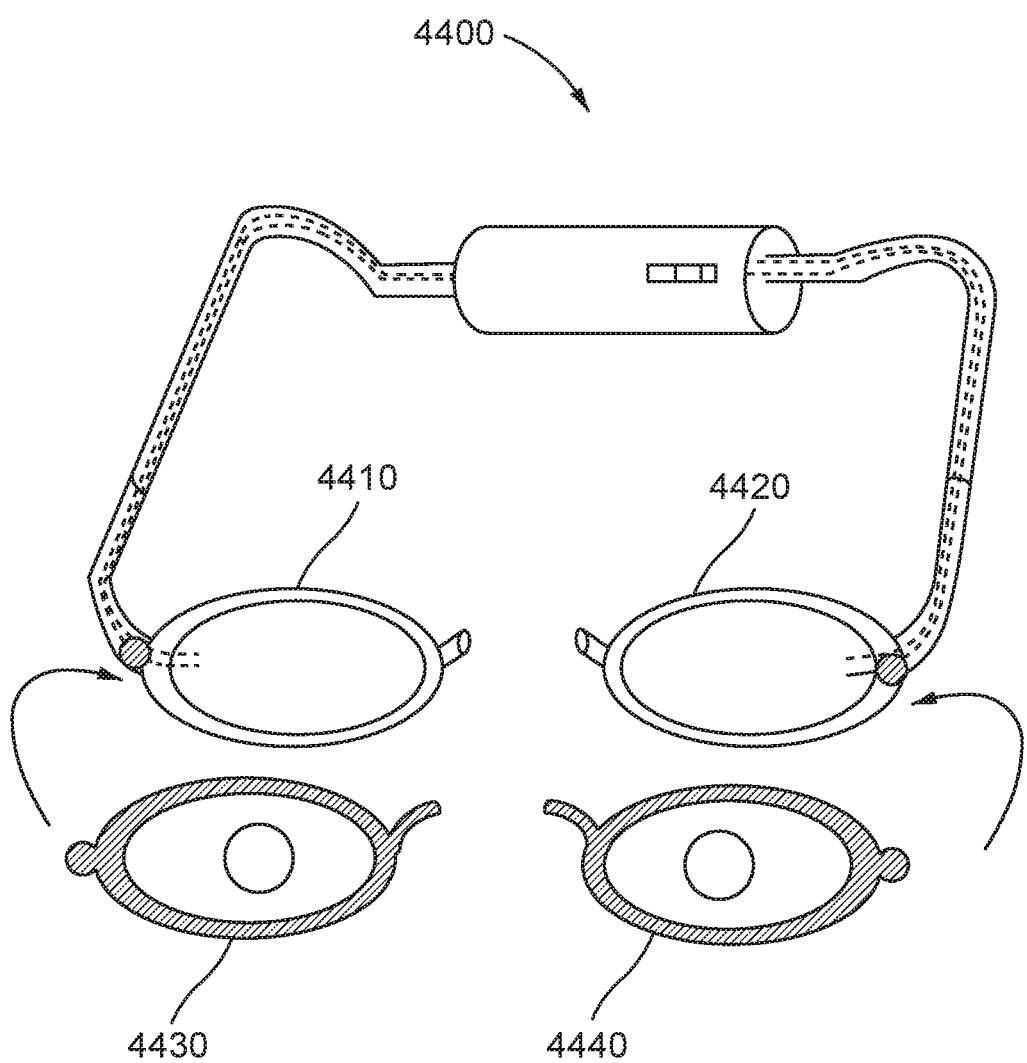
FIG. 44 illustrates another exemplary eyewear system, including clip on monocular attachments, according to further aspects of the invention.
Figure 45A:
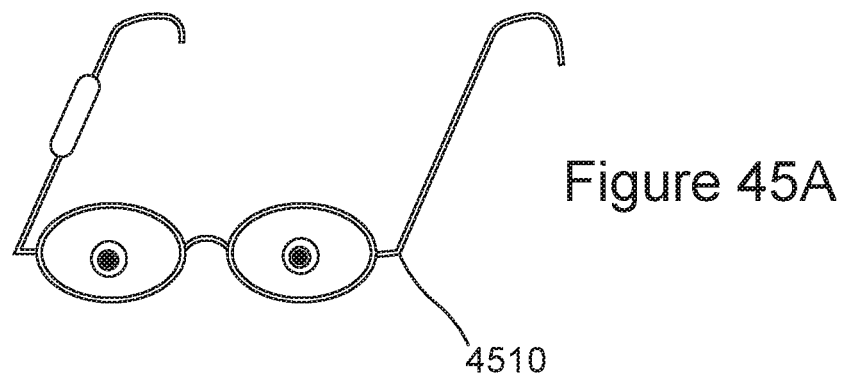
FIGS. 45A-45D illustrate another exemplary eyewear system, including a clip on visor outfitted with a micro-optical display and associated viewing optics, according to further aspects of the invention.
Figure 45B:
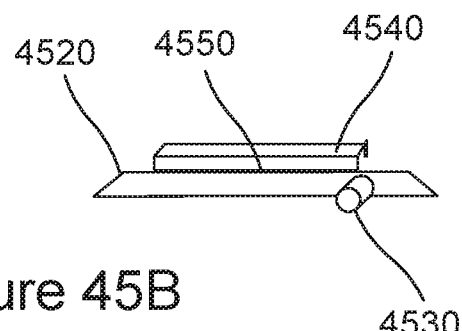
Figure 45C:
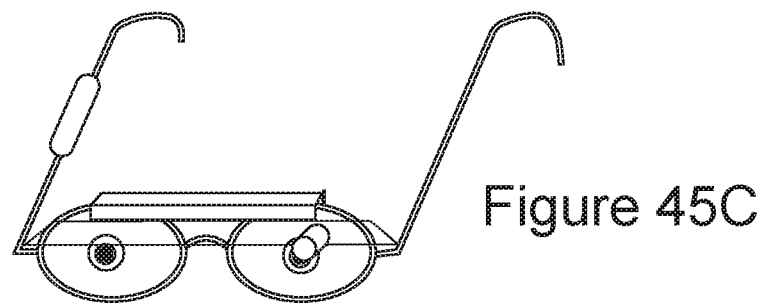
Figure 45D:
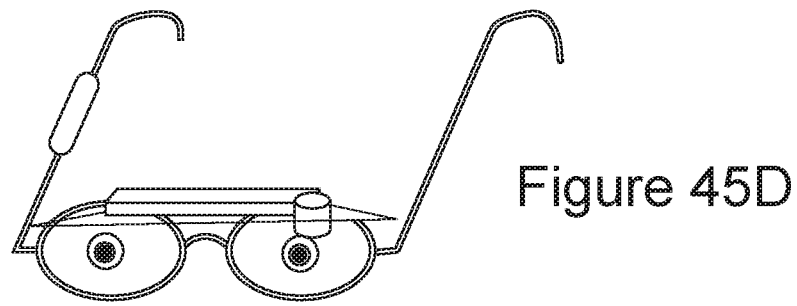

FIG. 44 illustrates clip-ons or snap-ons that are attached as monocular. In this case, monocular clip-ons 4430 and 4440 are attached to the right 4420 and left 4410 side of the split frame. In practice however, such a design could be used on a frame that did not break or separate at the nose bridge. Attachment in either case can be mechanical, magnetic, or a combination of the two. FIG. 45 illustrates a clip on visor outfitted with a micro-optical display and associated viewing optics.

Figure 46A:
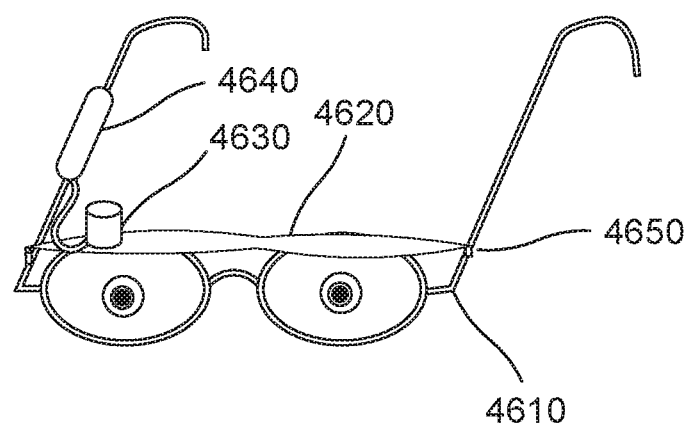
FIGS. 46A-46C illustrate another exemplary eyewear system, including a visor fitted with a micro-optical display and associated viewing optics and attached to a frame about a pivot point, according to further aspects of the invention.
Figure 46B:
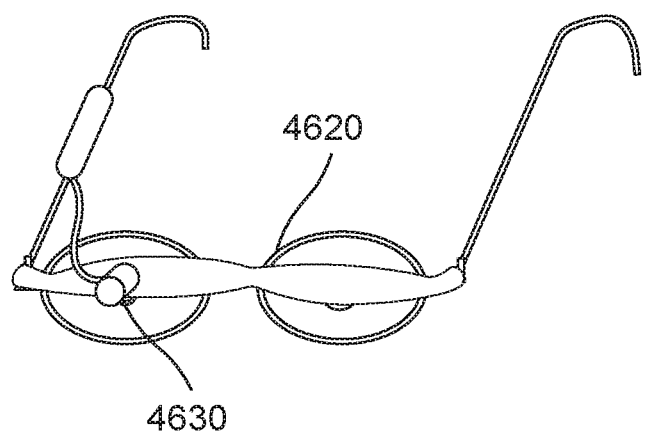
Figure 46C:
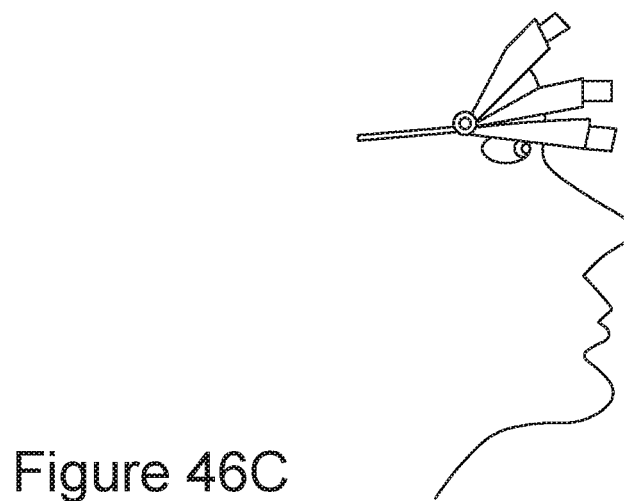

FIG. 46A illustrates an inventive embodiment wherein a Sunblade™ type visor 4620 is fitted with a micro-optical display and associated viewing optics 4630 and attached to a frame about a pivot point 4650. The illustration in FIG. 46A is that of the visor in the up position allowing the user to look straight ahead without having their view obscured by the visor and or the micro-optical display and/or the visor. FIG. 46B illustrates the visor in the down position allowing the wearer to look through the viewing optics to see the micro-optical display. FIG. 46C illustrates a side view of three different positions for the visor as worn by the user.

Figure 47:
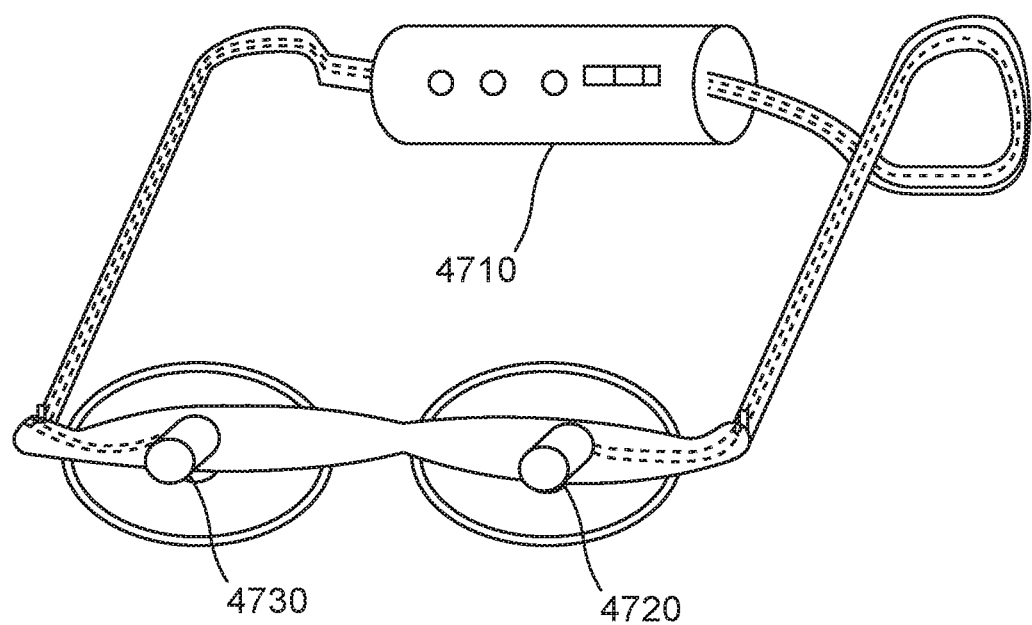
FIG. 47 illustrates another exemplary eyewear system, including a 3D viewing arrangement, according to further aspects of the invention.

FIG. 47 illustrates the use of two micro-optical displays and associated viewing optics 4720 and 4730 for producing 3D viewing by the wearer. Since each eye will be positioned in front of its own micro-optical display, there will be no need to worry about isolating left eye and right eye images provided by the video player 4710 in producing a 3D effect for the user.

Figure 48A:
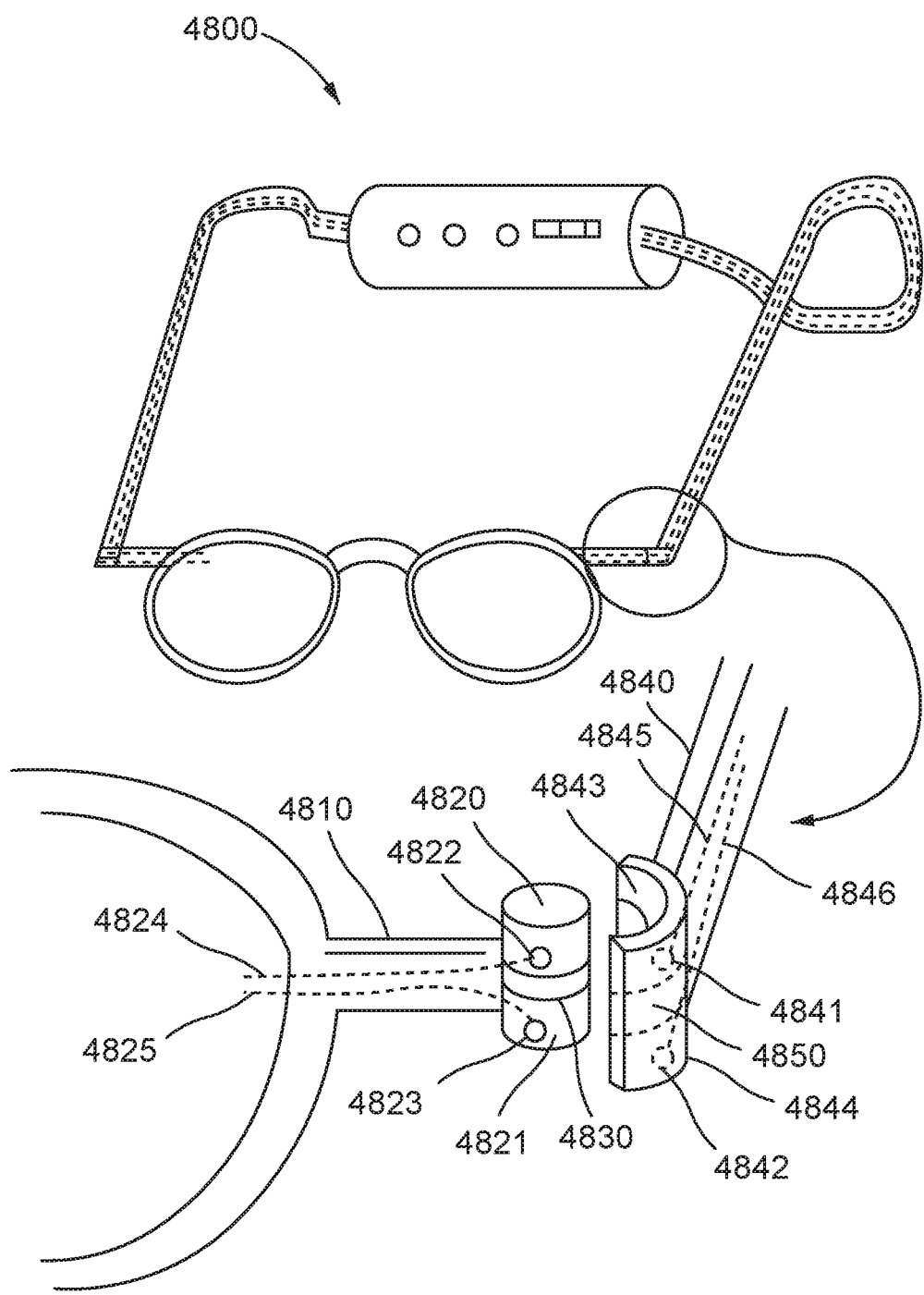
FIGS. 48A and 48B illustrate other exemplary eyewear systems, including a break-away magnetic hinge with electrical contacts, according to further aspects of the invention.

FIG. 48A illustrates another inventive embodiment of the present invention. The details of a break-away magnetic hinge with electrical contacts are shown. The frame 4810 which would house the electro-active eyewear contains two magnets 4820 and 4821 that are electrically isolated from one another with an insulating ring or cylinder 4830. Contact points 4822 and 4823 are made on or within each magnet to provide contact to the wires 4824 and 4825 that power the electroactive lens that resides in the frame (frame side for patient's right eye illustrated in the figure). The temple side of the frame 4840 includes contact points 4841 and 4842 to metallic and or magnetic surfaces 4843 and 4844, which are also electrically insulated from one another with an insulating ring 4850. The two contact points 4841 and 4842 provide electrical contact to the wires 4845 and 4846 that run up the frame stem to the power supply and/or controller attached to the back of the frame tether.

This inventive embodiment allows one to make electrical connections through a frame hinge without actually running wires through the frame hinge. It also allows one to break the frame from the temple to place the frame and frame tether over one's head. In practice the break-away magnetic frame hinge can be placed on both sides of the frame or on just one side of the frame. In the cases where the break-away magnetic frame hinge is used on just one side of the frame, the other side of the frame may include a conventional frame hinge or no frame hinge. While the break-away magnetic frame hinge has been illustrated with electrical connectivity, it is understood that the break-away magnetic frame hinge may be used for non-powered lenses and as such would only require a single magnet on either frame or temple (or both sides) of the frame hinge. Alternatively the electrical connections could be made without using the magnets as electrical contacts. In this case a single magnet on either the frame or temple side of the hinge could be used as long as the electrical contacts are properly insulated from one another.

It is should be noted that the invention contemplates the placement of the magnet on the temple and the metal hinge piece on the frame front as shown in FIG. 48A.

Figure 48B:
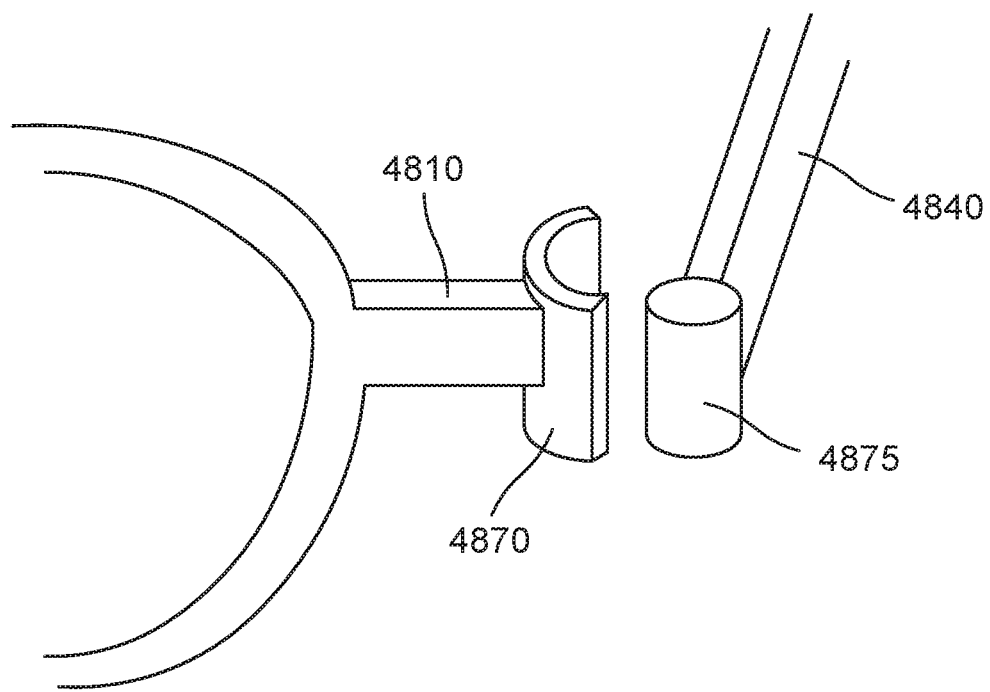

FIG. 48B illustrates an embodiment wherein, the cylinder shaped magnet 4875 is placed on the frame stem temple 4840 instead of the frame 4810. In this case, a hollow cylinder 4870 with an internal metallic surface that is attracted to the cylinder shaped magnet 4875 is placed on the frame. This is also illustrated without electrical conductive wires, since applications for such a breakaway frame hinge exist where no electrical power is used. It should be pointed out that both the cylinder shaped magnet 4875 and hollow cylinder may be made of magnetic materials; or only one piece need be magnetic as long as the other is made from a metal that can be magnetized and thus attracted by a magnet, for example ferrous metals, such steel or iron.

In another inventive embodiment of the invention, an electronic tether is used in association with a frame having two breakaway magnetic hinges, one for each side of the frame front. In this embodiment the magnets are located on the breakaway stems and the electronic tether is connected to the rear of each stem. It should be pointed out that the magnet breakaway hinge could be used for electronic eyewear or non-electronic eyewear. Also, those active individuals such as athletes and children will benefit greatly by having eyewear with breakaway hinges. Further, this inventive embodiment solves a nuisance that has been prevalent within the optical industry for decades, that being hinge screws that come loose or fall out.

The inventive embodiment solves this historical problem by doing away with the hinge screw and replacing it with a magnet. While the preferred shape of the magnet is that of cylindrical shape as shown in FIG. 48A, it could be of any shape that would provide the functionality that is needed. This inventive embodiment allows for the wearer to simply detach the frame front from their eyewear and then connect the two stems containing magnets together, forming a necklace with a magnetic closure. This can be done while maintaining the functionality of the electronic tether. In other words, while the electronic tether and stems are connected by the magnetic closure, the electronic tether plus the stems become a necklace and can be used to play audio to the wearer. By way of example only, the MP3 player could remain functioning and using the adjustable ear speakers or ear phones as shown in FIG. 30A it is possible to simply adjust for more speaker wire and thus utilize speakers in each ear while wearing the magnetically closed necklace. It should be pointed out that that the magnets can be used in any manner to accomplish this embodiment. By way of example only, a single hinge magnet can be used on each stem or one hinge magnet can be used on the stem and one on the opposite frame front where the other hinge connects, etc. It is further contemplated that the two magnetic ends of the tether can be attached to an independent locket that would be attachable and detachable to each of the two magnetic ends thus dressing up the necklace.

Finally, it should be pointed out that the structure to which the magnet of a magnetic hinge is attracted or attached to can be of any shape to provide the proper functionality. By way of example only, it can be an open cylinder (see FIG. 48A, open cylinder 4844 and FIG. 48B, 4870), a closed cylinder having both ends open, one open and the other closed. The magnet can be housed within a structure to hide or dress up the magnet. The structure, by way of example only, could simply be a metal facade that is around the magnet, thus hiding the magnet but allowing for the magnetic affect to still contribute the proper functionality needed for a magnetic hinge.

Figure 49:
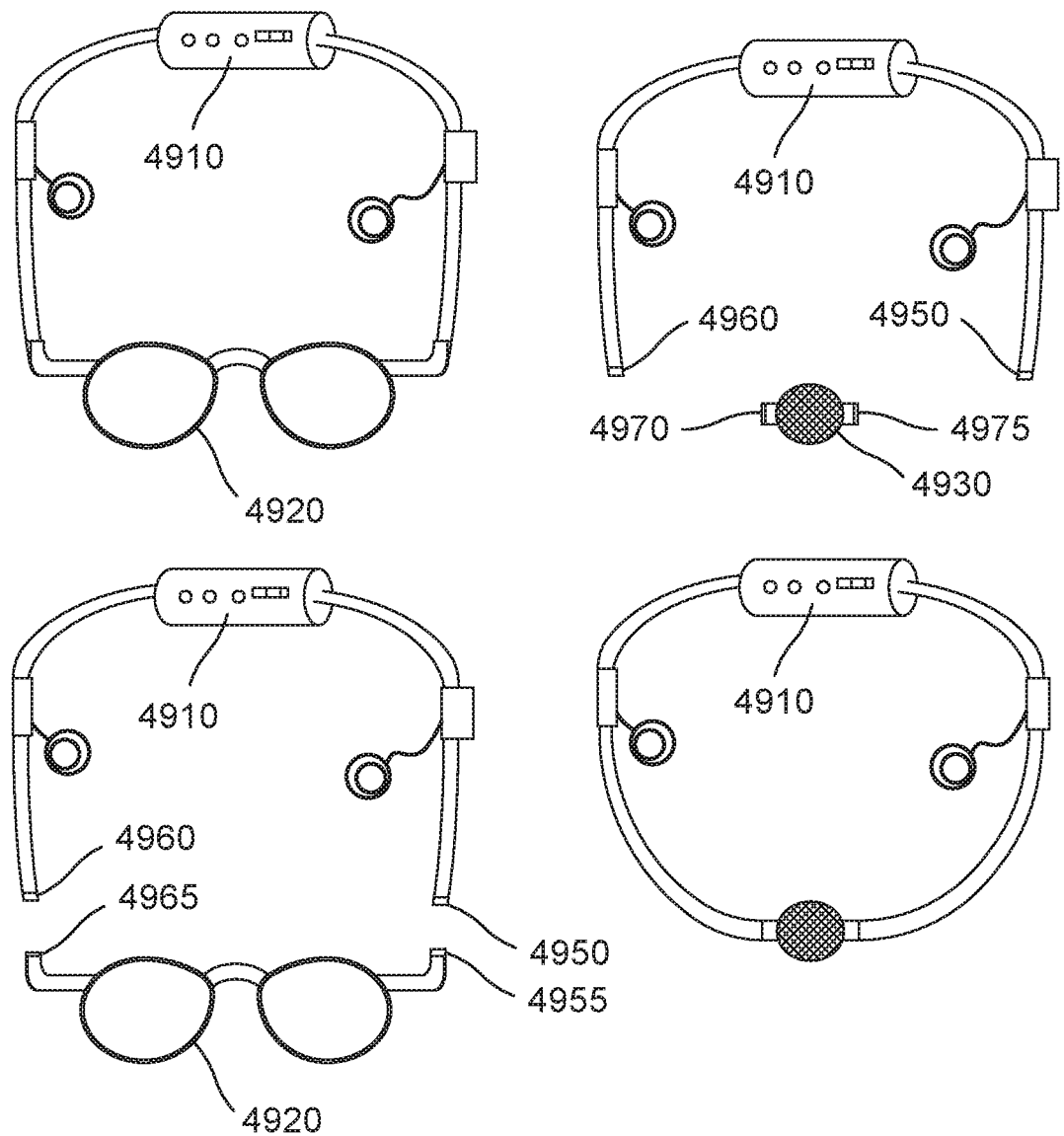
FIG. 49 illustrates an exemplary reconfigurable eyewear system, including removable parts, according to further aspects of the invention.

FIG. 49 illustrates an inventive embodiment that allows the wearer to use the electrified tether with the integrated audio player 4910 as a fashion accessory when his or her eyewear is not needed. In FIG. 49 the spectacle frame 4920 with lenses are removed and placed in a pouch or case (not shown). A decorative pendant, broach, or necklace element 4930 is then attached to the two ends of the tether that were once connected to the spectacle frame. In this manner the wearer may continue to use the audio device while not using their spectacles. In the case of FIG. 49 the two ends of the tether are connected by magnets 4950 and 4960 to the spectacle frame via magnets 4955 and 4965, and to the decorative pendant via magnets 4970 and 4975. However, the invention anticipates any type of satisfactory closure means, such means are well known in the art.

Figure 50:
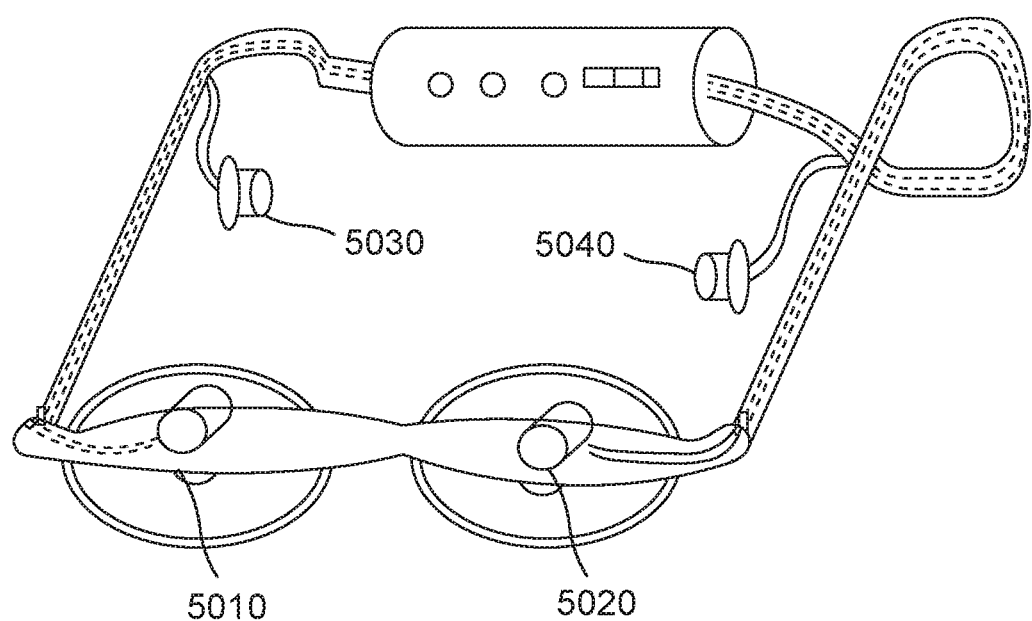
FIG. 50 illustrates another exemplary eyewear system, including optical displays placed within a visor, according to further aspects of the invention.

FIG. 50 illustrates an additional embodiment where micro-optical displays 5010 and 5020 are placed within a visor on a pair of spectacles. In this case, the micro-optical displays are placed mostly in the back of the visor and the fronts of the micro-optical displays are nearly flush with the front surface of the visor, closest to the wearer. Also FIG. 50 shows the embodiment with a integrated MPG3 player and earplugs 5030 and 5040.

While the inventors have illustrated many specific examples of how to provide power and/or drive signals to an electrically activated lens using an electronic tether or an electrified frame, it is understood that other methods may be contemplated by those ordinarily skilled in the art. Such additional methods or designs are considered within the scope and spirit of the present invention. It is also understood that the various features, while shown in separate illustrations, could be used in any number of combinations and still be within the scope of the present invention.

In some embodiments, while an electro-active lens may be used to provide vision correction as described in the present invention, the electro-active lens may also be used to provide a sunglass or tinting effect electro-actively. By using special liquid crystal layers or other electro-chromic materials, the electro-active IOL of the present invention can reduce the amount of light that hits the retina when the light levels in the environment become uncomfortably high, or reach a level that can be dangerous to the eye. The sunglass effect may be triggered automatically when a light sensor built into the IOL receives an intensity of light beyond some threshold level. Alternately, the sunglass effect may be switched remotely by the user using a wireless communication device couple to the control circuitry in the IOL. This electro-active sunglass effect may occur in milliseconds or less, in contrast to the relatively slow reaction time of seconds (or more) for commercial photosensitive chemical tints in conventional lenses. One factor in determining the reaction time of electro-active lenses is the thinness of the liquid crystal layer. For example, a 5 micron layer of liquid crystal may react in milliseconds.

Similarly, the focusing of the electro-active elements may be performed automatically by using a range finder, or a tilt meter (near distance when looking down, far distance when looking straight), or may be controlled remotely by the user using a wireless communication device.

There are a number of electro-chromic materials. One type consists of transparent outside layers of electrically conductive film that has inner layers which allow the exchange of ions. When a voltage is applied across the outer conductive layers, ions move from one inner layer to another, causing a change in tinting of the electro chromic material. Reversing the voltage causes the layer to become clear again. The electro-chromic layers can have variable light transmittance during operation, from about 5 to 80 percent. This type of electro chromic glazing has "memory" and does not need constant voltage after the change has been initiated. Further, it can be tuned to block certain wavelengths, such as infrared (heat) energy.

Another electro-chromic technology is called suspended particle display (SPD). This material contains molecular particles suspended in a solution between the plates of glass. In their natural state, the particles move randomly and collide, blocking the direct passage of light. When switched on, the particles align rapidly and the glazing becomes transparent. This type of switchable glazing can block up to about 90 percent of light. Also liquid crystal has been used to provide electro-chromic effects in sunglasses.

The systems and methods, as disclosed herein, are directed to the problems stated above, as well as other problems that are present in conventional techniques. Any description of various products, methods, or apparatus and their attendant disadvantages described in the "Background of the Invention" is in no way intended to limit the scope of the invention, or to imply that invention does not include some or all of the various elements of known products, methods and apparatus in one form or another. Indeed, various embodiments of the invention may be capable of overcoming some of the disadvantages noted in the "Background of the Invention," while still retaining some or all of the various elements of known products, methods, and apparatus in one form or another.

The invention claimed is:

1. An eyewear assembly, comprising:
a frame;
an electronic lens, held in place at least in part by a bridge in a nose region of the frame, to present a virtual image that appears to a wearer of the eyewear assembly as if the virtual image is floating in space in front of the wearer;
a controller, operably coupled to the electronic lens, to adjust the one or more optical characteristics of the electronic lens;
a tether attached to the frame;
an enclosure attached to the tether; and
a power source, disposed in the enclosure, to provide power to the controller.

2. The eyewear assembly of claim 1, wherein the controller is disposed in the enclosure.

3. The eyewear assembly of claim 1, wherein the tether is removably attached to the enclosure.

4. The eyewear assembly of claim 1, wherein the tether is removably attached to the frame.

5. The eyewear assembly of claim 1, wherein the electronic lens includes a tinted region.

6. The eyewear assembly of claim 5, wherein the tinted region includes a fixed and embedded tint.

7. The eyewear assembly of claim 1, further comprising a speaker associated with the frame to deliver an audio signal to the wearer.

8. The eyewear assembly of claim 1, wherein the power source is rechargeable.

9. The eyewear assembly of claim 1, further comprising a microphone.

10. The eyewear assembly of claim 1, further comprising a magnetic member in the nose region of the frame.

11. The eyewear assembly of claim 1, further comprising a fixed lens removably coupled to the electronic lens.

12. The eyewear assembly of claim 1, the frame including a temple piece.

13. The eyewear assembly of claim 12, wherein the temple piece has a hinged connection with the frame.

14. The eyewear assembly of claim 12, wherein the temple piece is a first temple piece, and further comprising a second temple piece, and wherein the tether is attached to the first temple piece.

15. The eyewear assembly of claim 14, wherein the tether is attached to the second temple piece.

16. The eyewear assembly of claim 1, further comprising a remote controller configured to be communicatively coupled to at least one of the controller and the power source.

17. The eyewear assembly of claim 1, wherein the electronic lens comprises at least one of: an electro-chromic tinted lens, electro-active-lens, electro-fluid lens, electro-pressure lens, electromechanically moving lens, micro-optical display, spectacle lens, or a dynamic focusing lens.

18. The eyewear assembly of claim 1, wherein an optical power of the electronic lens can be varied by application of an electrical signal.

19. The eyewear assembly of claim 1, wherein a tint of the electronic lens can be varied by application of an electrical signal.

20. The eyewear assembly of claim 1, wherein the virtual image is a 3D image.

21. The eyewear assembly of claim 1, wherein the enclosure is composed of at least one of: fabric, plastic, or rubber.

22. An eyewear assembly, comprising:
a frame including a first temple piece and a second temple piece connected to a frame front configured to rest on a bridge of a nose of a wearer;
a speaker associated with the frame to deliver an audio signal to the wearer;
an electronic lens, held in place at least in part by the frame front, to present a virtual image that appears to the wearer of the eyewear assembly as if the virtual image is floating in space in front of the wearer;
a controller, operably coupled to the electronic lens, to adjust the one or more optical characteristics of the electronic lens;
a tether attached to the first temple piece;
an enclosure removably attached to the tether, wherein the controller is disposed in the enclosure; and
a power source, disposed in the enclosure, to provide power to the controller.

23. The eyewear assembly of claim 22, wherein the speaker is connected to the frame through an electrical tether.

24. The eyewear assembly of claim 22, wherein the speaker is an earplug speaker.

* * * * *